(12) United States Patent
Mirochinik et al.

(10) Patent No.: US 10,537,340 B2
(45) Date of Patent: Jan. 21, 2020

(54) KIT INCLUDING A GUIDING SYSTEM AND A BONE MATERIAL REMOVAL DEVICE

(71) Applicant: T.A.G. Medical Devices - Agriculture Cooperative Ltd., Kibbutz Gaaton (IL)

(72) Inventors: Aryeh Mirochinik, Akko (IL); Hagay Sitry, Kibbutz Gesher HaZiv (IL); Rafi Haziza, Kiryat-Bialik (IL); Ran Weisman, Kfar-Vradim (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 248 days.

(21) Appl. No.: 15/519,844

(22) PCT Filed: Oct. 19, 2015

(86) PCT No.: PCT/IL2015/051033
§ 371 (c)(1),
(2) Date: Apr. 18, 2017

(87) PCT Pub. No.: WO2016/063279
PCT Pub. Date: Apr. 28, 2016

(65) Prior Publication Data
US 2017/0245869 A1    Aug. 31, 2017

Related U.S. Application Data

(60) Provisional application No. 62/065,701, filed on Oct. 19, 2014.

(51) Int. Cl.
*A61B 17/16* (2006.01)
*A61B 17/17* (2006.01)

(52) U.S. Cl.
CPC ...... *A61B 17/1617* (2013.01); *A61B 17/1675* (2013.01); *A61B 17/1714* (2013.01); *A61B 17/1764* (2013.01); *A61B 17/16* (2013.01)

(58) Field of Classification Search
CPC .................. A61B 17/1617; A61B 17/1764
See application file for complete search history.

(56) References Cited

U.S. PATENT DOCUMENTS

| 1,006,468 A | 10/1911 | Des Isles |
| 1,106,767 A | 8/1914 | Young |

(Continued)

FOREIGN PATENT DOCUMENTS

| CN | 101677823 | 3/2010 |
| EP | 1535579 | 6/2005 |

(Continued)

OTHER PUBLICATIONS

Communication Pursuant to Article 94(3) EPC dated Jun. 8, 2018 From the European Patent Office Re. Application No. 17205443.9. (5 Pages).

(Continued)

*Primary Examiner* — Christian A Sevilla

(57) ABSTRACT

A kit (4000, 5100) including a guiding system and a cannulated bone material removal device, the bone material removal device (4004, 5200) having a longitudinal shaft (4024, 5202) and comprising on the longitudinal shaft a radially expandable cutting portion (4028, 5208) having a longitudinally-oriented cutting edge (2124), the radial expansion comprising an increase of a cross-sectional diameter of the bone material removal device at the longitudinal position of the expandable cutting portion; and the guiding system including an arcuate element (4008, 5102), a guiding element (4010, 5104) configured to be attached to the arcuate element, and a cannula (4002, 5106), slidably insertable into a portion of the arcuate element; wherein the bone material removal device is axially displaceable within said cannula. The kit can be used in anterior cruciate ligament (ACL) reconstruction.

19 Claims, 60 Drawing Sheets

(56) References Cited

U.S. PATENT DOCUMENTS

| | | | |
|---|---|---|---|
| 1,173,882 A | 2/1916 | Smith | |
| 1,204,330 A | 11/1916 | Adair | |
| 1,237,142 A | 8/1917 | Aase | |
| 1,958,399 A | 5/1934 | Stephens | |
| 3,540,324 A | 11/1970 | Johansson | |
| 3,690,357 A | 9/1972 | Lugo | |
| 3,702,611 A | 11/1972 | Fishbein | |
| 3,945,076 A | 3/1976 | Sung | |
| 4,541,423 A | 9/1985 | Barber | |
| 4,635,737 A | 1/1987 | Miyanaga | |
| 4,710,070 A | 12/1987 | Alsen et al. | |
| 4,738,255 A | 4/1988 | Goble et al. | |
| 4,992,010 A | 2/1991 | Fischer | |
| 4,998,981 A | 3/1991 | Miyanaga | |
| 5,507,606 A | 4/1996 | Steiner | |
| 5,645,589 A | 7/1997 | Li | |
| 5,681,320 A | 10/1997 | McGuire | |
| 5,817,095 A | 10/1998 | Smith | |
| 5,839,860 A | 11/1998 | Steiner | |
| 6,358,251 B1 | 3/2002 | Mirza | |
| 6,383,188 B2 | 5/2002 | Kuslich et al. | |
| 6,679,886 B2 | 1/2004 | Weikel et al. | |
| 6,746,451 B2 | 6/2004 | Middleton et al. | |
| 6,923,813 B2 | 8/2005 | Phillips et al. | |
| 7,097,648 B1 | 8/2006 | Globerman et al. | |
| 7,172,374 B2 | 2/2007 | Burr et al. | |
| 7,179,024 B2 | 2/2007 | Greenhalgh | |
| 7,637,910 B2 | 12/2009 | Schmieding et al. | |
| 7,682,378 B2 | 3/2010 | Truckai et al. | |
| 7,914,545 B2 | 3/2011 | Ek | |
| 7,938,835 B2 | 5/2011 | Boucher et al. | |
| RE42,757 E | 9/2011 | Kuslich et al. | |
| 8,038,679 B2 | 10/2011 | Wieland | |
| 8,048,079 B2 | 11/2011 | Iannarone | |
| 8,388,621 B2 | 3/2013 | Bourque et al. | |
| 9,381,021 B2 | 7/2016 | Wagner et al. | |
| 9,950,445 B2 | 4/2018 | Miyanaga | |
| 2002/0183758 A1* | 12/2002 | Middleton | A61B 17/1617 606/79 |
| 2002/0193799 A1 | 12/2002 | Chappuis et al. | |
| 2004/0126196 A1 | 7/2004 | Burr et al. | |
| 2004/0208717 A1 | 10/2004 | Greenhalgh | |
| 2005/0113836 A1 | 5/2005 | Lozier et al. | |
| 2005/0131345 A1 | 6/2005 | Miller | |
| 2005/0240193 A1 | 10/2005 | Layne et al. | |
| 2006/0025774 A1 | 2/2006 | Fishbein et al. | |
| 2006/0149268 A1 | 7/2006 | Truckai et al. | |
| 2006/0195112 A1* | 8/2006 | Ek | A61B 17/1617 606/86 R |
| 2006/0241629 A1 | 10/2006 | Krebs et al. | |
| 2006/0264957 A1 | 11/2006 | Cragg et al. | |
| 2007/0123889 A1 | 5/2007 | Malandain et al. | |
| 2007/0276392 A1 | 11/2007 | Beyar et al. | |
| 2007/0282345 A1 | 12/2007 | Yedlicka et al. | |
| 2008/0114364 A1 | 5/2008 | Goldin et al. | |
| 2008/0154271 A1* | 6/2008 | Berberich | A61B 17/1714 606/88 |
| 2008/0183174 A1 | 7/2008 | Sikora et al. | |
| 2010/0168747 A1 | 7/2010 | Lynch et al. | |
| 2010/0249785 A1 | 9/2010 | Betts | |
| 2011/0087257 A1 | 4/2011 | To et al. | |
| 2011/0098709 A1 | 4/2011 | Malandain et al. | |
| 2011/0164937 A1 | 7/2011 | Byrne et al. | |
| 2011/0166575 A1 | 7/2011 | Assell et al. | |
| 2011/0190832 A1 | 8/2011 | Taylor et al. | |
| 2011/0251616 A1 | 10/2011 | Osman et al. | |
| 2012/0022568 A1 | 1/2012 | Koblish et al. | |
| 2012/0209274 A1 | 8/2012 | Belaney et al. | |
| 2012/0245585 A1 | 9/2012 | Kaiser et al. | |
| 2013/0165935 A1 | 6/2013 | Griffiths et al. | |
| 2014/0194880 A1 | 7/2014 | Schmieding et al. | |
| 2014/0257297 A1 | 9/2014 | Koogle, Jr. et al. | |
| 2014/0276844 A1 | 9/2014 | Bourque et al. | |
| 2014/0324052 A1 | 10/2014 | Carrison et al. | |
| 2015/0073417 A1 | 3/2015 | Norton et al. | |
| 2015/0265287 A1 | 9/2015 | Berberich | |
| 2016/0038157 A1 | 2/2016 | Mirochinik et al. | |
| 2017/0128086 A1 | 5/2017 | Slobitker et al. | |
| 2017/0224359 A1 | 8/2017 | Mirochinik et al. | |
| 2018/0360467 A1 | 12/2018 | Slobitker et al. | |

FOREIGN PATENT DOCUMENTS

| | | |
|---|---|---|
| EP | 1785103 | 5/2007 |
| ES | 2351563 | 2/2011 |
| JP | 2006-523542 | 10/2006 |
| JP | S48-62067 | 1/2012 |
| JP | 2012-187384 | 10/2012 |
| JP | 2013-516275 | 5/2013 |
| WO | WO 01/58629 | 8/2001 |
| WO | WO 2010/065047 | 6/2010 |
| WO | WO 2010/115134 | 10/2010 |
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |
| WO | WO 2017/137998 | 8/2017 |

OTHER PUBLICATIONS

Official Action dated Aug. 29, 2018 From the US Patent and Trademark Office Re. U.S. Appl. No. 15/318,677. (17 pages).
Communication Pursuant to Article 94(3) EPC dated Mar. 1, 2018 From the European Patent Office Re. Application No. 15804626.8. (3 Pages).
Notice of Reason for Rejection dated Feb. 27, 2018 From the Japan Patent Office Re. Application No. 2016-509605. (2 Pages).
Official Action dated Mar. 27, 2018 From the US Patent and Trademark Office Re. U.S. Appl. No. 15/318,677. (15 pages).
Official Action dated Mar. 29, 2018 From the US Patent and Trademark Office Re. U.S. Appl. No. 15/498,731. (15 pages).
Translation dated Mar. 22, 2018 of Notice of Reason for Rejection dated Feb. 27, 2018 From the Japan Patent Office Re. Application No. 2016-509605. (2 Pages).
Notification of Office Action dated Dec. 4, 2018 From the State Intellectual Property Office of the People's Republic of China Re. Application No. 201580069380.7 and Its Translation Into English. (4 Pages).
Official Action dated Jan. 23, 2019 From the US Patent and Trademark Office Re. U.S. Appl. No. 15/318,677. (16 pages).
Supplementary European Search Report and the European Search Opinion dated Dec. 13, 2018 From the European Patent Office Re. Application No. 16776225.1. (8 Pages).
Supplementary European Search Report and the European Search Opinion dated Jan. 30, 2019 From the European Patent Office Re. Application No. 17749987.8. (6 Pages).
Communication Relating to the Results of the Partial International Search dated May 19, 2016 From the International Searching Authority Re. Application No. PCT/IL2015/051033.
International Preliminary Report on Patentability dated Nov. 5, 2015 From the International Bureau of WIPO Re. Application No. PCT/IL2014/050381.
International Search Report and the Written Opinion dated Aug. 4, 2016 From the International Searching Authority Re. Application No. PCT/IL2015/051033.
International Search Report and the Written Opinion dated Oct. 7, 2016 From the International Searching Authority Re. Application No. PCT/IL2016/050370.
International Search Report and the Written Opinion dated Sep. 10, 2014 From the International Searching Authority Re. Application No. PCT/IL2014/050381.
Invitation to Pay Additional Fees dated Aug. 1, 2016 From the International Searching Authority Re. Application No. PCT/IL2016/050370.
Official Action dated Nov. 2, 2016 From the US Patent and Trademark Office Re. U.S. Appl. No. 14/919,921.
Official Action dated Apr. 18, 2017 From the US Patent and Trademark Office Re. U.S. Appl. No. 15/318,677. (21 pages).

(56) References Cited

OTHER PUBLICATIONS

Restriction Official Action dated Jul. 8, 2016 From the US Patent and Trademark Office Re. U.S. Appl. No. 14/919,921.
Restriction Official Action dated Feb. 11, 2016 From the US Patent and Trademark Office Re. U.S. Appl. No. 14/919,921.
Advisory Action Before the Filing of an Appeal Brief dated Feb. 28, 2018 From the US Patent and Trademark Office Re. U.S. Appl. No. 15/498,731. (3 pages).
Official Action dated Dec. 13, 2017 From the US Patent and Trademark Office Re. U.S. Appl. No. 15/498,731. (12 pages).
Applicant-Initiated Interview Summary dated Jul. 18, 2018 From the US Patent and Trademark Office Re. U.S. Appl. No. 15/498,731. (4 pages).
European Search Report dated Apr. 30, 2018 From the European Patent Office Re. Application No. 17205443.9. (5 Pages).
International Preliminary Report on Patentability dated May 4, 2017 From the International Bureau of WIPO Re. Application No. PCT/IL2015/051033. (11 Pages).
Invitation to Pay Additional Fees dated May 17, 2017 From the International Searching Authority Re. Application No. PCT/IL2017/050170. (2 Pages).
Official Action dated Jul. 17, 2017 Feb. 2016 From the US Patent and Trademark Office Re. U.S. Appl. No. 15/498,731. (13 Pages).
Official Action dated Nov. 8, 2017 From the US Patent and Trademark Office Re. U.S. Appl. No. 15/318,677. (17 pages).
Applicant-Initiated Interview Summary dated Feb. 26, 2019 From the US Patent and Trademark Office Re. U.S. Appl. No. 15/318,677. (3 pages).
International Preliminary Report on Patentability dated Aug. 23, 2018 From the International Bureau of WIPO Re. Application No. PCT/IL2017/050170. (16 Pages).
Notice of Decision of Rejection dated Sep. 4, 2018 From the Japan Patent Office Re. Application No. 2016-509605. (4 Pages).
Translation dated Oct. 5, 2018 of Notice of Decision of Rejection dated Sep. 4, 2018 From the Japan Patent Office Re. Application No. 2016-509605. (4 Pages).
International Preliminary Report on Patentability dated Oct. 19, 2017 From the International Bureau of WIPO Re. Application No. PCT/IL2016/050370. (12 Pages).
International Search Report and the Written Opinion dated Aug. 11, 2017 From the International Searching Authority Re. Application No. IL2017/ 050170. (24 Pages).
Notification of Office Action and Search Report dated Aug. 15, 2017 From the State Intellectual Property Office of the People's Republic of China Re. Application No. 201480035299.2. (6 Pages).
Translation of Notification of Office Action dated Aug. 15, 2017 From the State Intellectual Property Office of the People's Republic of China Re. Application No. 201480035299.2. (3 Pages).
Advisory Action Before the Filing of an Appeal Brief dated Apr. 1, 2019 From the US Patent and Trademark Office Re. U.S. Appl. No. 15/318,677. (8 pages).

* cited by examiner

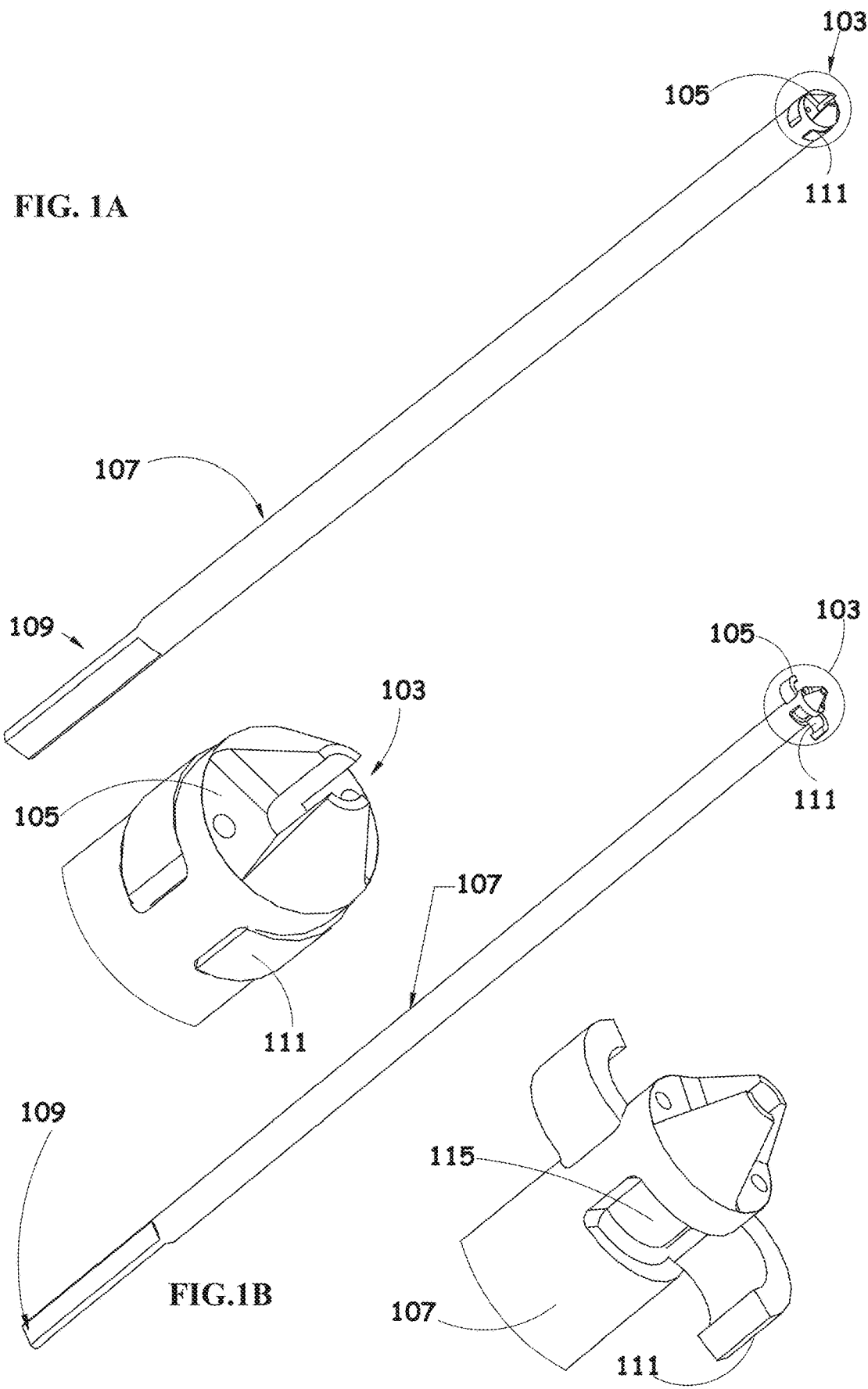

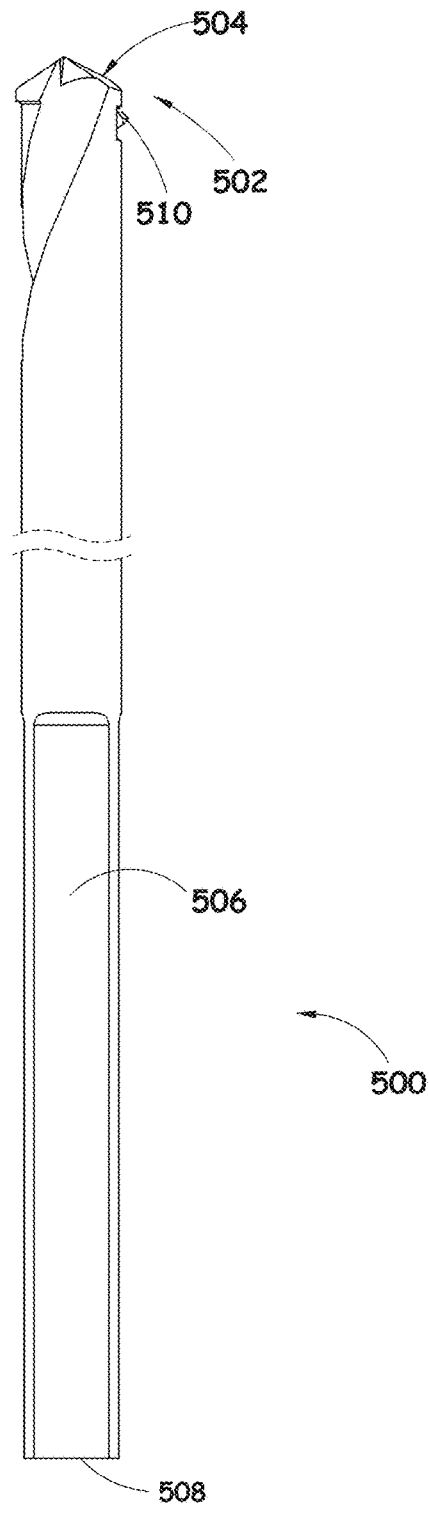
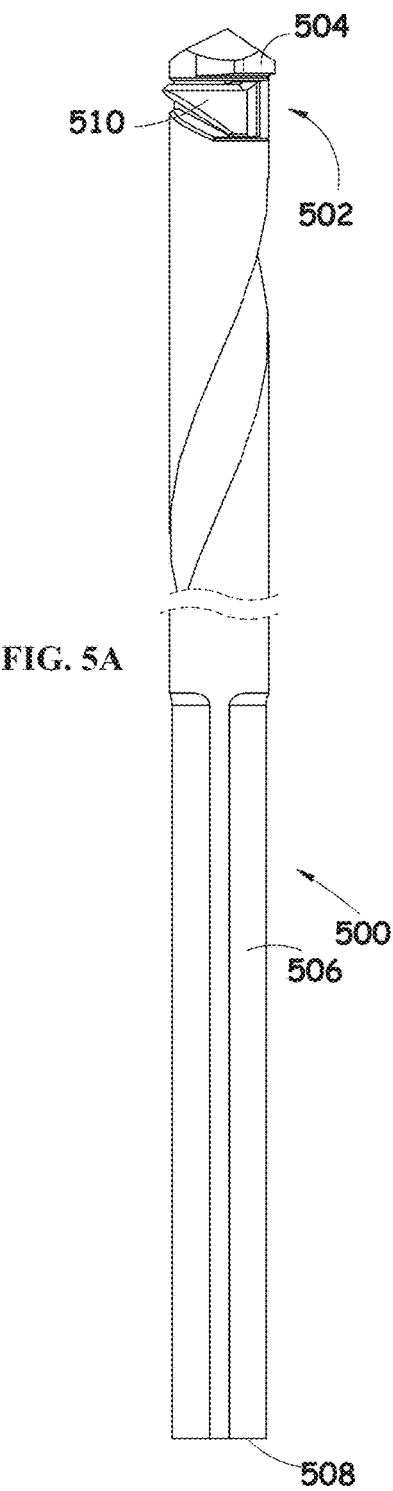
FIG. 5B
FIG. 5A

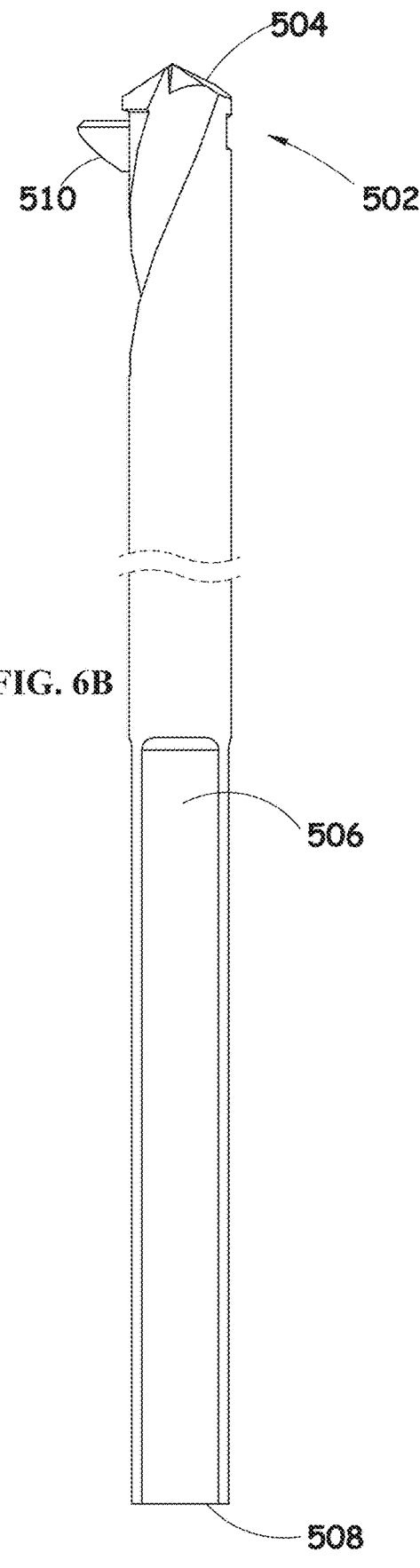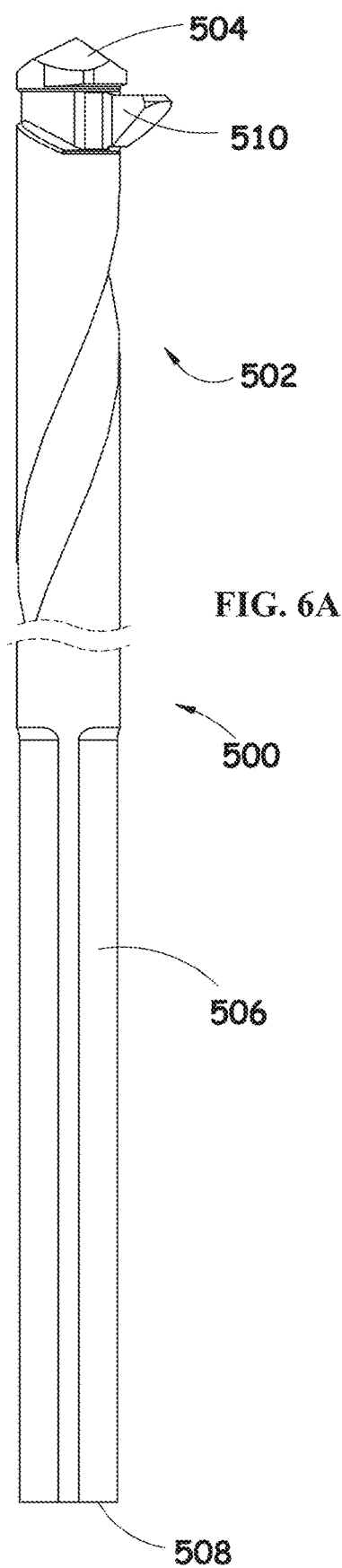

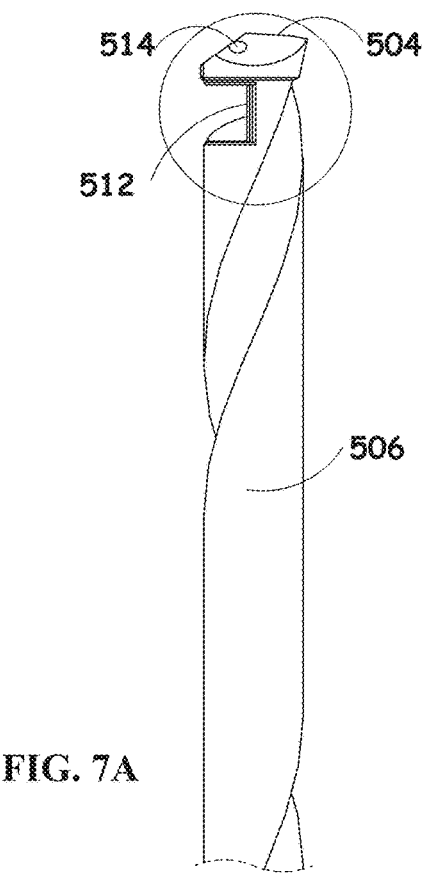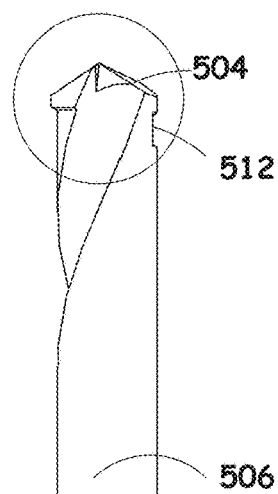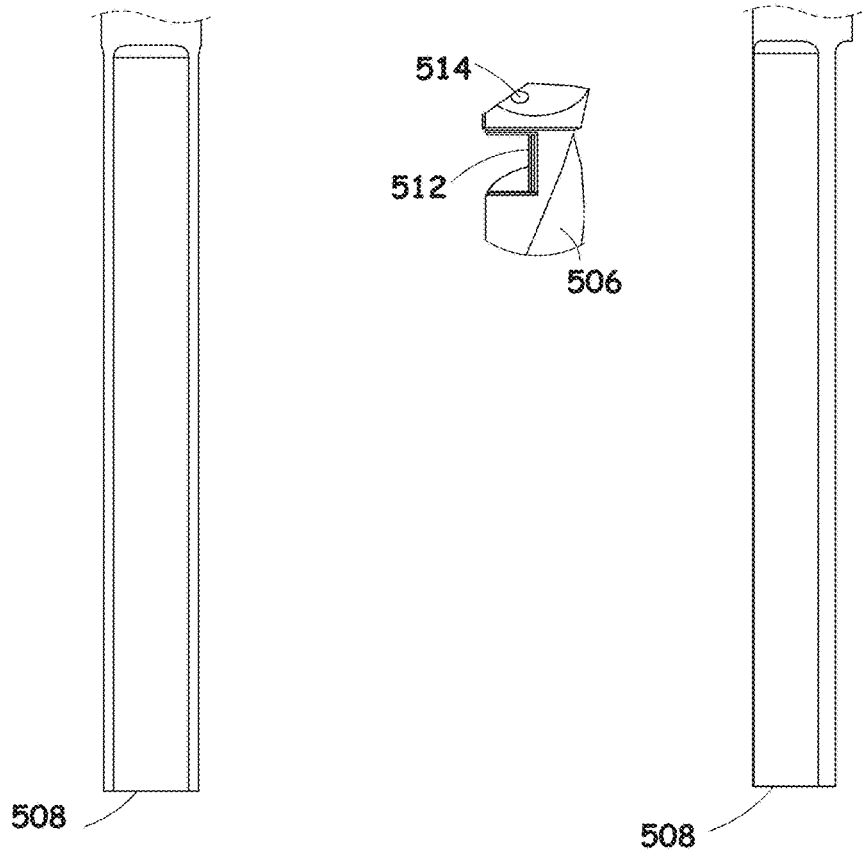
FIG. 7B
FIG. 7A

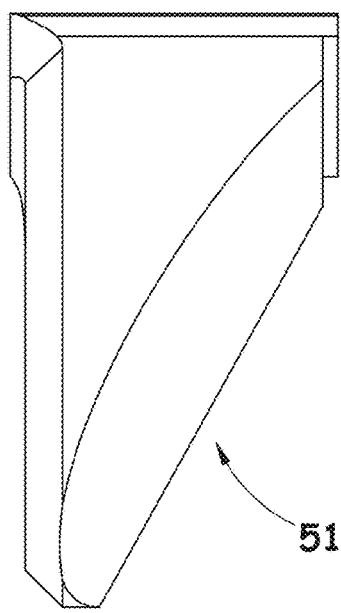
FIG. 8B
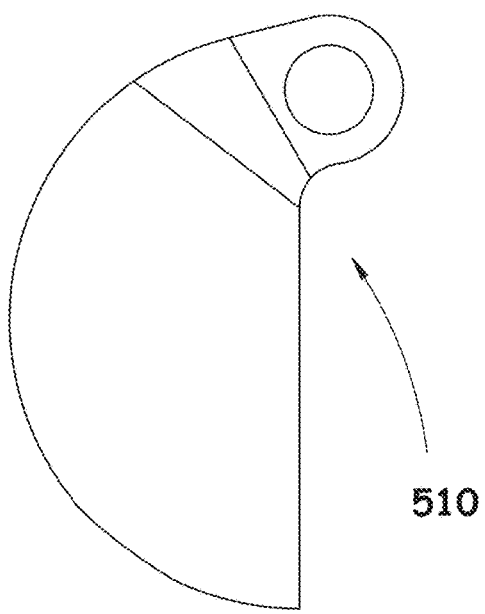
FIG. 8D
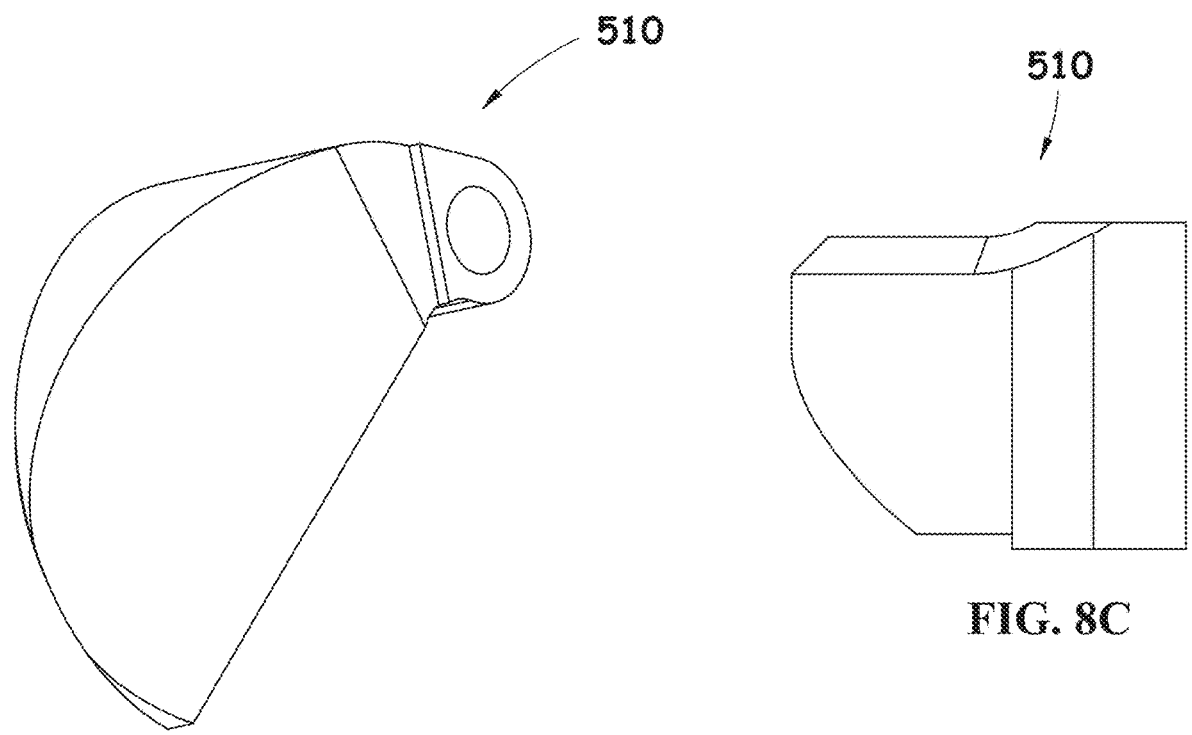
FIG. 8C
FIG. 8A

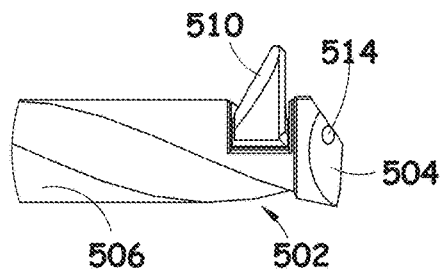
FIG. 9C
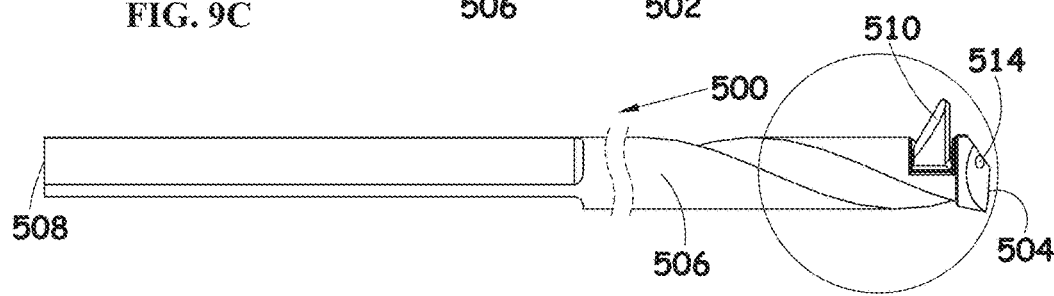
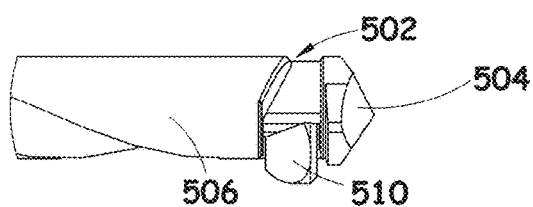
FIG. 9B
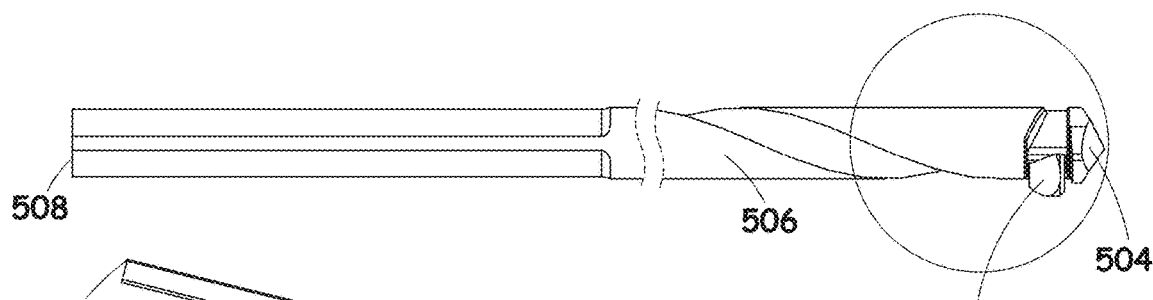
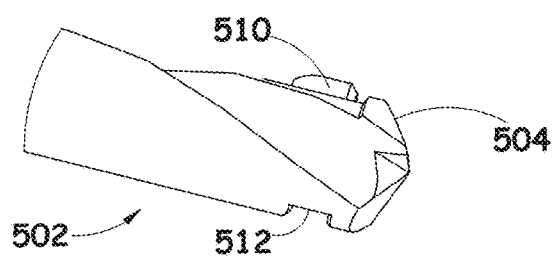
FIG. 9A

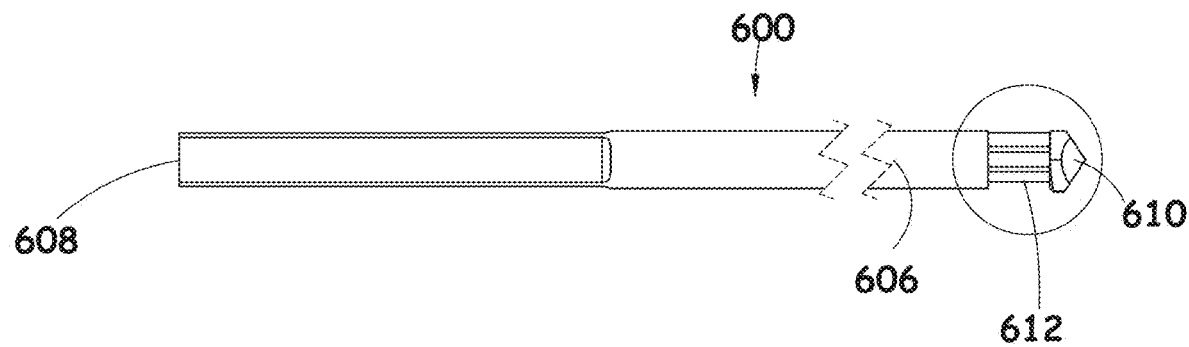
FIG. 15A
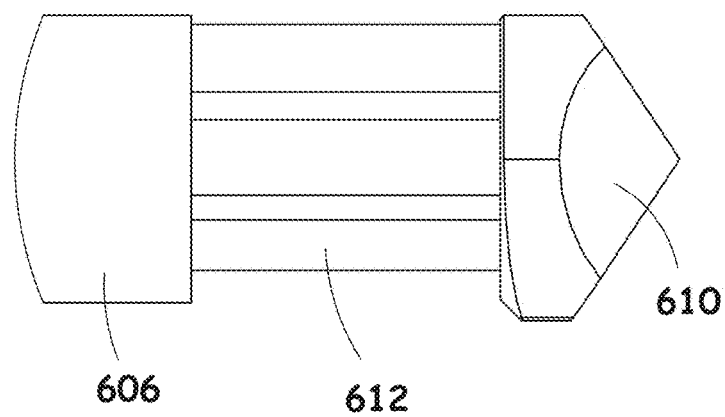
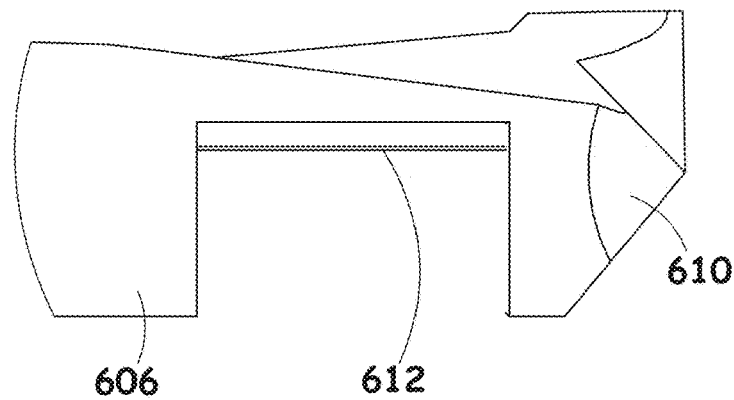
FIG. 15B
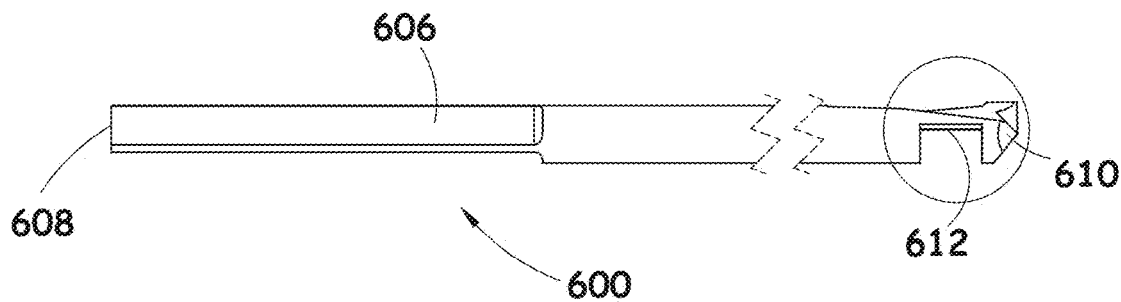

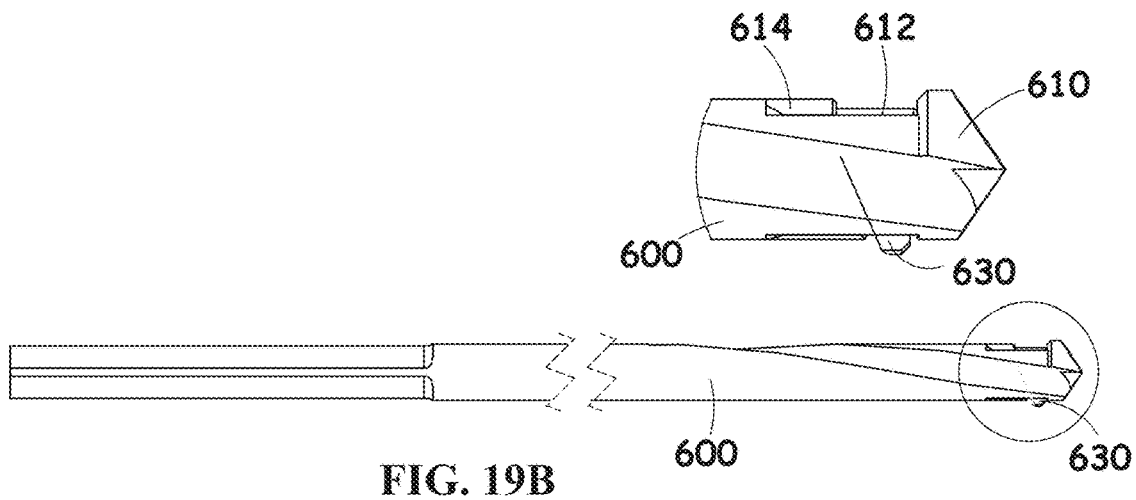
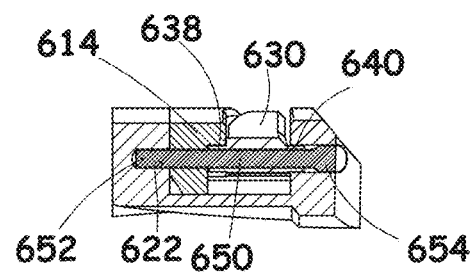
FIG. 19B
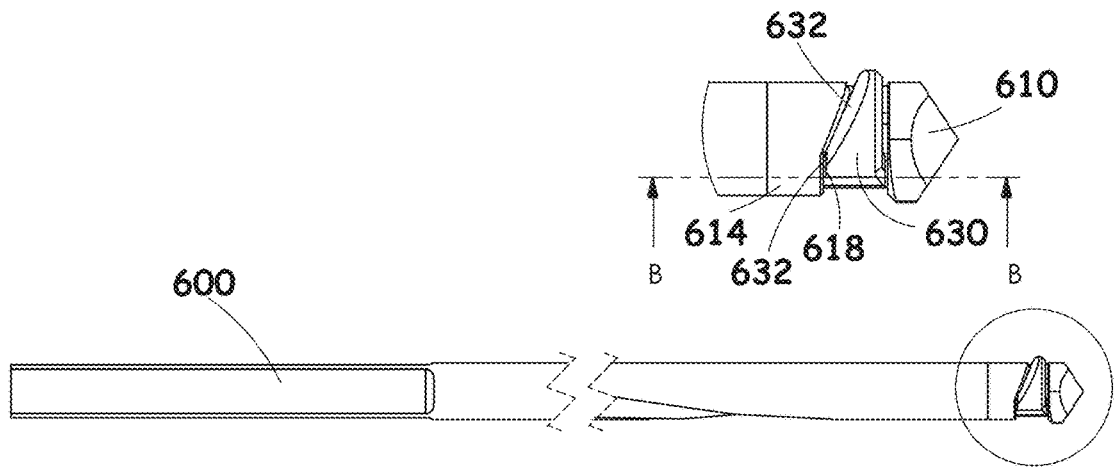
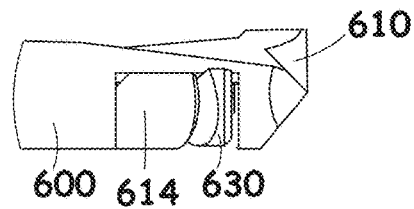
FIG. 19C
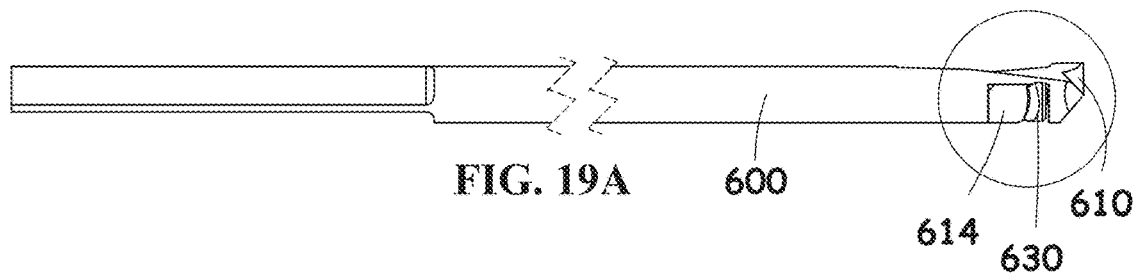
FIG. 19A

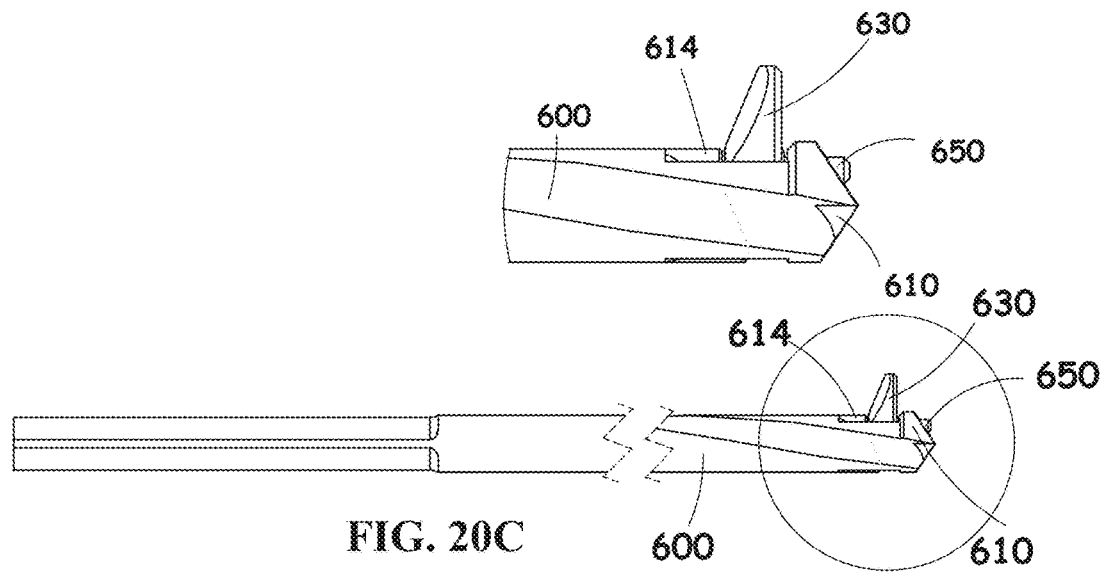
FIG. 20C
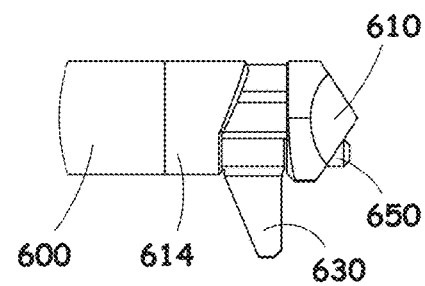
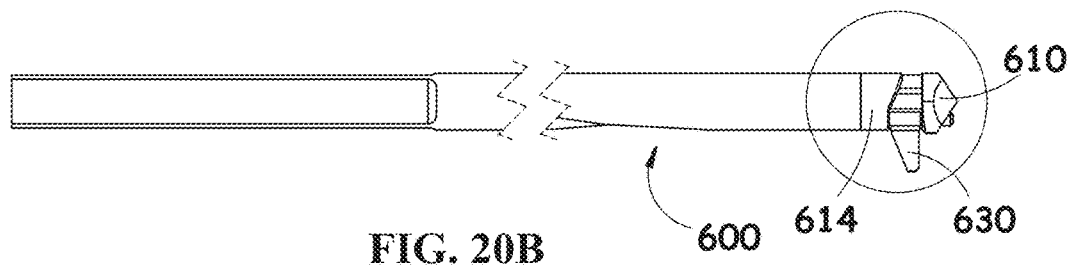
FIG. 20B
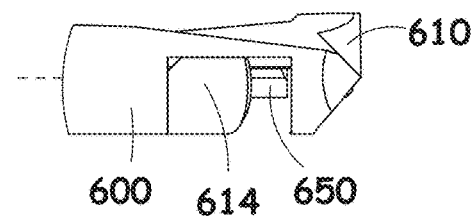
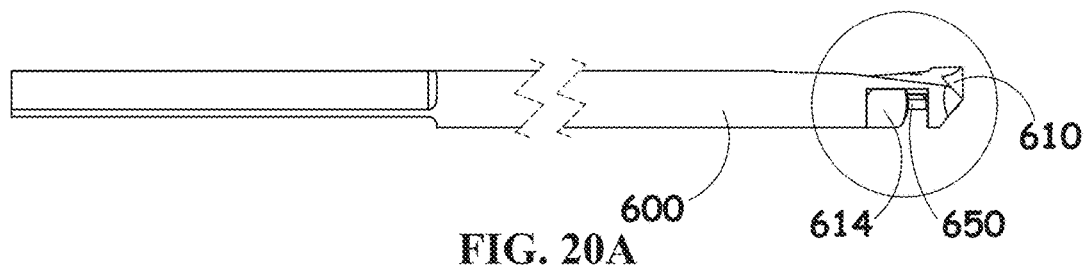
FIG. 20A

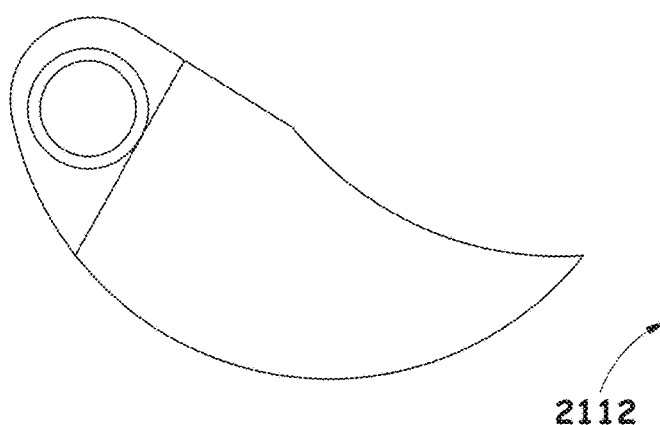
FIG. 26A
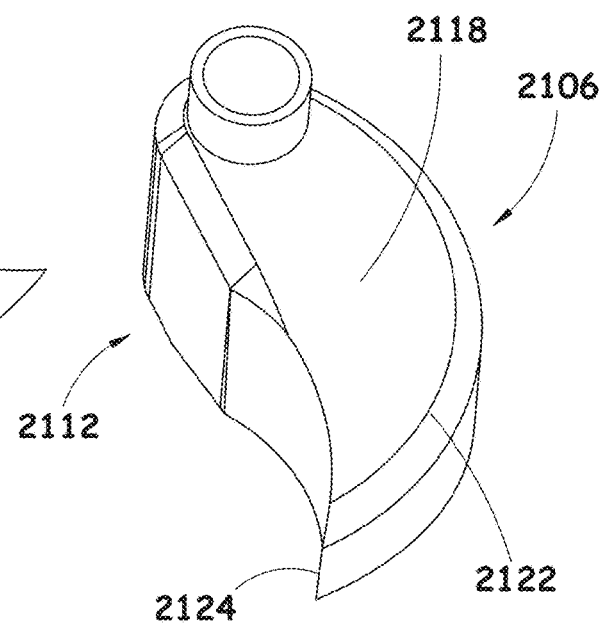
FIG. 26B
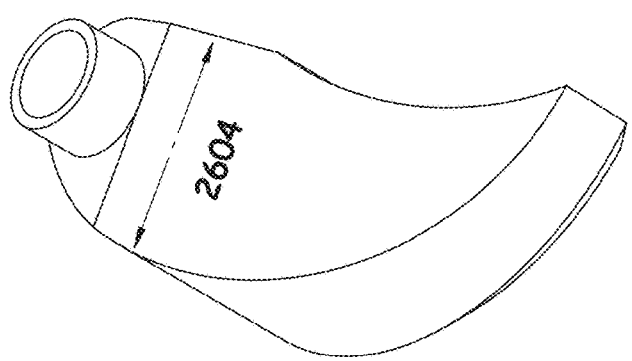
FIG. 26C
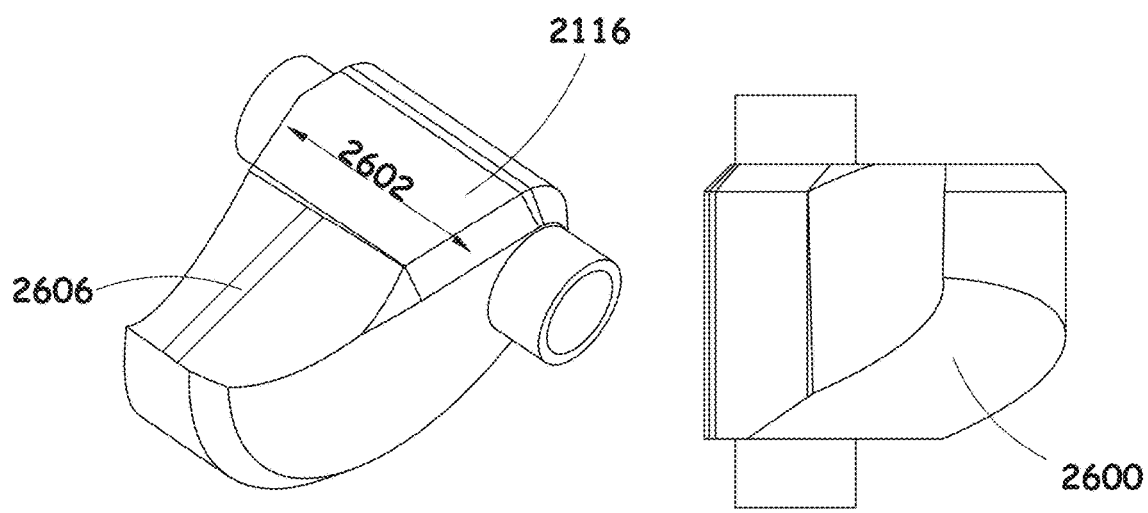
FIG. 26D
FIG. 26E

KIT INCLUDING A GUIDING SYSTEM AND A BONE MATERIAL REMOVAL DEVICE

RELATED APPLICATIONS

This application is a National Phase of PCT Patent Application No. PCT/IL2015/051033 having International filing date of Oct. 19, 2015, which claims the benefit of priority under 35 USC § 119(e) of U.S. Provisional Patent Application No. 62/065,701 filed on Oct. 19, 2014. The contents of the above applications are all incorporated by reference as if fully set forth herein in their entirety.

Reference is hereby made to PCT Patent Application No. PCT/IL2014/050381, filed on Apr. 24, 2014 and entitled "BONE MATERIAL REMOVAL DEVICES AND METHODS", the disclosure of which is hereby incorporated by reference in its entirety.

FIELD AND BACKGROUND OF THE INVENTION

The present invention in some embodiments thereof, relates to a kit including a guiding system and a bone material removal device and method of use, for example, bone removal devices which change effective diameter. More particularly, the present invention relates to fixation devices for use in arthroscopic reconstruction procedures, particularly useful in Anterior Cruciate Ligament Reconstruction (ACL) procedures.

It is known that during some arthroscopic procedures and particularly during Anterior Cruciate Ligament Reconstruction (ACL Reconstruction), a surgical tissue graft is inserted into the knee in order to replace the injured anterior cruciate ligament. The injured ligament is removed from the knee before the graft is inserted through a hole created by drilling.

Different fixation techniques are employed in order to drill a bore having predetermined dimensions through the femur and/or tibia bone.

For example, U.S. Pat. No. 5,112,337 relates to "A drill guide for drilling a tunnel in a tibia for anterior cruciate ligament replacement comprises a target hook having a point for engaging and determining the exit of the tunnel in the tibial plateau, and a handle carrying a drill guide sleeve holder and selectively variable means for adjusting and rigidly fixing the angular position of the holder relative to the plateau. The drill guide also comprises a drill sleeve longitudinally selectively adjustably received in the holder for axial movement toward and away from the point, the drill sleeve having a proximal end extending toward the point. The drill sleeve is cannulated to receive a guide wire with a sharpened point headed toward the point. Engagement means for holding the drill sleeve in a selected position is provided, thereby preselecting the desired tunnel length defined between the proximal end of said drill sleeve and the point."

SUMMARY OF THE INVENTION

There is provided, in accordance with some exemplary embodiments, a kit including a guiding system and a bone material removal device, comprising: a guiding cannula; a bone material removal device having a longitudinal shaft and comprising on the longitudinal shaft a radially expandable cutting portion having a longitudinally-oriented cutting edge, the radial expansion comprising an increase of a cross-sectional diameter of the bone material removal device at the longitudinal position of the expandable cutting portion; wherein the bone material removal device is axially displaceable within the cannula.

According to some embodiments, the kit further comprises: a connecting member, wherein the guiding cannula is slideable in a longitudinal direction while attached to the connecting element; a guide arm attachable to the connecting member element at a base end of the guide arm, and having a terminal structure at another end, wherein the terminal structure is located at or at least partially surrounding a region along the longitudinal direction when the guide arm and element are attached.

According to some embodiments, the connecting member is arcuate in shape.

According to some embodiments, the expandable cutting portion comprises at least one cutting tooth configured to radially deploy from a distal portion of the longitudinal shaft.

According to some embodiments, the expandable cutting portion expands by pivoting on a hinge element oriented to extend along the longitudinal shaft.

According to some embodiments, an inner diameter of the guiding cannula is sized to fittingly receive a portion of the longitudinal shaft which is axially displaceable within the cannula.

According to some embodiments, the longitudinal shaft is at least 4 mm in diameter.

According to some embodiments, a clearance between the longitudinal shaft and the inner diameter of the guiding cannula is less than 0.1 mm.

According to some embodiments, the bone material removal device is cannulated.

According to some embodiments, the radially expandable cutting portion in a non-expanded position extends radially beyond any adjacent circumference of the non-expanding longitudinal shaft, and the inner diameter of the guiding cannula is sized to fittingly receive the expandable cutting portion in the non-expanded position.

According to some embodiments, the kit further comprises at least one stopper, slidably displaceable over the cannula along the direction of the axial displacement.

According to some embodiments, the bone material removal device further comprises a pin extending substantially transversely to the longitudinal shaft, and positioned where it contacts the at least one stopper to limit longitudinal travel of the bone material removal device.

According to some embodiments, the pin is attached to the longitudinal shaft by a rotating bearing, such that the shaft is free to rotate while the pin remains rotationally stationary.

According to some embodiments, the longitudinal position of the pin is fixed relative to the longitudinal shaft.

According to some embodiments, the stopper includes a groove formed therein, sized and positionable to allow displacement of the pin through it while the stopper is attached to the cannula.

According to some embodiments, the terminal structure at least partially surrounds the region along the longitudinal direction, outside a circumference having the diameter of the longitudinal shaft of the bone material removal device.

According to some embodiments, the at least partially surrounding comprises extending around at least 33% of a circumference defined by a diameter of the bone material removal device.

According to some embodiments, the terminal structure is hook-shaped.

According to some embodiments, the terminal structure is fork-shaped.

According to some embodiments, the guiding cannula comprises a distance scale indicating overall bone tunnel length provided longitudinally therealong, and the scale is marked such that a distal-most slideable position of the cannula provides a reference position defining a smallest distance between a distal tip of the guiding cannula and the terminal structure, with larger distances indicated on the scale by increasing in value toward the distal end of the guiding cannula.

According to some embodiments, the cannula comprises a widening which interferes with the connecting member to limit distal sliding motion of the cannula to a position defining the smallest distance.

According to some embodiments, distances of the scale are marked as the actual length of a bone tunnel defined by the relative positions of the cannula and the terminal structure of the guide arm.

According to some embodiments, a second scale is marked on the bone material removal device, and is markable to provide an indication of retrograde cutting distance as the bone material device is withdrawn proximally.

According to some embodiments, the two scales are coordinated, such that a current distance reading on the scale marked on the bone material removal device gives a position on the bone material removal device scale to which longitudinal travel should be limited during formation of a bone tunnel.

There is provided, in accordance with some exemplary embodiments, a kit including a guiding system and a bone material removal device, comprising: a guiding cannula; a connecting member, wherein the guiding cannula is slideable in a longitudinal direction while attached to the connecting member; a guide arm attachable to the connecting member at a base end of the guide arm, and having a terminal structure at another end, wherein the terminal structure is located at or at least partially surrounding a region along the longitudinal direction when the guide arm and connecting member are attached; and a cannulated bone material removal device having a longitudinal shaft, axially displaceable within the cannula.

According to some embodiments, an inner diameter of the guiding cannula is sized to fittingly receive a portion of the longitudinal shaft which is axially displaceable within the cannula.

According to some embodiments, the longitudinal shaft is at least 4 mm in diameter.

According to some embodiments, a clearance between the longitudinal shaft and the inner diameter of the guiding cannula is less than 0.1 mm.

There is provided, in accordance with some exemplary embodiments, a method of drilling a bone tunnel in a bone comprising: positioning a guiding cannula on the bone; inserting a bone material removal device into the cannula; forming a bone tunnel in the anterograde direction through the bone while advancing the bone material removal device; expanding an expandable distal portion of the bone material removal device; and expanding the bone tunnel in the retrograde direction while withdrawing the bone material removal device; wherein the bone material removal device rotates in opposite directions during the advancing and the withdrawing, respectively.

According to some embodiments, the expandable distal portion comprises a cutting tooth pivotably attached to a hinge member longitudinally oriented along a longitudinal shaft of the bone material removal device.

According to an aspect of some embodiments there is provided a kit including a guiding system and a bone material removal device, including an arcuate element, a guiding element configured to be attached to the arcuate element, a cannula, slidably insertable into a portion of the arcuate element, a cannulated bone material removal device having a longitudinal shaft, which is axially displaceable within the cannula.

Preferably, there is a stopper, slidably displaceable over the cannula. The stopper preferably includes a groove formed therein.

In some embodiments of the present invention, the bone material removal device further includes a pin extending substantially transversely to the longitudinal shaft.

Preferably, the pin is displaceable through the groove of the stopper.

In some embodiments of the present invention, the bone material removal device has an expandable cutting tooth.

According to an aspect of some embodiments there is provided a bone material removal device comprising an elongated shaft, at least one bone material removal element for widening a bore in a bone, the element coupled to the shaft, the element movable from a closed position, in which the element is only partially received within the shaft, to an open position in which the element extends radially away from the shaft, wherein the shaft comprises a section defining a generally cylindrical volume of rotation, and at least a portion of the bone removal element extends beyond the volume of rotation when the element is in the closed position.

In some embodiments, the bone material removal element is a pivotable cutting tooth coupled to the shaft by a hinge.

In some embodiments, the portion of the bone removal element protrudes to a distance ranging between 0.05 mm to 0.5 mm from the volume of rotation of the shaft when in the closed position.

In some embodiments, the cutting tooth comprises a cutting face formed with a concavity. Optionally, a radius of curvature of the concavity ranges between 1.5 mm-4 mm.

In some embodiments, the cutting tooth comprises a cutting face formed with a flat portion.

In some embodiments, the tooth freely pivots on the hinge to open as a result of reversal of rotation direction of the device.

In some embodiments, the hinge comprises proximal and distal elongated extensions received within the shaft to firmly attach the hinge to the shaft.

In some embodiments, the shaft comprises a recess shaped and sized for receiving at least a portion of the tooth, the recess shaped to limit rotational movement of the tooth.

In some embodiments, the device is a drill bit, and the shaft comprises one or more flutes.

In some embodiments, a concavity at the cutting face of the tooth faces a diametrically opposing direction from the flute of the shaft when the tooth is open, to provide an additional path for removal of extracted bone material.

In some embodiments, a bottom surface of the cutting tooth is non-planar to engage an irregular geometry of the bone surface.

In some embodiments, the shaft comprises a tapering head having a pointed distal tip.

In some embodiments, the bone removal element includes at least one supporting element extending in parallel to a longitudinal axis of the shaft and provides for pivotable connection of the bone removal element to the shaft.

In some embodiments, the bone removal element is irremovably attached to the shaft by at least one of a hinge pin or said supporting element.

In some embodiments, the bone removal element extends from the shaft upon rotation due to centrifugal force.

In some embodiments, the bone removal element extends perpendicularly to a longitudinal axis of the shaft.

In some embodiments, the device is adapted to operate in a bore drilling configuration, having a rotation direction in which the bone removal element is in the closed position.

In some embodiments, the device is adapted to operate in a bore widening configuration in which the bone removal element is in the open position. Optionally, the configuration is selected by selecting a direction of rotation.

In some embodiments, the device is cannulated to be inserted over a guide wire.

In some embodiments, the bone removal element extends at least 2 mm beyond the volume of rotation when in the open position.

In some embodiments, the device is a reamer.

In some embodiments, the device comprises a plurality of cutting teeth.

In some embodiments, the device comprises at least one structure configured for resisting further entry of the bone removal element into the shaft in the closed position.

In some embodiments, the structure resisting further entry of said bone removal element into the shaft are one or more walls of a recess in the shaft in which the element is received.

In some embodiments, the structure is an elastic element, allowing for the bone removal element to be pushed into the shaft and be fully concealed within the shaft.

In some embodiments, the bone removal element is a cutting tooth, wherein at least a portion of the cutting tooth is large enough to act as the structure resisting further entry of the tooth into the shaft.

According to an aspect of some embodiments of the invention there is provided a bone material removal kit comprising an elongated shaft, a plurality of cutting teeth, including a first tooth attachable to the shaft, and a second different than the first tooth in at least a radial dimension, the second tooth attachable to the shaft, wherein when one of the teeth is attached to the shaft, the tooth is movable from an open position, in which it extends radially away from the shaft, to a closed position; wherein when the first tooth is in a closed position, the first tooth is at least partially received within the shaft; and wherein when the second tooth is in the closed position, the second tooth is fully received within the shaft.

In some embodiments, the first tooth is larger than the second tooth in at least a radial dimension, so that it contacts side walls of a bore formed in the bone in the closed position.

In some embodiments, the first tooth is configured for opening inside the bore in the bone, utilizing resistance of the walls acting on the tooth.

In some embodiments, the second tooth is configured for opening outside a bore in the bone, utilizing centrifugal force.

According to an aspect of some embodiments there is provided a method for forming a bore in a bone, and widening at least a portion the bore, comprising: inserting a bone material removal device comprising a cutting tooth into a bone, rotating the device in a first direction to form a bore in the bone while at least a portion of the cutting tooth protrudes externally to a shaft of the device, the portion contacting bone tissue at the walls of the bore, when said device is advanced into the bore, reversing the rotation direction of the device, utilizing resistance of the walls of the bore acting on the portion of the cutting tooth to open the tooth, pulling the device through the bore in a direction opposite the insertion direction, to widen at least a portion of the bore using the opened cutting tooth.

In some embodiments, a diameter of the bore is defined by an extent in which the cutting tooth protrudes externally to the device when the tooth is in a closed position. In some embodiments, the method further comprises advancing the device through the bore until the cutting tooth exits the bone, and reversing a rotation direction to open the cutting tooth utilizing centrifugal force.

In some embodiments, the method further comprises rotating the device in the first rotation direction to close the tooth and remove the device from the widened bore. In some embodiments, the method further comprises clearing removed bone material in front of the open cutting tooth by means of a curved cutting surface of the cutting tooth.

In some embodiments, a diameter of the bore is widened by at least 30%.

In some embodiments, the device is passed through an existing bore in a bone to widen it.

In some embodiments, inserting comprises drilling. Optionally, drilling comprises drilling using a flexible shaft comprising at least a segment formed with a spring.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 1A-1B show a bone material removal device comprising an expandable distal tip shown in an open and closed configuration, according to some embodiments of the invention;

FIGS. 5A-5B are two elevation views of a bone material removal device comprising an expandable distal tip, constructed according to another embodiment of the present invention, showing the expandable tip in a closed configuration;

FIGS. 6A-6B are two elevation views of the bone material removal device of FIGS. 5A-5B, showing the expandable tip in an expanded configuration, according to some embodiments of the invention;

FIGS. 7A-7B are two elevation views of a drill of the bone removal device of FIGS. 5A-6B, according to some embodiments of the invention;

FIGS. 8A-8D are a pictorial view and three different elevation views of a cutting tooth of the bone removal device of FIGS. 5A-6B, according to some embodiments of the invention;

FIG. 9A is a pictorial view and an enlargement view of the bone material removal device of FIGS. 5A-6B in a closed configuration, according to some embodiments of the invention;

FIG. 9B is a pictorial view and an enlargement view of the bone material removal device of FIGS. 5A-6B in a partially open configuration, according to some embodiments of the invention;

FIG. 9C is a pictorial view and an enlargement view of the bone material removal device of FIGS. 5A-6B in an expanded configuration, according to some embodiments of the invention;

FIGS. 15A-15B are two elevation views of a drill of a bone removal device similar to the bone removal device shown in FIGS. 5A-5B, constructed according to yet another embodiment of the present invention;

FIGS. 19A-19B are two elevation views and corresponding enlargements of an assembled bone removal device, showing the expandable tip in a closed configuration, according to some embodiments of the invention;

FIG. 19C is an elevation view, enlargement and a section view of the assembled bone removal device, showing the expandable tip in a closed configuration, according to some embodiments of the invention;

FIGS. 20A-20C are three different elevation views and corresponding enlargements of the assembled bone removal device, showing the expandable tip in an expanded configuration, according to some embodiments of the invention;

FIGS. 26A-26E show a cutting tooth from various directions, according to some embodiments of the invention;

DESCRIPTION OF SPECIFIC EMBODIMENTS OF THE INVENTION

Figure 2A:
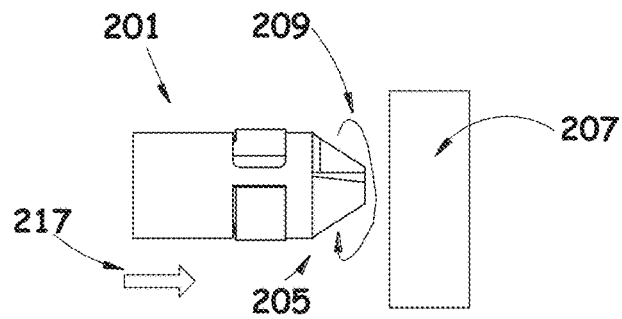
FIGS. 2A-2F are a set of drawing showing an exemplary method for drilling a bore in a bone, and widening at least a portion of the bore, according to some embodiments of the invention.

The present invention in some embodiments thereof, relates to a kit including a guiding system and a bone material removal device and method of use, for example, bone removal devices which change effective diameter. More particularly, the present invention relates to fixation devices for use in arthroscopic reconstruction procedures, particularly useful in Anterior Cruciate Ligament Reconstruction (ACL) procedures.

Overview

A broad aspect of some embodiments of the invention relates to a kit comprising a guiding system and a bone material removal device. In some embodiments, the guiding system comprises one or more reference structures for determination of the positions of one or two sides of a bone tunnel to be made in a bone (for example, a fibula and/or tibia), and/or relative lengths and/or positions of sections of the bone tunnel having different diameters. In some embodiments the reference structures are held relative to one another via a connecting member, which is optionally arcuate in form.

More particularly, lengths and/or positions of at least two tunnel portions are determined using reference structures, the portions comprising a proximal and narrower portion, and a wider, more distal portion. Optionally, the wider portion is between two narrower tunnel portions. In some embodiments, a narrower portion comprises a "bone bridge", which acts, for example, to provide stability to structures anchored in the tunnel, to allow greater freedom of tunnel placement, and/or to preserve greater strength in the tunneled bone itself.

In some embodiments, a first reference structure comprises a cannulated drill guide. Relevant reference portions of the cannulated drill guide comprise, for example, a cannula distal tip for positioning at a bone tunnel entrance side. In some embodiments, the tip is configured to be secured to the bone (for example, percussively driven into the bone). A cannula body extends from the cannula distal tip to attach to the connecting member. Scale marks and/or structures on this body are optionally used as reference points. In some embodiments, the cannula is slidably positionable relative to the connecting member along a longitudinal axis of the cannula, and/or in a radial direction relative to a curvature of the connecting member (for example, if the connecting member is arcuate). The cannula is sized to receive a bone material removal device (for example, a drill and/or reamer). More particularly, in some embodiments, the cannula is sized to receive a cannulated bone material removal device; more particularly still, in some embodiments, the bone material removal device comprises an expanding portion, such as an expanding cutting tooth.

In some embodiments, the cannulated bone material removal device is cannulated to receive a K-wire. Thus, in operation, the cannulated drill guide receives a cannulated bone material removal device, which in turn optionally receives in its own cannula a further item such as a K-wire or surgical wire.

In some embodiments, a second reference structure (a bone tunnel exit marker) comprises a hook, pointer, fork, or other terminal structure at the end of an arm which is connected at its base to the connecting member. Optionally, the base is slideable along a circumference defined by the connecting member (for example, when the connecting member is arcuate in form). Optionally, as the base slides, the second reference structure rotates around but remains substantially fixed in spatial translation relative to a reference position indicating a bone tunnel exit position.

Configuration of a three-part guiding system, in some embodiments, thus comprises determination of a guiding angle, set by the circumferential position along the connecting member (more particularly, along an arcuate connecting member) of the slideable arm, and determination of a bone tunnel length, set by the position of the distal tip of the cannula relative to the terminal structure of the arm.

Herein, it is to be understood that, unless otherwise expressly indicated, "distal" refers to a direction located generally away from an instrument operator and toward a patient, while "proximal" is generally closer to an instrument operator and away from a patient, when the instrument is in use. Furthermore, anterograde linear motion (such as drilling, for example) is generally proximal-to-distal in direction, while retrograde linear motion (such as counter-boring, for example), is generally distal-to-proximal in direction.

An aspect of some embodiments of the invention relates to a kit for formation of a bone tunnel, wherein at least a cannulated drill guide, and optionally a connecting element and arm are (for example, as outlined hereinabove) are provided as a guiding system together with a cannulated bone material removal device. In some embodiments, the cannulated bone material removal device comprises a cutting shaft for tunnel cutting (for example, drilling) at a first diameter, and an expandable distal portion for tunnel cutting (for example, reaming out a portion of the tunnel cut by the unexpanded shaft) at a second, larger diameter.

In U.S. Pat. No. 5,112,337, the cannula of a drill guiding system also comprising an arm and connecting element is used to position a K-wire as it is drilled through a tibia. The guiding system is then removed, and subsequent drilling is by cannulated drill over the K-wire. In a method of tunnel formation using the kit of the current invention, a K-wire and drill are advanced distally together through the tunnel; optionally, the drill alone is advanced. A potential advantage of this is reduction of the number of drilling passes into the bone that need to be performed. Moreover, it is a potential advantage for landmarks and/or distances defined by the guiding system to remain in place during drilling and/or reaming operations.

In some embodiments, further opening of a bone tunnel comprises reaming along a portion of the tunnel length with the expandable distal portion of the bone material removal device converted to its expanded state. Optionally, this is performed in a distal-to-proximal direction, stopping before reaching the proximal end of the tunnel. The resulting bone tunnel thus comprises at least two diameters—a narrower diameter at the proximal side, and a wider diameter leading out through the distal side. The narrower tunnel portion provides potential advantages for long-term strength and/or stability by maintaining greater bone thickness of the "bone bridge". It is a potential advantage for at least a portion of the guiding system to remain in place also during reaming, for example, for additional stability of positioning, to visualize distances, and/or to serve as a safety mechanism.

In some embodiments, the cannula of the guiding system is sized to fittingly enclose a portion of the drilling shaft and/or expandable distal end of the cannulated bone material removal device. The fitting inner diameter is sized to allow passage of the shaft of the bone material removal device, and/or of un-expanded distal portion thereof. The fitting sizing may be to within, for example, 0.025 mm, 0.05 mm, 0.1 mm, 0.15 mm, 0.2 mm, or another greater, smaller, or intermediate distance from the largest outer diameter of the bone material removal device portion which rotates inside of it, and/or of the largest bone material removal device portion which passes through it.

Optionally, the unexpanded distal portion of the bone material removal device is wider than the rest of the shaft, for example, by up to about 0.1 mm, 0.2 mm, 0.5 mm, or another greater, lesser, or intermediate amount. A shaft diameter is, for example, about 3 mm, 3.5 mm, 4.0 mm, 4.5 mm, 5.0 mm, or another larger, smaller or intermediate diameter. It is noted for reference that a typical K-wire (Kirschner wire) comprises a diameter in a range between about 0.711 mm and 1.575 mm.

The cannula of the guiding system is optionally used to position the bone material removal device at the beginning of and during a cutting phase of tunnel formation wherein cutting proceeds from a proximal to a distal direction through the bone. Optionally, encounter with the terminal structure of the arm indicates completed drilling, and/or limits the distal advance of the drill.

In some embodiments, a maximum withdrawal of the reamer (and thus, the proximal limit of the wider-diameter portion of the tunnel) is defined by the position of the distal tip of the guiding cannula, the lumen of which is narrower than the expanded diameter of the expanded distal portion, causing it to serve as a stop. Optionally, the distal tip is driven (for example, by rotation and/or percussively) into bone to a depth, for example, of about 7 mm. In some embodiments, the depth is larger or smaller, for example, about 5, 6, 8, 9, 10, or a greater, lesser, or intermediate value. In some embodiments, a widening at a shoulder portion of the distal tip limits and/or marks the depth to which the distal tip of the guiding cannula is driven into bone.

An aspect of some embodiments of the invention relates to the relationship of the terminal arm structure to the distal tip of the bone material removal device. In some embodiments, the distal tip of the bone material removal device encounters a tip of the terminal arm structure. In some embodiments, the terminal arm structure at least partially surrounds (for example, within the hollow of a hook- or fork-shaped structure) the distal tip of the bone material removal device where it exits bone. Optionally, at least partially surrounding comprises extending around at least 25%, 33%, 50%, or another larger, smaller, or intermediate fraction of a circumference of the bone material removal device.

Optionally, the hollow of the terminal arm structure is sized to allow the diameter of a K-wire to pass beyond it, but not the diameter of a portion of the cannulated drill shaft. Optionally, the hollow of the terminal arm structure is sized to allow the diameter of the unexpanded shaft (at least at its distal tip) to pass into and/or through it, but not the diameter of the expandable distal portion in its expanded configuration. In some embodiments, the guiding system sets the relationship of the guiding arm terminal structure to the guiding cannula and the bone such that a bone material removal device having an expandable distal portion can penetrate the bone. In some embodiments, the depth of penetration is such that the distal-most cutting portion of the expandable distal portion is assured to have reached the distal end of the bone tunnel (or another target distance), but prevented from passing so far distally that there is danger of damaging tissue (e.g., material of an adjacent bone) which it is not intended to cut.

In some embodiments, the hollow is large enough to allow passage of the expandable distal portion of the bone material removal device in the fully expanded position. It should be noted, particularly but not exclusively in relation to such embodiments, that an alternative means is optionally used to limit/mark advance of the shaft, for example, a pin and/or O-ring on a more proximal part of the device which interferes with longitudinal motion, for example, by interacting with the guiding cannula of the guiding system.

An aspect of some embodiments of the invention relates to the placement of scale markings for determination of tunnel and/or tunnel portion length. In some embodiments, a cannula is marked in relation to its longitudinal position in the arcuate member such that a shortest achievable bone-spanning distance $L2$ between cannula distal tip and arm terminal structure is marked by the indication of $L2$ on the cannula relative to some reference point on the arcuate member (that the indication is 4.5 cm or 45 mm if $L2$ is 4.5 cm, as 4.0 cm or 40 mm if $L2$ is 4.0 cm, etc.), with longer distances being indicated by progressively increasing values extending toward the distal end of the cannula. Optionally, the bone distance spanned is directly read from the cannula. Alternatively, a distance $L1$ increases from 0 (at the minimal-spanning position), to larger distances marked distally, which are added to a known or separately indicated value of $L2$ to get a total bone spanning distance $L3$, which is the length of the tunnel which is to be bored.

In some embodiments, a second scale is provided for determination of the position of the bone material removal device itself. In some embodiments, a distal-most point is marked by use of a rubber O-ring. For example, the O-ring placed on the shaft of the bone material removal device so that it prevents further advance by pressing against the guiding cannula. Optionally, the O-ring is set after reading off the measurement of the guide cannula when it is in position. Optionally, the marking of scales on the bone material removal device and the cannula is coordinated, so that the O-ring, placed on the same distance marker value of the bone material removal device shaft as is read from the position of the guiding cannula, will limit distal shaft travel just as drilling finishes clearing the tunnel; or, optionally, with just sufficient length added to this distance as to allow the expandable distal portion of the drill to engage with the distal end of the tunnel for subsequent reaming. For example, a distal-most drill position protrudes 5 mm from the bone tunnel itself. Then the offset of 5 mm is designed into the two scales, so that the correct offset will be provided.

Moreover, the combination of two scales, each readable relative to a component fixed to the bone, potentially allows more accurate and/or precise determination of positioning throughout tunnel formation, and/or predetermination of absolute or relative advance and/or retraction distances for the bone material removal device.

In some embodiments, one or two stoppers are placed on the guiding cannula itself, in positions where they interfere with the longitudinal motion of a portion of the bone material removal device to set its maximum distance of distal and/or proximal travel.

In some embodiments, a distal stopper sets a limit to anterograde travel of a bone material removal device, for example, a drill. This optionally helps to set a particular and/or a maximum travel of the drill, for example, to ensure full clearance of a bone tunnel, and/or to prevent drill contact with non-target tissue. In some embodiments, a proximal stopper sets a limit to retrograde travel of a bone material removal device, for example, a reamer. This optionally helps to set a particular and/or a minimum bone bridge thickness.

In some embodiments, the interfered-with portion of the bone material removal device is longitudinally locked to the shaft, but rotationally free. This potentially serves to limit movement by interactions with one or more longitudinally fixed elements of guiding system, while still allowing the shaft to rotate. For example, the portion comprises a pin protruding from a bearing ring. Additionally or alternatively, a bearing ring on the shaft comprises one or more grooves, into which a portion fixed to the guide cannula inserts to block and/or resist movement outside of a certain range. Optionally, the one or more grooves are laterally asymmetric (for example, sawtooth shaped) so that they can be freely moved out of in one direction only. Optionally, two grooves are oppositely oriented, and positioned such that one limits movement distally, and one limits movement proximally. Optionally, the range of limited movement is set by stoppers/sliders which interact with the grooves, optionally movable along the body of the guide cannula.

An aspect of some embodiments of the invention relates to a bone material removal device comprising a shaft with an expandable distal portion. In some embodiments, the expandable distal portion comprises one or more bone removing elements, for example cutting or reaming teeth. In some embodiments, the device is adapted to operate in one of two operational configurations, for example one for drilling and/or passing through a bore in a bone, and the other for widening a bore in a bone. In some embodiments, the first configuration comprises cutting teeth at a closed configuration, such as contained within a shaft of the device. In some embodiments, the second configuration comprises cutting teeth at an open configuration, for example extending beyond the circumference of the shaft.

An aspect of some embodiments relates to a bone material removal device comprising a cutting tooth which is only partially received within a recess of a shaft of the device when the tooth is in the closed position.

In some embodiments, the tooth extends beyond a periphery of the device, for example beyond a periphery of a shaft portion configured directly above and/or below the recess in which the tooth is received. In some embodiments, a least a section of the shaft defines a generally cylindrical volume of rotation, and at least a portion of the closed tooth extends beyond the volume of rotation. In some cases, a diameter of a bore formed using the device is defined by an extent in which the tooth protrudes externally to the shaft of the device.

In some embodiments, the tooth is moved to an open position by utilizing resistance of the walls of the bore acting on the protruding portion of the tooth. Optionally, pivoting of the tooth is actuated by reversal of rotation direction of the device, creating friction between the protruding portion of the tooth and the walls of the bore. Alternatively, for example in cases in which the device is inserted into a pre-formed bore in the bone, simply rotating the device (such as without reversing a direction of rotation) would open the tooth.

Additionally or alternatively, in some embodiments, the tooth is advanced passed the bore to exit the bone, and pivoting of the tooth is actuated by reversal of rotation direction, utilizing centrifugal force to open the tooth.

In some embodiments, the recess in the shaft, in which a portion of the tooth is received, is shaped and/or sized to limit movement of the tooth, such as rotational movement, for example preventing over-opening and/or over-closing the tooth. Additionally or alternatively, a hinge by which the tooth is coupled to device is configured for limiting movement of the tooth, for example by comprising one or more transversely extending projections.

In some embodiments, the hinge is a rod hinge, comprising elongated proximal and/or distal extensions that are received within a shaft of the device. A potential advantage of a hinge comprising elongated extensions may include reducing a risk of disengagement of the hinge from a shaft of the device.

An aspect of some embodiments relates to a bone cutting tooth comprising a cutting face formed with a curvature. In some embodiments, at least a portion of the cutting face is concave. Additionally or alternatively, a portion of the cutting face is planar.

In some embodiments, a curved cutting surface such as a concave cutting surface is effective to distribute force applied onto the cutting face by the bone tissue that is being cut. Optionally, the concavity is non-symmetrical, for example along a height of the tooth. Alternatively, the concavity is symmetrical. In some cases, the concavity of the cutting face acts as flute, providing a path for removal of the removed bone material, including, for example, bone chips and/or dust. In some cases, removed bone material flows towards a center of the concavity, and then flows in the proximal and/or distal directions over the top and/or bottom surfaces of the cutting tooth. In some cases, removed bone material exits through a first and/or second openings of the formed bore. Additionally or alternatively, removed bone material is swept by the cutting face towards the walls of the bore.

In some embodiments, a bottom surface of the cutting tooth facing a generally proximal direction is formed with a curvature and/or an inclination, for engaging an irregular bone surface, for example before the opened cutting tooth is pulled back through the bore to widen at least a portion of the bore.

In some embodiments, a back wall of the tooth, such as a generally opposite wall to the cutting face, comprises a rounded geometry so that it is at least partially flushed with the shaft when the tooth is in a closed configuration. In some embodiments, the back wall is curved, and does not inflict resistance to rotation of the shaft when the tooth is closed, for example by smoothly sliding across the walls of the bore during rotation of the shaft.

In some embodiments, the tooth is rigid. In some embodiments, the tooth is elastic enough so that the protruding portion of the tooth is pushed into the recess in the shaft during formation of the bore. Optionally, when the rotation direction changes, the protruding portion immediately bounces out of the shaft, contacting the walls of the bore which thereby initialize the opening of the tooth. Optionally, the tooth continues to pivot to a fully open configuration as rotation continues and increasing resistance is applied to the tooth by the walls of the bore.

In some embodiments, a portion of the tooth, such as a cutting surface of the tooth, is formed of a rigid material. Additionally or alternatively, a portion of the tooth, for example a back wall, is formed of a flexible material.

In some embodiments, the cutting tooth comprises one or more slots or channels, for example the cutting face may be formed with a radially extending slot, through which removed bone material can pass to be cleared away from tooth.

In some embodiments, the cutting teeth extend from the distal tip, for example extending substantially perpendicularly to the longitudinal axis of the device. Optionally, a cutting tooth pivots to an open position, in which it extends radially away from the device. In some embodiments, expanding the distal portion includes enlarging a radius of the bone engaging portion of the device. In some embodiments, the device includes a forward drill bit.

In an exemplary embodiment of the invention, the bone removal elements are attached to the shaft freely enough so that rotation of the shaft at sufficient speed would cause them to extend radially outwards from a position they are in, for example from a position in which the elements are flush with the shaft or a position in which the elements are recessed from the shaft. In an exemplary embodiment, the shaft includes a stop which prevents over extension of the elements, for example, limiting the rotation of the elements around a hinge which attaches them to the shaft to an angle ranging between, for example, 50, 70, 80, 90, 100 or smaller or intermediate or greater number degrees.

In some embodiments, a stopping element is configured to restrict entry of a cutting element further into the shaft, for example when the cutting element is in a closed position. In some embodiments, the stopping element comprises one or more walls of a recess in the shaft in which the bone removal element is received. In some embodiments, the stopping element is the cutting element itself, for example being formed with a portion large enough to prevent the cutting element from fully entering the shaft. In an example, a radial extent of a cutting element is larger than that of the shaft, preventing from the complete cutting element to be fully contained within the shaft. In some embodiments, the stopping element comprises an elastic element such as a spring coupled to the tooth and/or the shaft, which allows for the cutting element to be pushed into the shaft. Optionally, the spring provides for the cutting element to bounce open, for example to form contact between the cutting element and the walls of the bore in the bone. Optionally, friction is created between the cutting element and the walls, actuating initial opening or further opening of the tooth.

In some embodiments, the operational configuration is selected by a user. In some embodiments, changing the direction of rotation causes the cutting teeth to extend, such as by pivoting to an open position, or alternatively to fold back into a closed configuration. For example, this may be provided by the relative locations of a center of gravity of the tooth and a hinge (e.g. an axial pin) connecting the tooth to the shaft. In some embodiments, centrifugal force created during the rotation of the device thrusts the cutting teeth outwardly from the shaft of the device.

In some embodiments, rotation causes extension, obtained for example by pivoting of a tooth with respect to a shaft of the device, until reaching a stop. However, the teeth may be free to move back to a previous position. In such a case, the extension (such as by pivoting) of the teeth will depend on the direction of rotation and existence of nearby objects, such as bone, to contact the teeth. Rotation in a first direction will cause the teeth to engage the bone, and the stop will prevent the teeth from moving out of the way, ultimately resulting in bone removal. A rotation in opposite direction allows the tooth to retreat from the force applied by the bone, and possibly fold back to become flush with the shaft.

In some embodiments, the device can be seen as having two behaviors, depending on the drilling direction. In one drilling direction, contact of extended teeth with objects such as bone will tend to close the teeth, and in the other drilling behavior the teeth, when contacting bone, will tend to remain in an extended position and remove bone material.

In some embodiments, an initial bore is drilled in a bone. In some embodiments, after the initial bore is drilled, the device is used for widening at least a portion of the bore. In some embodiments, by reversing the direction of rotation of the device, the cutting teeth are pushed outward. In one example, when the device is rotated in a clockwise direction the cutting teeth are maintained within the circumference of the shaft of the device, and when the device is rotated in a counterclockwise direction the teeth extend outwardly from the shaft. Optionally, the centrifugal force created once the direction of rotation is reversed is strong enough to thrust the cutting teeth outwards.

In some embodiments, the shaft of the device comprises a flexible portion, for example comprising a spring.

An aspect of some embodiments relates to a bone material removal kit, comprising a device for example as described herein, and a plurality of replaceable cutting teeth. In some embodiments, the cutting teeth include a first tooth which is only partially received within a shaft of the device, and a second tooth which is fully received within a shaft of the device. In some embodiments, at least a portion of the first tooth, in a closed position, contacts walls of the bore in the bone, to provide for friction based opening of the tooth when the device is inside a bore in the bone. In some embodiments, the second tooth is moved to an open configuration as a result of rotation, for example due to centrifugal force. Optionally, a user selects the first tooth when opening of the tooth inside the bore is desired, and selects the second tooth when opening of the tooth outside the bore is desired. In some embodiments, the tooth is configured as a part of a unit, for example including a shaft segment which can be assembled onto the device.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Reference is now made to FIGS. 1A-1B, which show a bone material removal device comprising an expandable distal portion 103, according to some embodiments of the invention. An enlarged view of distal portion 103 of FIG. 1A and of FIG. 1B is shown under each.

In some embodiments, the device comprises a distal tip 105, a shaft 107, and a proximal end 109.

In some embodiments, a distal portion 103 of the device comprises a plurality of bone removal elements such as cutting teeth 111, for example 1, 2, 5, 8 or any larger or intermediate numbers. In some embodiments, the cutting teeth 111 extend from shaft 107 of the device. In some embodiments, as will be further explained, centrifugal force caused by rotation of the device acts on the cutting teeth to extend them.

In some embodiments, the device is adapted to two operational configurations. In the first configuration, shown in FIG. 1A, the cutting teeth remain in a closed configuration, for example contained within a circumference of the shaft. In the second mode, shown in FIG. 1B, the cutting teeth extend externally from the shaft to an open configuration, for example extending beyond the circumference of the shaft. In some embodiments, the drilling direction is compatible with the closed configuration. In some embodiments, the drilling direction is compatible a configuration in which the teeth, once open, will close rather than stay open.

In some embodiments, the first operational configuration shown in FIG. 1A is used for drilling a bore in a bone. Optionally, drilling is performed by attaching proximal end 109 of the device to a drill motor (not shown). In some embodiments, the first configuration is used for passing the device through an existing bore, possibly without rotation. Optionally, a spring element (e.g. between teeth 111 and shaft 107) or a coupling material (e.g. a coating on the elements) is provided to apply a small force to maintain teeth 111 in conformance with the surface of shaft 107.

In some embodiments, in the first operational configuration, cutting teeth 111 are contained within the shaft. In some embodiments, the cutting teeth are positioned at the shaft's circumference. Optionally, in the closed configuration, the cutting teeth do not extend beyond the largest diameter of the shaft. Alternatively, in the closed configuration, the cutting teeth extend beyond the diameter of the shaft.

In some embodiments, the second operational configuration shown in FIG. 1B is used for widening at least a portion of a bore in a bone. In some embodiments, the cutting teeth 111 extend externally from the shaft 107, for example extending perpendicularly to a main axis of the shaft. In some embodiments, when cutting teeth 111 are extended to an open configuration, they increase a diameter of at least one section of the distal portion 103, for example distal tip 105, for example by 20%, 70%, 90% and/or smaller, greater, or intermediate numbers.

In some embodiments, a user may selectively choose the operational configuration, for example by choosing the direction of rotation of the device. In some embodiments, when rotating in one direction, for example in a clockwise direction, the cutting teeth 111 remain adjacent to the shaft in a closed configuration. Additionally and/or alternatively, when rotating in the opposite direction, such as a counter-clockwise direction, centrifugal force causes the cutting teeth 111 to extend beyond the shaft's circumference.

In some embodiments, the rotation always causes extension of the teeth, but the rotational direction decides if the teeth will tend to remain open or close, when contacting an object.

Some embodiments comprise cutting teeth 111 having various shapes and/or sizes of cutting edges, for example a cutting edge having a rectangular cross section, a circular cross section, or a triangular cross section. In some embodiments, cutting teeth are shaped as an arc. Optionally, the length of the arc is a half of the circumference of the shaft. In one example, two arc shaped cutting teeth complete the shaft's circumference. In some embodiments, the arc has a thickness, in an axial and/or radial direction, for example a thickness of 0.2 mm, 0.4 mm, 2 mm, or any smaller, intermediate or larger thicknesses. In some embodiments, the cutting teeth 111 are formed with an eroding exterior, for example to file the bore during widening.

In some embodiments, a cutting tooth 111 is connected to the shaft 107, for example connected using a hinge or a pivot. In some embodiments, the connection area includes a geometry which inhibits free motion of the cutting tooth 111, for example allowing the cutting tooth to extend and open only in one direction. In some embodiments, the degree of pivoting is manufactured according to a need, for example limiting a cutting tooth to open at 30 degrees, 60 degrees, 90 degrees or any intermediate or smaller numbers with respect to the axis of pivoting.

In some embodiments, a section such as shown alongside recess 115 in the enlarged version of distal portion 103 in FIG. 1B prevents cutting tooth 111 from over opening, for example opening in angle larger than 180 degrees.

In some embodiments, shaft 107 comprises a recess 115. Optionally, recess 115 receives a cutting tooth 111, for example when the device is in a closed configuration.

In some embodiments, different teeth have different lengths. In some embodiments, different teeth have different axial positions. For example, one cutting tooth may extend to a length equal to half the circumference of the shaft, while a second cutting tooth may extend to a length that is a quarter of the circumference of the shaft.

In some embodiments, the shape of the cutting teeth and/or the size of their cutting edges and/or faces is selected to create a certain pattern of the widening of the bore.

In some embodiments, the cutting teeth extend in an individual manner, for example each cutting tooth extends independently of another. Alternatively, the cutting teeth may be manufactured so that opening of one tooth to an extended configuration leads to the opening of another tooth, for example by pushing an adjacent tooth.

In some embodiments, cutting teeth may be spring loaded, for example to open or close them.

In some embodiments, the device is a drill. In some embodiments, the device is a reamer.

In some embodiments, the distal tip is a drill bit. Optionally, the distal tip comprises a threaded portion. In some embodiments, the proximal end is shaped to engage a drill, for example having a hexagonal shape.

In some embodiments, the device is cannulated, for example to be inserted over a guiding wire.

In some embodiments, the device comprises a plurality of depth indicating markings.

In some embodiments, the device is made of stainless still, such as Eagle Stainless Steel. In some embodiments, the cutting teeth 111 are made of the same material as the rest of the device, or made of a different material.

Reference is now made to FIGS. 2A-2D, which show an exemplary method for drilling a bore in a bone, and widening at least a portion of the bore, according to some embodiments of the invention. Further reference is made to FIGS. 2E-2F, which are enlarged views of a distal tip of the device during the stages described at FIGS. 2A-2B and FIGS. 2C-2D respectively.

In some embodiments, device 201 is used for drilling a bore in bone. In some embodiments, as shown in FIG. 2A, one or more cutting teeth 203 are in a closed configuration. In some embodiments, a distal tip 205 of the device is inserted into a bone 207. In some embodiments, distal tip 205 is a drill bit, optionally having a threaded portion. In some embodiments, during insertion into the bone in a direction shown by arrow 217, device 201 is rotated, for example by being connected to a drill, in a direction such as direction 209.

Figure 2B:
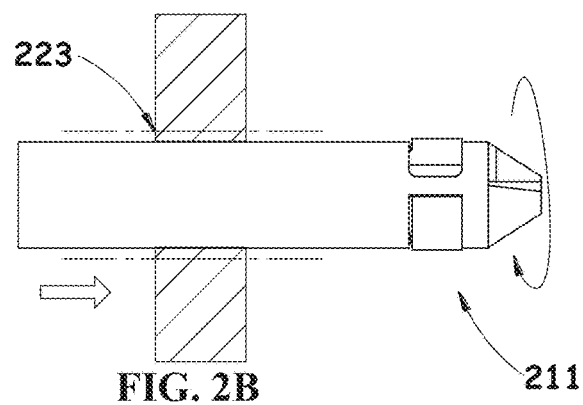

In some embodiments, as shown in FIG. 2B, the device drills through bone 207 to create a bore 223 (marked by the dotted line) extending between opposite sides of the bone. In some embodiments, a distal portion of the device 211 extends beyond bone 207.

In some embodiments, bone 207 prevents cutting teeth 203 from extending. Additionally and/or alternatively, bone 207 forces cutting teeth 203 back to a closed configuration.

Figure 2C:
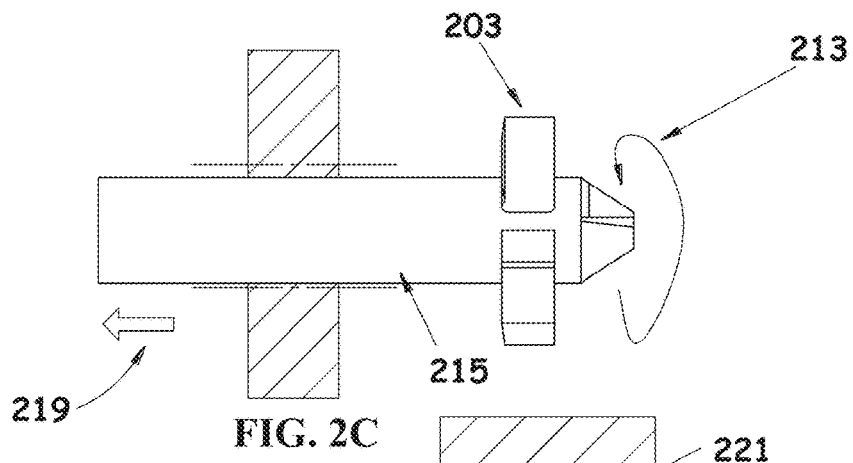

In some embodiments, as shown in FIG. 2C, once a bore has been drilled, cutting teeth 203 are forced to extend externally to shaft 215. In some embodiments, by reversing the direction of rotation to an opposite direction 213, the centrifugal force created acts on cutting teeth 203 so that they extend outwardly from the shaft, such as by pivoting on a hinge. In some embodiments, at this point, the device is pulled (for example using the drill) backwards, such as back into the drilled bore, in the direction shown by arrow 219.

Figure 2D:
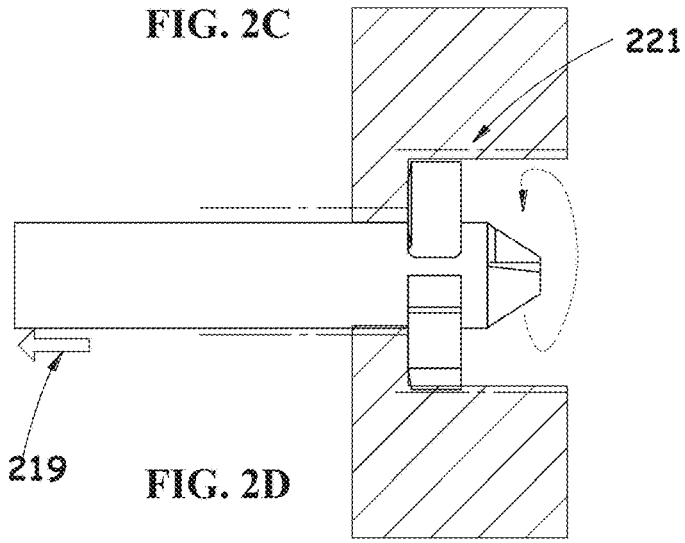

In some embodiments, as shown in FIG. 2D, the reversed direction of rotation retains the cutting teeth 203 in their open configuration. In some embodiments, as the device is pulled backwards through the existing bore, cutting teeth 213 widen a diameter of the bore, as shown in bore portion 221. In some embodiments, cutting teeth remove bone material by cutting and/or crumbling the bone tissue. In some embodiments, the initial diameter of the bore is widened by 10%, 50%, 90% and or intermediate and/or larger values.

In some embodiments, the cutting teeth 203 remain in their open configuration due to opposite forces exerted by the walls of the bore, for example if the bore is narrow.

In some embodiments, only a portion of the bore is widened. Optionally, the widening of a portion of the bore forms a location to anchor, for example, an ACL or any other ligament or object which may be pulled against a narrow part of the borrow.

In some embodiments, the direction of rotation is reversed again, for example half way through the bore, causing cutting teeth 203 to return to their closed configuration inside the shaft. In some embodiments, a face and/or edge of the cutting tooth is curved, so that contact with the bore applies a radial closing force on the cutting tooth.

In some embodiments, the device is then pulled back through the remaining portion of the bore, optionally without widening it.

In some embodiments, for example if a bore already exists in bone 207, the device may be used to only widen the existing bore, for example by being inserted in a closed configuration through the bore, and pulled back up in an open configuration so that the cutting teeth cut along at least a portion of the existing bore to widen it upon rotation.

Figure 2F:
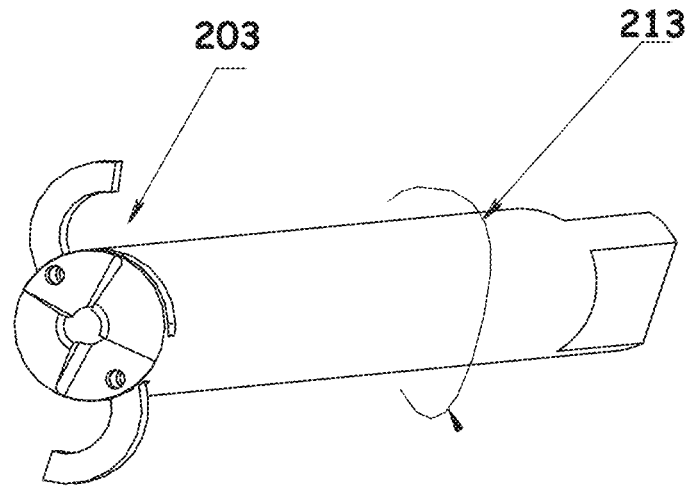
Figure 2E:
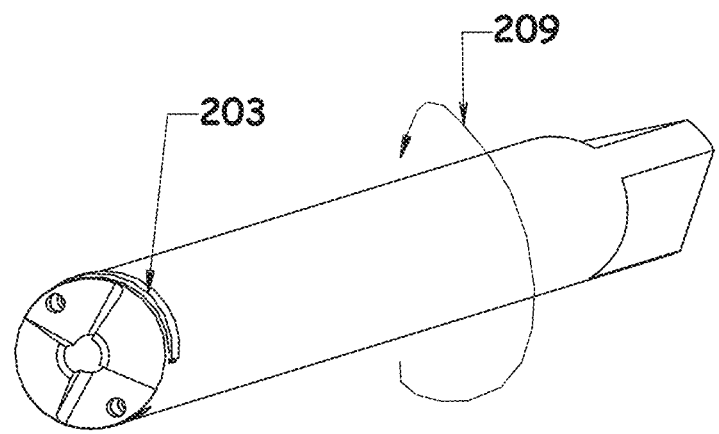

The enlarged view in FIG. 2E shows the cutting teeth 203 in closed configuration. Optionally, the device is rotated in the first direction 209.

The enlarged view in FIG. 2F shows the cutting teeth 203 in an open configuration. Optionally, the device is rotated in the second direction 213.

Figure 3:
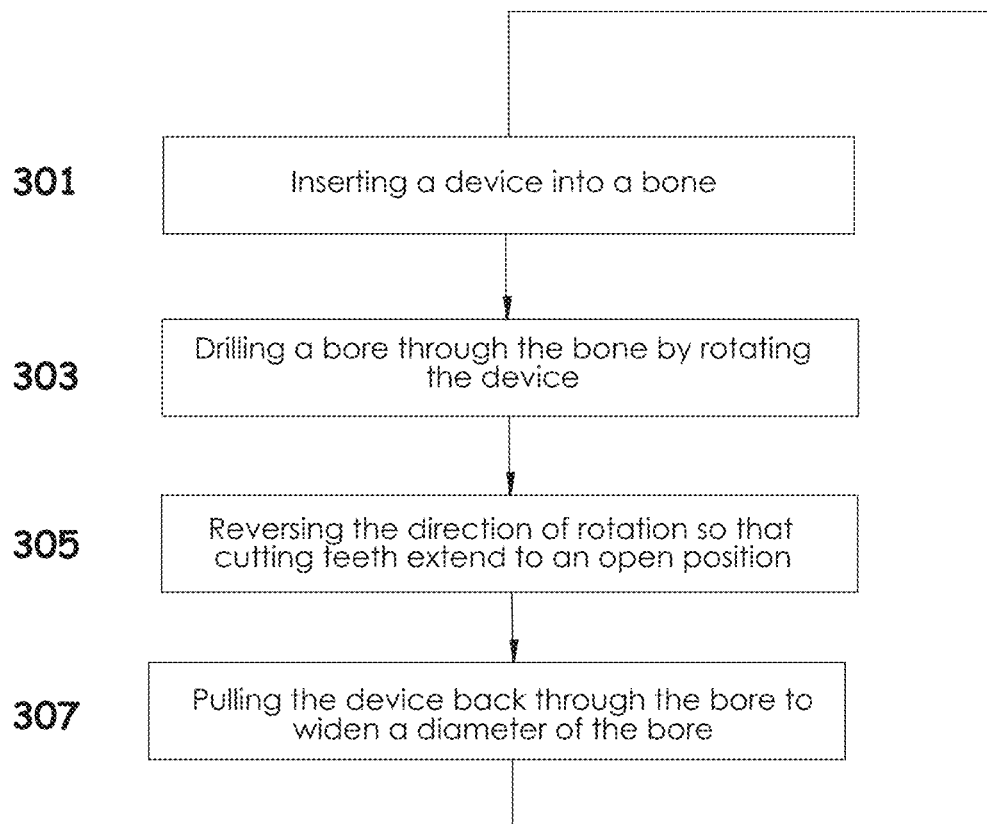
FIG. 3 is a flowchart of an exemplary method for drilling a bore in bone, and widening at least a portion of the bore, according to some embodiments of the invention.

Reference is now made to FIG. 3, which is a flowchart of an exemplary method for drilling a bore in bone, and widening at least a portion of the bore, according to some embodiments of the invention. In some embodiments, a device is inserted into the bone 301. In some embodiments, a bore is drilled through the bone using the device 303, for example by rotation of the device. Alternatively, as previously mentioned, the device passes through an existing bore in a bone, for example a bore previously created using a drill or any other means for forming a bore.

In some embodiments, the bore is drilled through a portion of the bone, for example extending to a certain depth within the bone, such as 2 mm, 9 mm, 5 cm, 7 cm and/or any smaller, intermediate or larger depths. In some embodiments, the drilled bore extends between two opposite faces of the bone.

In some embodiments, a distal portion of the device extends beyond an exit aperture of the bore. In some embodiments, this positioning allows the distal portion to be located in a large enough lumen for allowing the cutting teeth to extend into an open configuration. Optionally, a large enough lumen exists in a different location, for example a naturally formed lumen within the bone.

In some embodiments, extension of the cutting teeth is achieved by rotation of the device, for example rotation in an opposite direction to the direction of rotation during drilling of the bore 305. Optionally, a centrifugal force created during rotation is strong enough to thrust the cutting teeth into an open configuration.

In some embodiments, once the cutting teeth are in their open extended configuration, the device may be pulled back though the bore. In some embodiments, the cutting teeth widen the bore as the device is pulled back. Optionally, the rotation speed affects cutting effect of the teeth.

In some embodiments, the device widens a diameter of at least a portion of the bore 307, for example widens a third of the length bore, a half of the length of the bore, or the full length of the bore. In some embodiments, a diameter of the bore may increase by 10%, 50%, 90% and/or intermediate or larger values.

In some embodiments, a user selectively decides not to extend the cutting teeth, for example to avoid widening the bore. Optionally, the device is pulled back through the bore having the teeth in a closed configuration.

Figure 4:
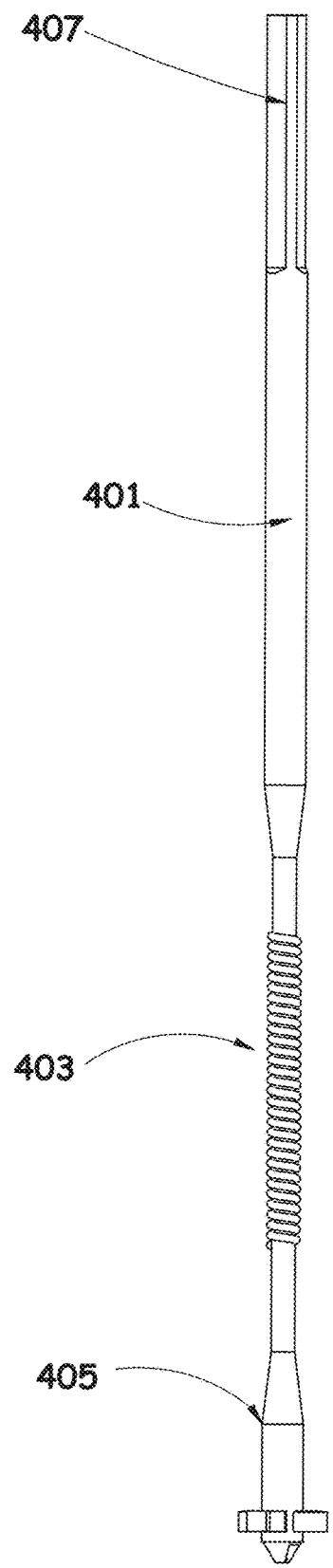
FIG. 4 is a bone removal device comprising an expandable distal tip and a shaft comprising a flexible portion, according to some embodiments of the invention.

Reference is now made to FIG. 4, which shows an expandable bone removal device having a shaft with a flexible portion, according to some embodiments of the invention. In some embodiments, shaft 401 comprises a flexible portion 403, extending for example between a distal tip 405 and a proximal end 407, or a segment of that portion.

In some embodiments, flexible portion 403 comprises a spring. Optionally, the spring transmits torque during rotation of the device to distal tip 405.

In some embodiments, distal tip 405 comprises an expandable portion such as cutting teeth. In some embodiments, distal tip 405 does not comprise an expandable portion. Optionally, distal tip 405 is a drill bit.

In some embodiments, flexible portion 403 enables bending of the device, for example allowing drilling in bone locations that cannot be approached directly. In some embodiments, for example if the device is bended, a curved bore may be formed. In some embodiments, the device is inserted over a guide wire.

In some embodiments, flexible portion 403 has the same diameter as the rest of shaft 401. In some embodiments, flexible portion 403 has a smaller diameter than the diameter of shaft 401.

In some embodiments, the spring comprising flexible portion 403 is attached to shaft 401 during manufacturing using laser welding techniques and/or other techniques suitable for coupling the spring to the shaft.

Reference is now made to FIGS. 5A-6B, which show a bone material removal device 500 constructed according to another embodiment of the present invention, including an expandable distal portion 502, showing the expandable portion 502 in a closed configuration.

It is seen that the bone material removal device 500 includes a distal tip 504, a longitudinal shaft 506 and a proximal end 508.

The distal portion 502 of the bone material removal device 500 preferably includes a single cutting tooth 510. It is appreciated that the distal portion 502 may include a plurality of cutting teeth 510.

It is a particular feature of some embodiments of the present invention that the cutting tooth 510 extends from the outer circumference of the shaft 506 both in closed configuration and in open configuration, as seen in FIGS. 5A-5B and FIGS. 6A-6B.

In an exemplary embodiment of the present invention, centrifugal force and friction force between the cutting tooth 510 and a portion of the bone cause the expandable portion 502 to open and thus the cutting tooth 510 extends further from the longitudinal shaft 506, as will be described in detail below.

The device is adapted for two operational configurations.

The first configuration is shown in FIGS. 5A-5B, where the cutting tooth 510 remains in a closed configuration, such that only a small portion of cutting tooth 510 extends out of the outer circumference of the longitudinal shaft 506. In an exemplary embodiment of the present invention, the cutting tooth 510 extends approximately 0.1 mm from the outer circumference of the shaft 506.

The second configuration is shown in FIGS. 6A-6B, where the cutting tooth 510 extends externally from the outer circumference of the shaft 506 to a greater extent, assuming an open configuration of the bone material removal device 500.

The first operational configuration shown in FIGS. 5A-5B is typically used for drilling a bore in a bone. Optionally, drilling is performed by attaching proximal end 508 of the device 500 to a drill (not shown). In some embodiments, the first configuration is used for inserting the device 500 into an existing bore, possibly without rotation. According to an exemplary embodiment of the invention shown in FIGS. 5A-5B, in the first operational configuration, cutting tooth 510 slightly extends from the outer circumference of the shaft 506.

According to an exemplary embodiment of the invention shown in FIGS. 6A-6B, the second operational configuration is used for widening at least a portion of a bore in a bone. In some embodiments, the cutting tooth 510 extends externally from the outer circumference of the shaft 506, for example extending perpendicularly to a main axis of the shaft to a greater extent than in the first operational configuration shown in FIGS. 5A-5B. In some embodiments, when cutting tooth 510 is extended to an open configuration, it increases a diameter of at least one section of the distal portion 502, for example distal tip 504, for example by 20%, 70%, 90% and/or any smaller, greater, or intermediate numbers.

A user may selectively choose the operational configuration, for example by choosing the direction of rotation of the bone material removal device 500. In some embodiments, when rotating in one direction, for example in a clockwise direction, the cutting tooth 510 remains adjacent to the shaft 506 and slightly extending therefrom in a closed configuration. Additionally and/or alternatively, when rotating in the opposite direction, such as a counterclockwise direction, frictional force formed between the bone portion and the portion of the cutting tooth 510 which extends beyond the circumference of the shaft 506 and centrifugal force cause the cutting tooth 510 to extend to a greater extent beyond the circumference of the shaft 506.

Reference is now made to FIGS. 7A-7B, which show the drill of the bone material removal device 500 constructed in accordance to an exemplary embodiment of the present invention, consisting of a longitudinal shaft 506 having a proximal end 508, distal tip 504 and a recess 512 for insertion of a cutting tooth 510 therein. In some embodiments, distal tip 504 is a drill bit, optionally having a threaded portion.

It is seen in FIGS. 7A-7B that the drill is cannulated, including a longitudinal bore 514 extending from the distal end 508 to the proximal tip 504 for flushing or removal of residual drilling materials.

Reference is now made to FIGS. 8A-8D, which illustrate an exemplary design of a cutting tooth 510 insertable into recess 512 of the drill of the bone material removal device 500.

Reference is now made to FIGS. 9A-9C, showing the bone material removal device 500 in a closed configuration, a partially open configuration and an expanded open configuration respectively.

It is seen in FIG. 9A that the cutting tooth 510 slightly extends beyond the outer circumference of the shaft 506, when the cutting tooth 510 is in the closed configuration.

It is seen in FIG. 9B that the cutting tooth 510 extends further beyond the outer circumference of the shaft 506 as the cutting tooth partially opens.

It is further seen in FIG. 9C that the cutting tooth 510 maximally extends beyond the outer circumference of the shaft 506, when the cutting tooth 510 is in the open configuration.

Figure 10B:
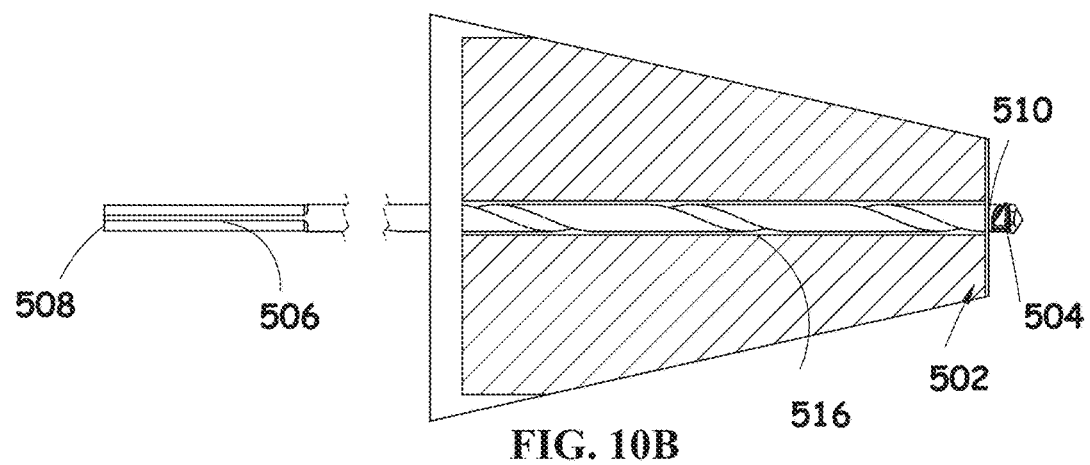
FIGS. 10A-10C are a pictorial view, two sectional views and an enlargement view of the bone material removal device of FIGS. 5A-6B in a closed configuration, shown within a bone portion after a bore of a first diameter was drilled through the bone portion, according to some embodiments of the invention.
Figure 10A:
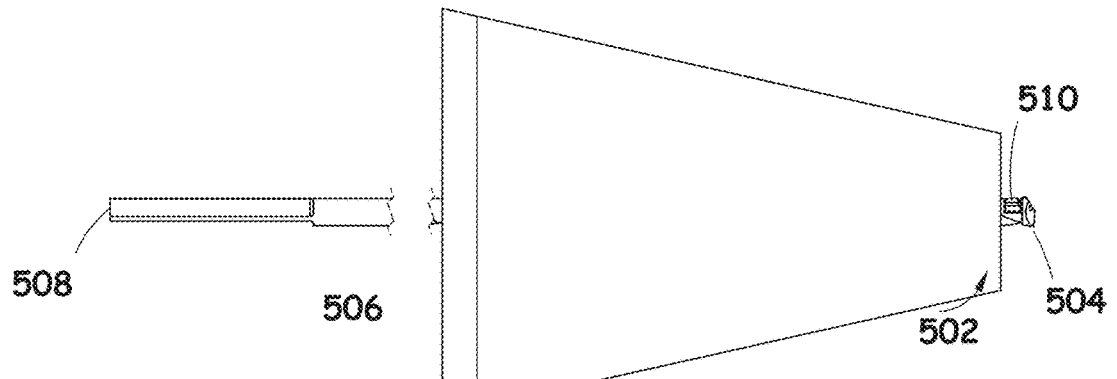
Figure 10C:
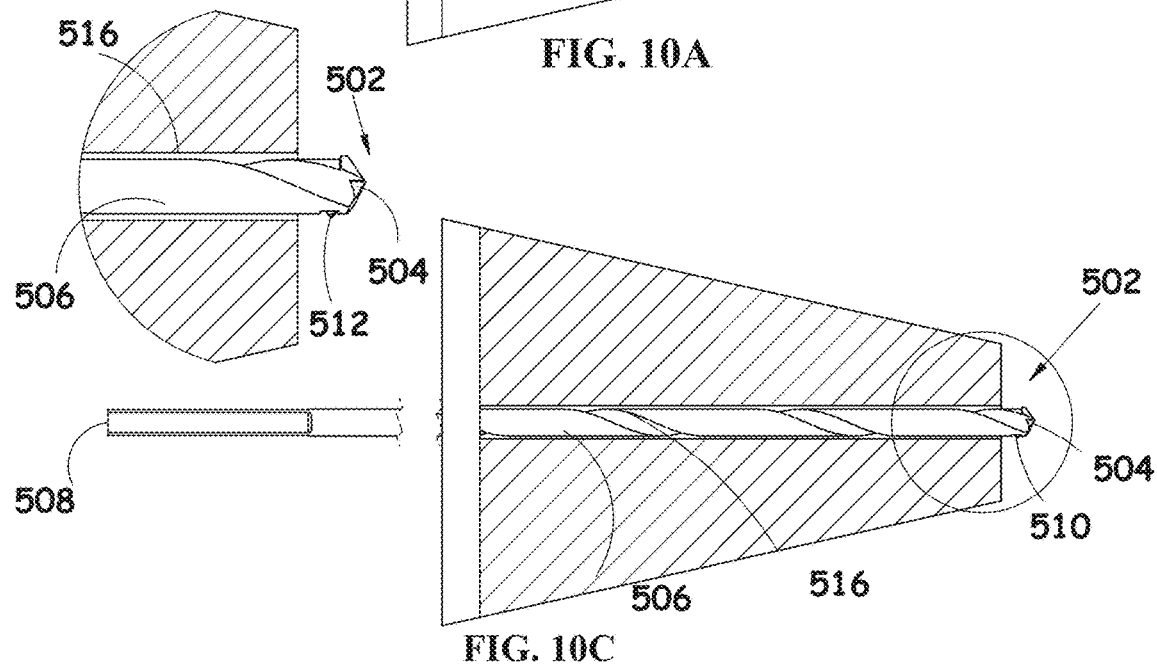

Reference is further made to FIGS. 10A-10C, showing the bone material removal device in a closed configuration, shown within a bone portion when a bore of a first diameter was drilled through the bone portion.

It is seen in FIGS. 10A-10C that the drill of the bone material removal device 500 is used in a closed configuration for providing a bore of a first diameter 516 within a bone portion by inserting the distal tip 504 into the bone portion and rotating the device 500, for example by connection to a drill, drilling through the entire bone portion until the expanding portion 502 extends out of the bone portion and the cutting tooth 510 is either positioned distally of the bone portion or abuts the bone portion.

The drill is rotated preferably in a clockwise direction, keeping the cutting tooth 510 in a closed configuration, such that the cutting tooth 510 slightly extends beyond the circumference of the shaft 506.

Figure 11B:
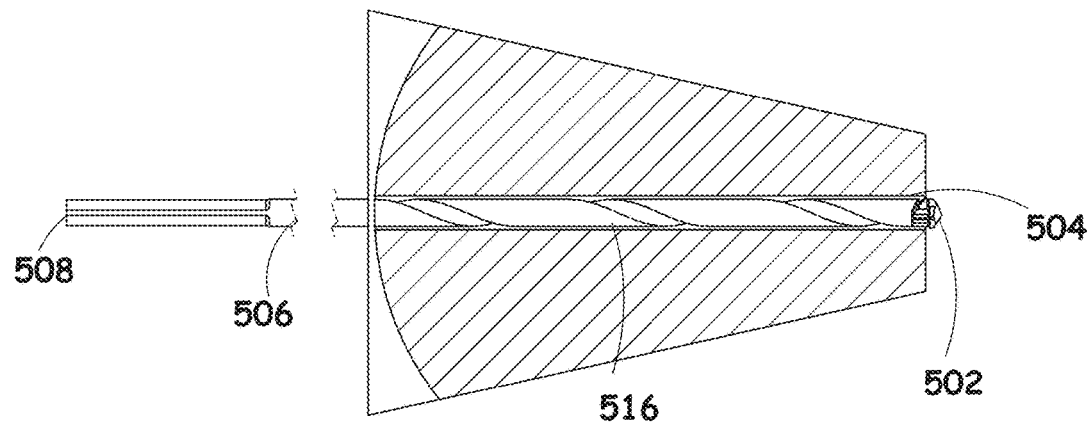
FIGS. 11A-11C are a pictorial view and two sectional views of the bone material removal device of FIGS. 5A-6B in an expanded configuration, shown within a bone portion after a bore of a first diameter was drilled through the bone portion, according to some embodiments of the invention.
Figure 11A:
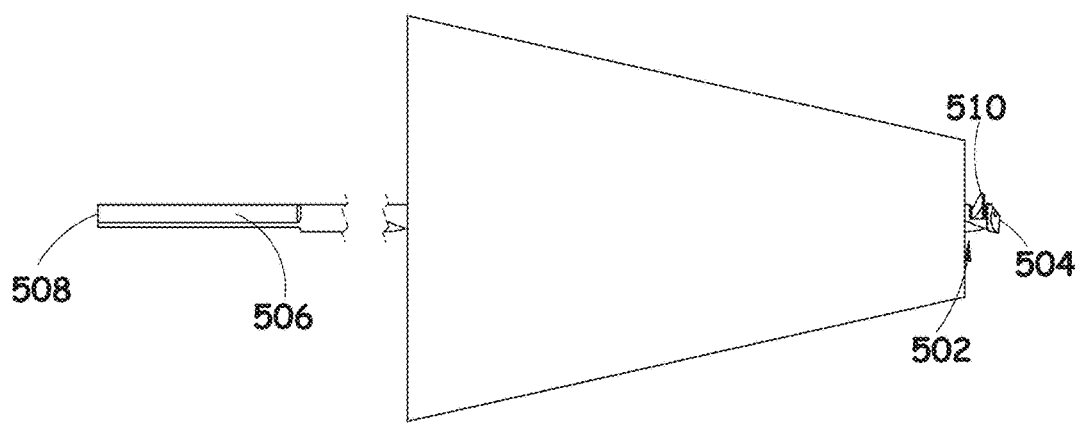
Figure 11C:
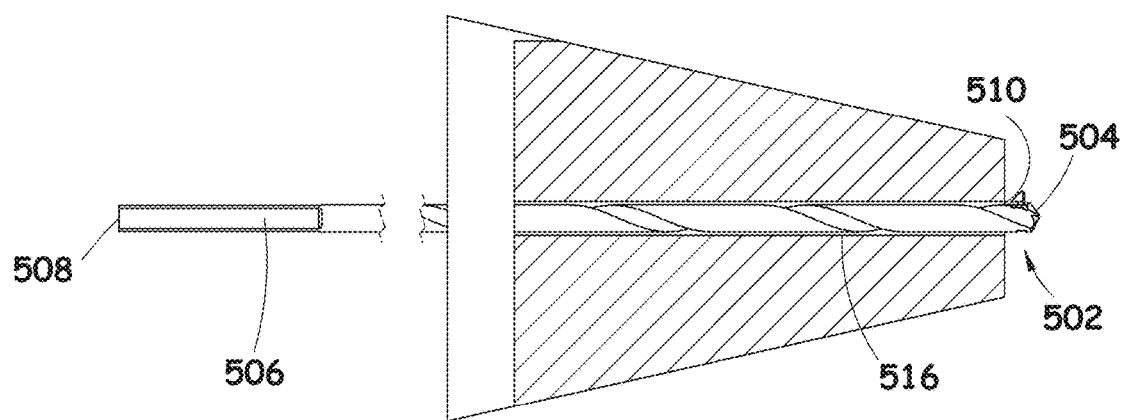

Reference is now made to FIGS. 11A-11C, showing the bone material removal device 500 in an expanded configuration, shown partially within a bone portion when a bore of a first diameter was drilled through the bone portion.

It is seen in FIGS. 11A-11C that the drill of the bone material removal device 500 is used in an expanded configuration for providing a bore of a second diameter 518, preferably greater than the first diameter, by reversing the rotation direction of the drill and drilling in an opposite axial direction through a portion of the bore of the first diameter to provide a widened bore portion.

It is appreciated that the frictional forces which appear between the cutting tooth 510 and the bone portion and centrifugal forces caused by reversing direction of rotation of the drill provide for the cutting tooth 510 to expand and assume an open configuration.

Figure 12A:
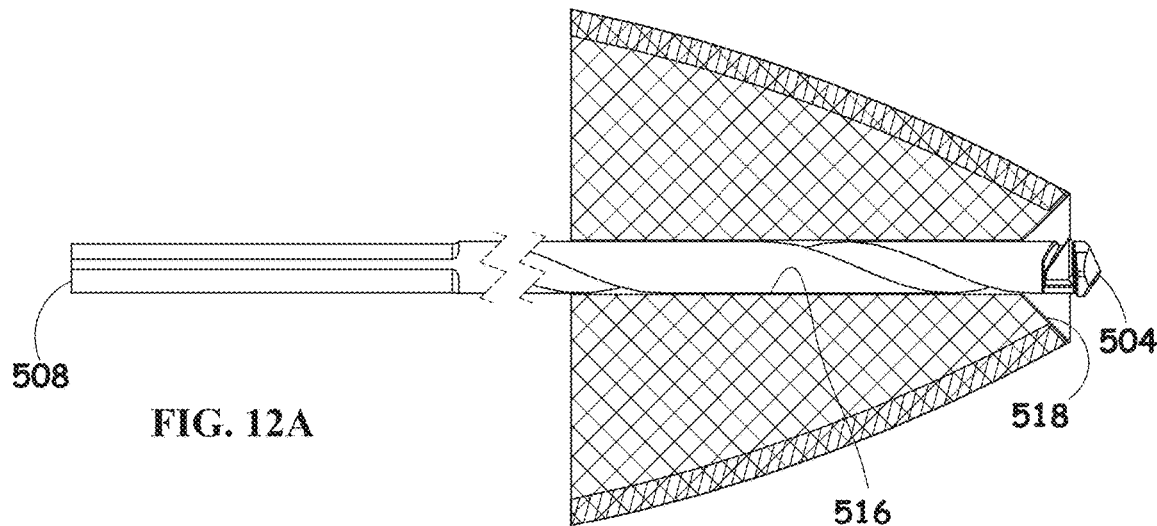
FIGS. 12A-12B are two sectional views of the bone material removal device of FIGS. 5A-6B in an expanded configuration, shown within a bone portion when a bore of a second diameter was drilled partially through the bone portion, according to some embodiments of the invention.
Figure 12B:
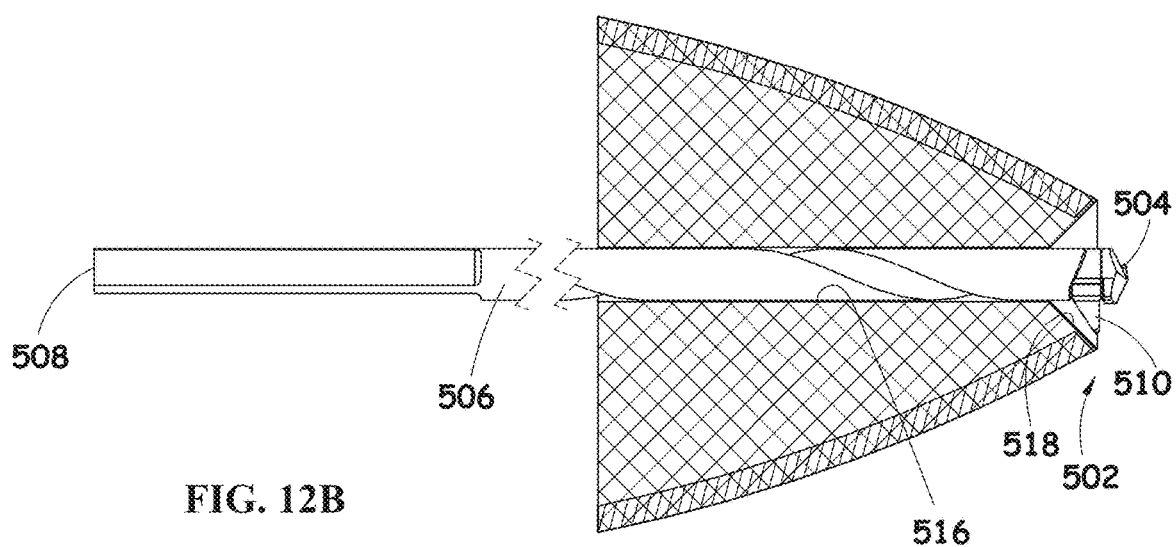

Reference is now made to FIGS. 12A-12B, showing the bone material removal device 500 in an expanded configuration, shown within a bone portion when a bore of a second diameter was drilled partially through the bone portion.

Following reversing of the rotation direction of the drill, the drill is pulled proximally back into the drilled bore of a first diameter 516 and due to the expanded configuration of the cutting tooth 510, a bore of a second diameter 518 is formed partially through the bone portion, along the bore of a first diameter 516, which was previously formed.

Figure 13A:
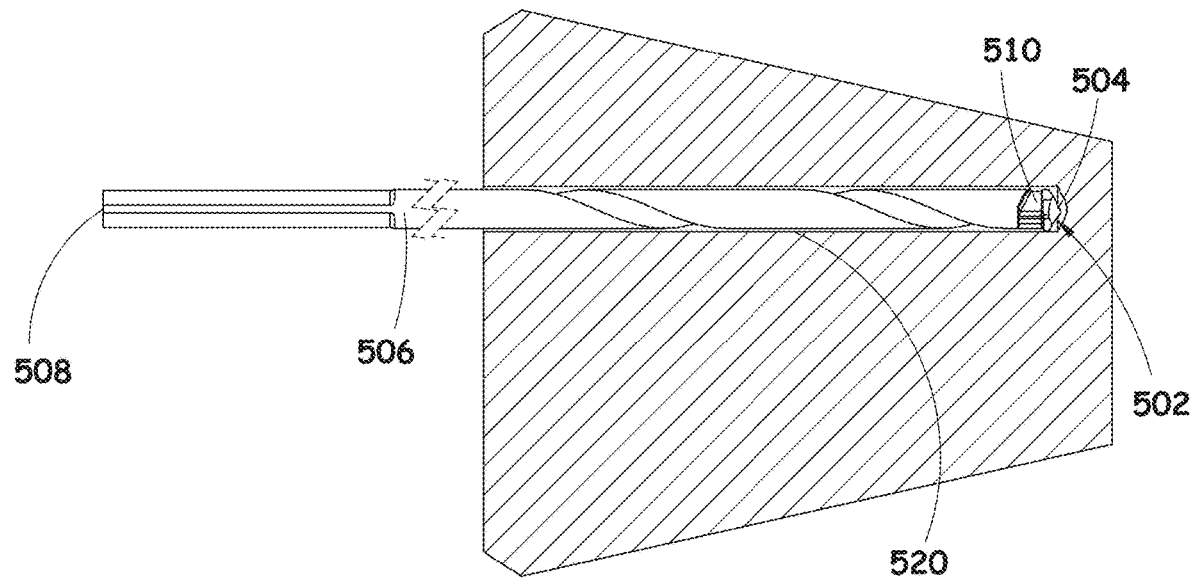
FIGS. 13A-13B are two sectional views of the bone material removal device of FIGS. 5A-6B shown within a bone portion, showing an additional method of use of the device, where a bore of a first diameter was drilled partially through the bone portion and the bone material removal device is shown in a closed configuration, according to some embodiments of the invention.
Figure 13B:
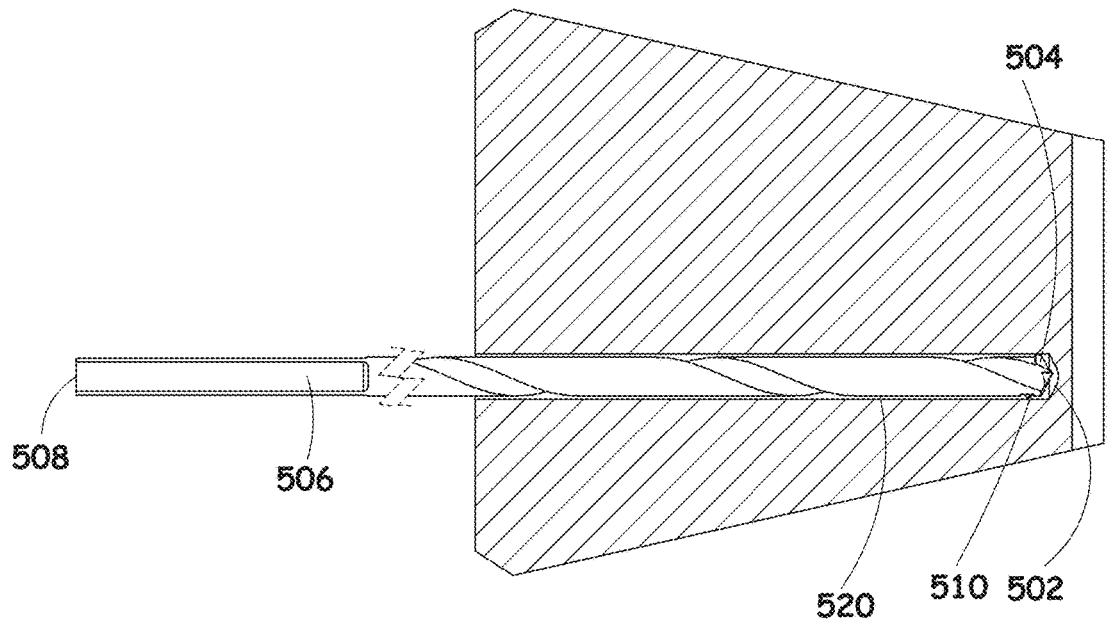

Reference is now made to FIGS. 13A-13B, showing the bone material removal device 500 shown within a bone portion, showing an additional method of use of the device, where a blind bore of a first diameter was drilled partially through the bone portion and the bone material removal device is shown in a closed configuration.

It is seen in FIGS. 13A-13B that the drill of the bone material removal device 500 is used in a closed configuration for providing a bore of a first diameter 516 within a bone portion by inserting the distal tip 504 into the bone portion and rotating the device 500, for example by connection to a drill, preferably drilling a blind bore of a first diameter 520, so that the distal tip 504 of the bone material removal device 500 is positioned within the bone portion and does not extend beyond the bone portion, such that the cutting tooth 510 also resides within the bone portion.

The drill is rotated preferably in a clockwise direction, keeping the cutting tooth 510 in a closed configuration, such that the cutting tooth 510 slightly extends beyond the circumference of the shaft 506.

Figure 14A:
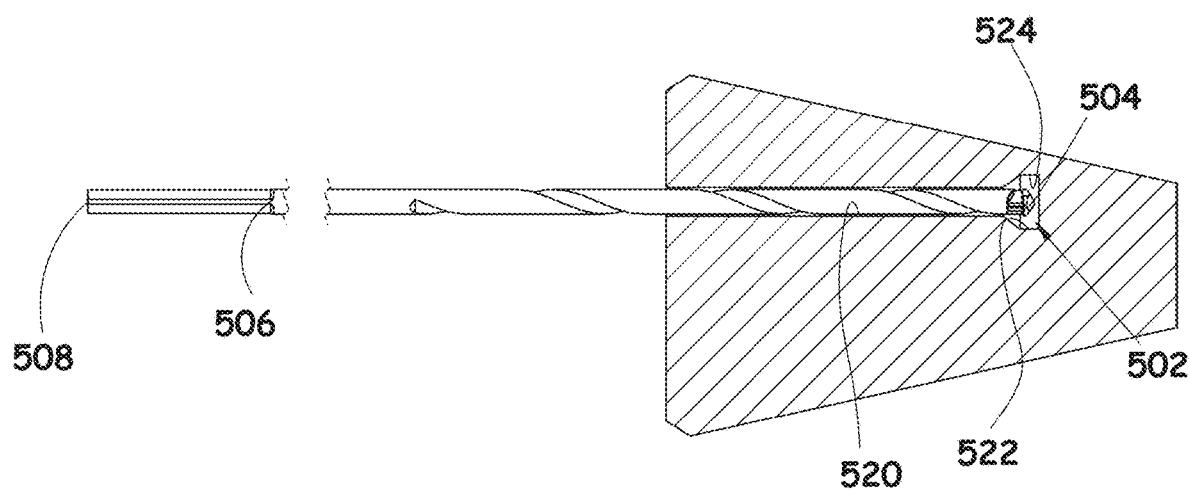
FIGS. 14A-14B are two sectional views of the bone material removal device of FIGS. 5A-6B shown within a bone portion, showing an additional method of use of the device, where a bore of a second diameter was drilled partially through the bone portion and the bone material removal device is shown in an expanded configuration, according to some embodiments of the invention.
Figure 14B:
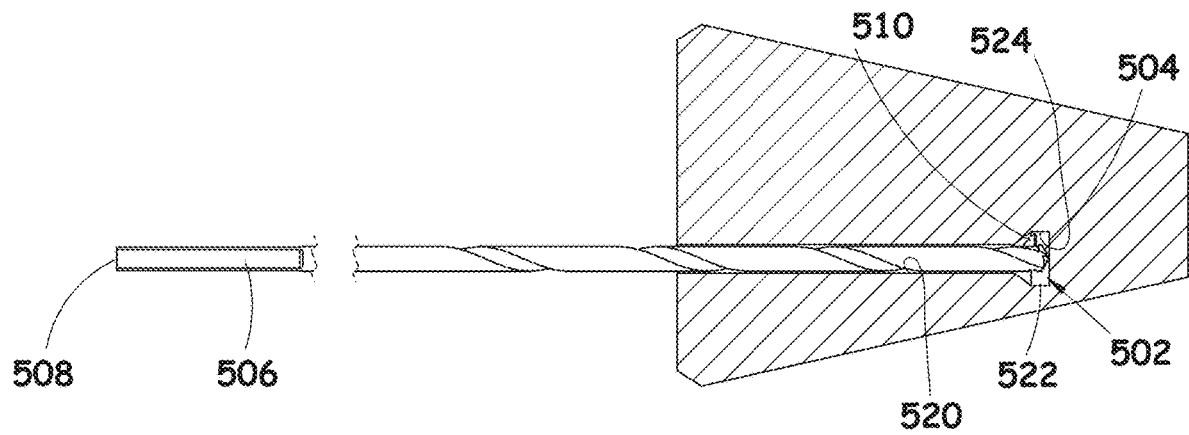

Reference is now made to FIGS. 14A-14B, showing the bone material removal device 500 within a bone portion, showing an additional method of use of the device, where a blind bore of a second diameter was drilled partially through the bone portion and the bone material removal device 500 is shown in an expanded configuration.

It is seen in FIGS. 14A-14B that the drill of the bone material removal device 500 is used in an open configuration for providing a blind bore of a second diameter 522, preferably greater than the first diameter, by reversing the rotation direction of the drill and drilling in an opposite axial direction through a portion of the bore of the first diameter to provide a widened bore portion, preferably forming an undercut 524 within the bone portion.

It is a particular feature of some embodiments of the present invention that the cutting tooth 510 which slightly extends beyond the circumference of the shaft 506, the extension may be in the range of 0.1-0.5 mm, in a closed configuration creates friction force with a portion of the bone once direction of rotation is reversed. The resulting friction force causes expansion of the cutting tooth 510 and provides for drilling a bore of second diameter 522, while assuming an open configuration.

Following reversing of the rotation direction of the drill, the drill is pulled proximally back into the drilled bore of a first diameter 520 and due to the expanded configuration of the cutting tooth 510, a bore of a second diameter 522 is formed partially through the bone portion, along the bore of a first diameter 520, which was previously formed.

It is a particular feature of some embodiments of the present invention that a blind undercut, consisting of a bore of a first diameter 520 and a bore of a second diameter 522, is formed by a single bone material removal device 500, without removing the device 500 from the bone.

It is appreciated that the described blind undercut may be used for positioning of an anchor within the bone.

In an exemplary embodiment of the present invention, the distal expandable portion 502 may be integrally formed with the longitudinal shaft 506 of the drill.

In accordance with another embodiment of the present invention, the distal expandable portion 502 is attachable to the longitudinal shaft 506 of the drill, preferably using a threadable connection. In accordance with this embodiment, the drill may be used as described above in order to form a variable diameter bore, consisting of a bore of a first diameter 520 and a bore of a second diameter 522 and then the longitudinal shaft 506 of the drill may be threadably detached from the expandable distal portion 502, the expandable distal portion 502 preferably is fixedly positioned within the formed blind undercut and is used as an anchor.

Since after the bore of the second diameter 522 is formed, the cutting tooth 510 is positioned in an open expanded configuration, the distal expandable portion 502 is securely positioned within the bone portion and cannot be proximally removed, thus it provides for a safe anchor.

In accordance with another embodiment of the present invention, the length of the distal portion 502 is greater than the diameter of the bone material removal device 500 and the distal expandable portion 502 is attachable to the longitudinal shaft 506 of the drill by non-threadable connection. In accordance with some embodiments, the drill may be used as described above in order to form a variable diameter bore, consisting of a bore of a first diameter 520 and a bore of a second diameter 522 and then the longitudinal shaft 506 of the drill may be detached from the expandable distal portion 502. The distal portion will then change orientation within the blind undercut, rotating approximately 90 degrees to its initial longitudinal orientation. Since the length of the expandable distal portion 502 is greater than the first diameter 520, the distal expandable portion 502 is securely positioned within the bone portion and cannot be proximally removed, thus it provides for a safe anchor.

It is appreciated that in accordance with an exemplary embodiment in which the distal portion is detachable from the longitudinal shaft 506 of the drill, the distal portion is formed of Titanium or any other biologically suitable material.

Reference is now made to FIGS. 15A-15B, which show two elevation views of a drill 600 of a bone removal device similar to the bone removal device shown in FIGS. 5A-5B, constructed according to yet another embodiment of the present invention.

The drill 600 includes a longitudinal shaft 606 having a proximal end 608, a distal tip 610 and a recess 612 for insertion of a cutting tooth therein. In some embodiments, distal tip 610 is a drill bit, optionally having a threaded portion.

It is noted that the drill is cannulated, including a longitudinal bore extending from the distal tip 610 to the proximal end 608 for flushing or removal of residual drilling materials.

Figure 16A:
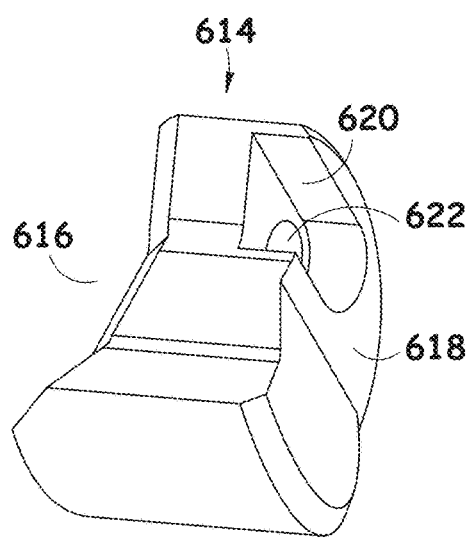
FIGS. 16A-16C are a pictorial view and two elevation views of a cover of the bone removal device, according to some embodiments of the invention.
Figure 16B:
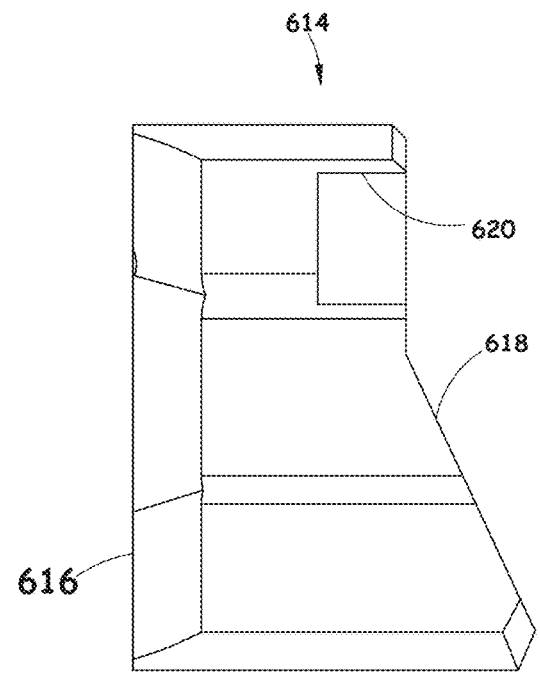
Figure 16C:
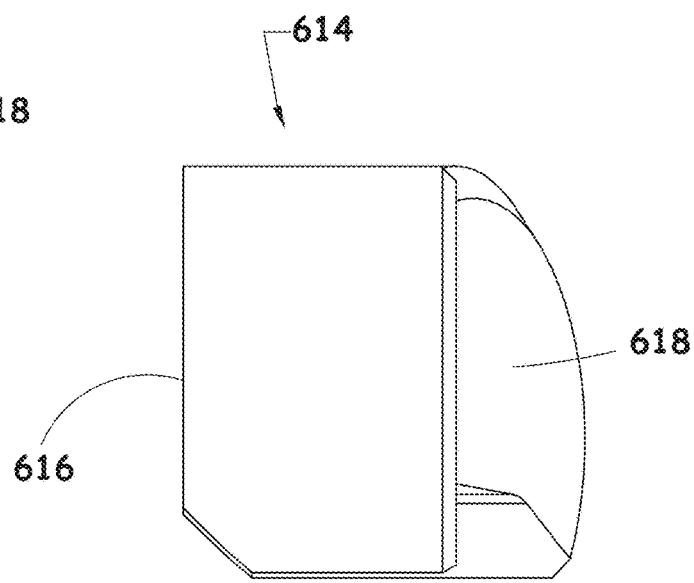
Figure 17D:
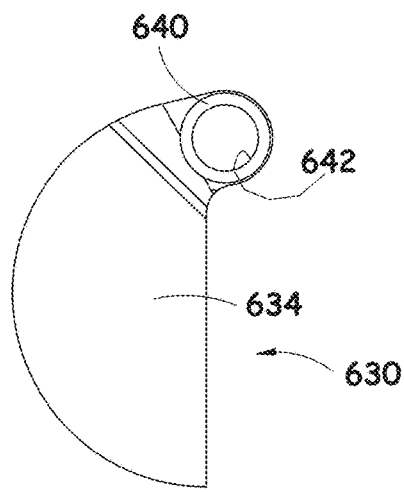
FIGS. 17A-17D are a pictorial view and three different elevation views of a cutting tooth of the bone removal device, according to some embodiments of the invention.
Figure 17C:
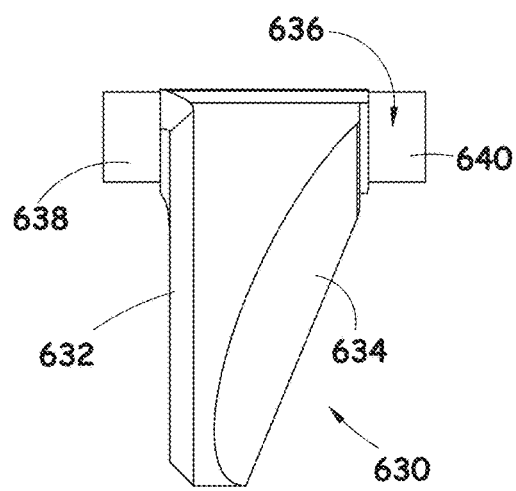
Figure 17A:
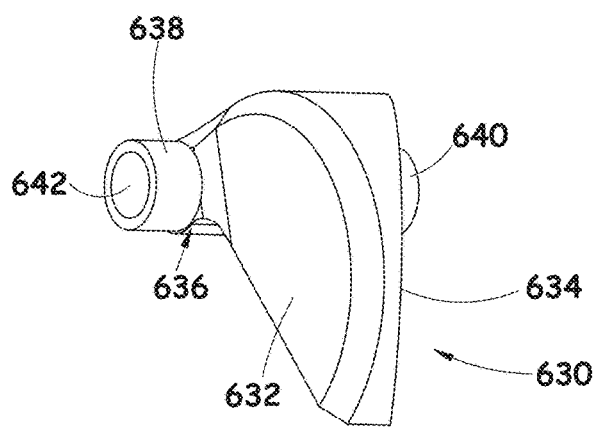
Figure 17B:
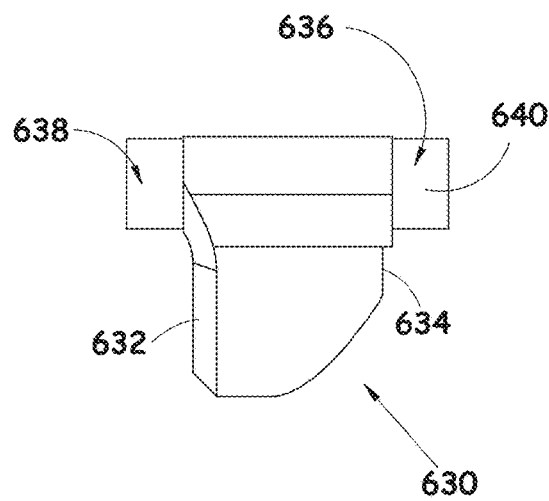

Reference is now made to FIGS. 16A-16C, which illustrate a cover 614 insertable into recess 612 of the drill 600 of the bone material removal device.

The cover 614 is shaped such that it outer dimensions preferably correspond to the circumference of the drill 600 of the bone removal material. The cover 614 has a proximal end 616 and a distal end 618. It is seen particularly in FIGS. 16A-16B that a recess 620 is formed in the distal end 618 of the cover 614 for insertion of a hinge pin within, as shown and described further in detail. A longitudinally extending bore 622 is formed within recess 620.

Reference is now made to FIGS. 17A-17D, which illustrate an exemplary design of a cutting tooth 630 insertable into recess 612 of drill 600 of the bone material removal device.

The cutting tooth 630 has a proximal end 632 and a distal end 634 and a supporting member 636, which has a generally cylindrical proximal portion 638 extending proximally from the proximal end 632 and a generally cylindrical distal portion 640 extending distally from the distal end 634. A longitudinal bore 642 extends through the entire length of the supporting member 636.

Figure 18B:
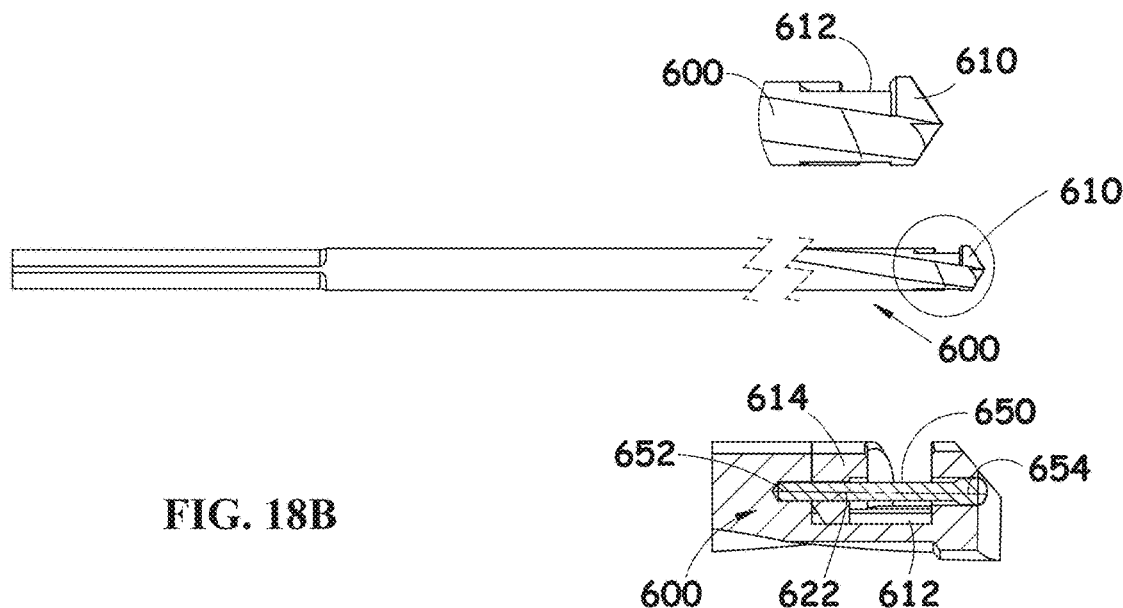
FIGS. 18A-18B are two elevation views and corresponding enlargements of a partial assembly of the bone removal device, showing the drill and the cover of the bone removal device.
Figure 18C:
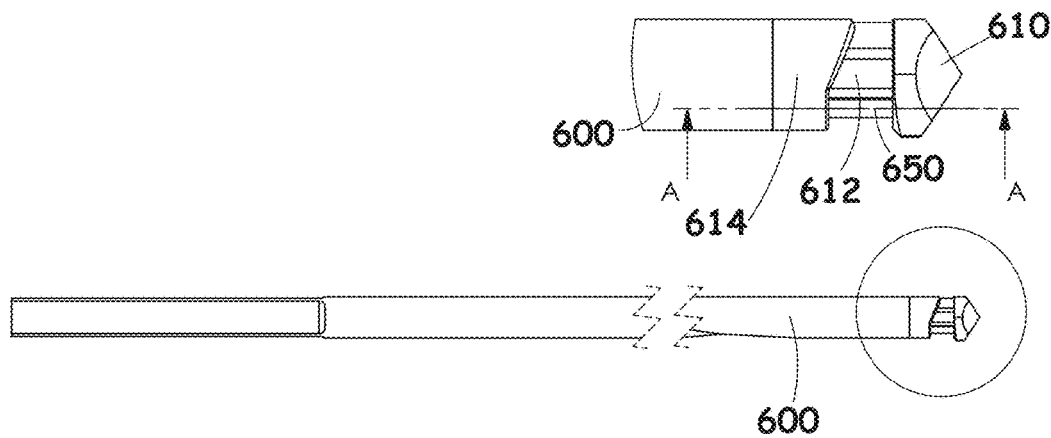
FIG. 18C is an elevation view, enlargement and a section view of a partial assembly of the bone removal device, showing the drill and cover of the bone removal device, according to some embodiments of the invention.
Figure 18A:
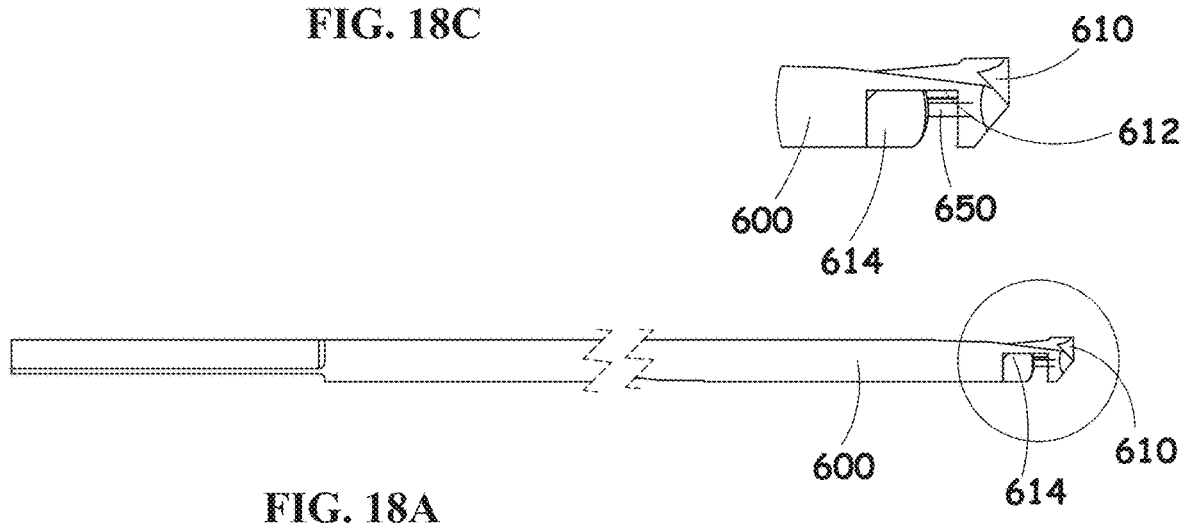

Reference is now made to FIGS. 18A-18C, which illustrate a partial assembly of the bone removal device, showing the drill 600 and the cover 614 of the bone removal device assembled using a hinge pin 650. It is particularly seen in the section view of FIG. 18C that the cover 614 is inserted into the recess 612 of the drill 600 and the hinge pin 650 has a proximal end 652 inserted into bore 622 of the cover 614 and a distal end 654 inserted into the bore formed within the drill 600.

It is appreciated that the length of hinge pin 650 is such that both the proximal end 652 and the distal end 654 of the hinge pin 650 extend substantially into the drill 600 and firmly held therewithin.

Reference is now made to FIGS. 19A-19C, which illustrate the bone material removal device in a closed configuration.

It is particularly seen in FIG. 19C that the cutting tooth 630 is inserted into the recess 612 of the drill 600 of the bone removal device using the hinge pin 650. It is seen that the proximal end 632 of the cutting tooth 630 engages the distal end 618 of the cover 614 and that the distal portion 638 of the supporting member 636 of the cutting tooth 630 is inserted into the recess 620 and the longitudinal bore 622 of the cover 614. The distal portion 640 of the supporting member 636 of the cutting tooth 630 is inserted into the longitudinal bore of the drill 600.

It is a particular feature of some embodiments of the present invention that the aforementioned assembly of drill 600 and cutting tooth 630 using a hinge pin 650 enables secure pivotable connection between the drill 600 and the cutting tooth 630. Due to insertion of the hinge pin 650 into the recess 620 formed in the cover 614 and the fact that the hinge pin 650 is firmly held at both of its ends within the drill 600, the cutting tooth 630 is securely held in the recess 612 of the drill 600 and cannot be removed therefrom.

It is a particular feature of some embodiments of the present invention that even in case that the hinge pin 650 is broken, the cutting tooth 630 is securely held attached to the drill 600 due to the supporting member 636, which is irreversibly inserted into the drill 600 at one end and into the cover 614 at the other end.

It is thus noted that the cutting tooth 630 is irremovably attached to the drill 600 by at least one of a hinge pin 650 or supporting member 636.

It is appreciated that increasing the length of the hinge pin 650 correspondingly increases the force that may be exerted on the drill without resulting in breaking of the hinge pin 650.

It is seen in FIGS. 19A-19C that the cutting tooth 630 slightly extends beyond the outer circumference of the shaft 606 when the cutting tooth 630 is in the closed configuration.

Reference is now made to FIGS. 20A-20C, which illustrate the bone material removal device in an expanded configuration.

The cutting tooth 630 is pivotable about the hinge pin 650. It is seen that in the open expanded configuration the cutting tooth 630 maximally extends beyond the outer circumference of the shaft 606.

The operation of the bone material removal device shown in FIGS. 15A-20C is similar to the operation of bone material device 500, which is shown in FIGS. 10A-14B.

Figure 21:
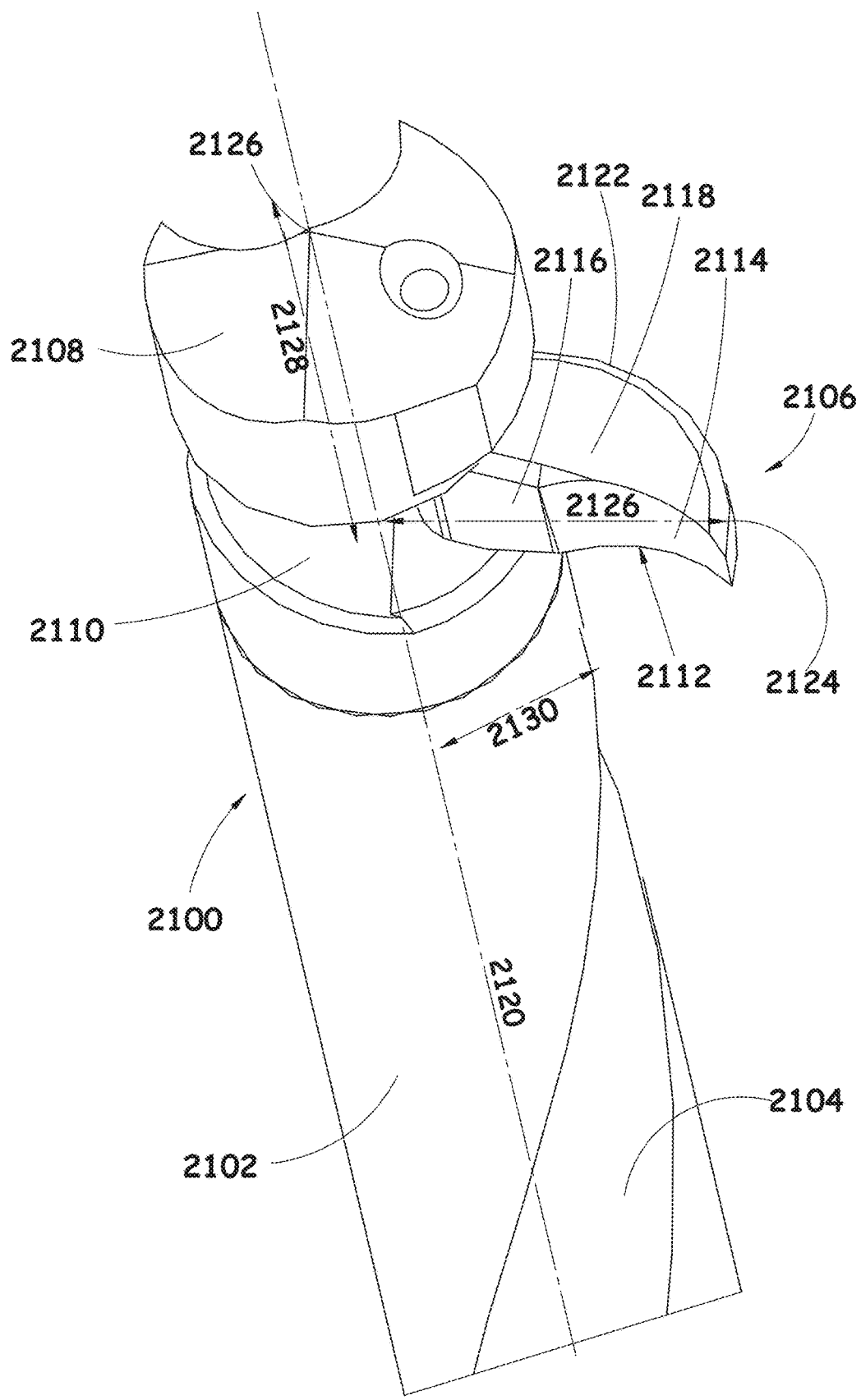
FIG. 21 is an exemplary bone material removal device comprising an extendible cutting tooth, according to some embodiments of the invention.

Reference is now made to FIG. 21, which shows an exemplary bone material removal device 2100, comprising an extendible cutting tooth 2106, according to some embodiments of the invention.

In some embodiments, device 2100 comprises a shaft 2102. Optionally, a head 2108 is configured at a distal end of the shaft.

In some embodiments, cutting tooth 2106 is at least partially received within a recess 2110 formed in shaft 2102, for example when the tooth is in a closed configuration. In some embodiments, cutting tooth 2106 is pivotally connected to shaft 2102, for example by a hinge.

In some embodiments, the hinge (hidden in this figure) is positioned along a central, longitudinal axis 2120 of the shaft. Alternatively, the hinge is positioned offset from axis 2120, for example positioned at a distance ranging between, for example, 0.5-2 mm, such as 0.7 mm, 1.3 mm, 1.8 mm or intermediate, larger or smaller distances from axis 2120.

In some embodiments, for example as shown herein, cutting tooth 2106 comprises a cutting face 2112. In some embodiments, cutting face 2112 formed with a curvature on at least a portion of the cutting surface. For example, at least a portion of the surface, such as portion 2114, is concave. Additionally or alternatively, at least a portion of the surface such as portion 2116 is flat.

In some embodiments, planar portion 2116 is configured in proximity axis 2120, while curved portion 2114 is configured radially outwardly to planar portion 2116. In some embodiments, such as during closing of the tooth, planar portion 2116 is pushed against an inner wall of recess 2110 within shaft 2102. Optionally, planar portion 2116 resists over-closure of the tooth (e.g. the tooth entering deeper within recess 2110 when force is applied to a back wall 2122 of the tooth). A potential advantage of a planar portion 2116 may include increased wear resistance and/or reduced risk of breakage when the tooth is being pushed into recess 2110 against the shaft material, for example as compared to closure over an edge or a corner of a tooth.

In some embodiments, a top surface 2118 of tooth 2106, facing a distal direction towards head 2108, is flat. Optionally, top surface 2118 is configured to engage a bottom surface of head 2108 when the tooth is in a closed position, for example formed as a flat surface suitable to contact a bottom surface of head 2108 such that no gaps are formed between the surfaces.

In some embodiments, in an open configuration, a radially outward edge 2124 of tooth 2106 is located at a distance 2126 from axis 2120 of the shaft ranging between, for example, 1.1-1.5 times a radius 2130 of the shaft, for example a radius of a shaft portion configured directly below recess 2110. Optionally, the distance 2126 is selected, for example by a surgeon, to produce a bore of a desired diameter. In some cases, a graft is harvested, and the extent of the open tooth is selected such as to widen a bore to a diameter suitable for receiving the graft.

In some embodiments, shaft 2102 is cylindrical, for example as shown herein. Optionally, when inserted to a bone, shaft 2102 defines a generally cylindrical volume of rotation, producing a bore with a similar geometry. Alternatively, shaft 2102 comprises a different geometry, for example comprising a polygonal cross section, such as hexagonal or octagonal cross section. Optionally, a volume or rotation defined by a shaft with a polygonal cross section is cylindrical as well.

In some embodiments, device 2100 is a drill bit, such as a twist-type drill bit. In some embodiments, shaft 2102 of the device is formed with one or more flutes 2104. Optionally, the twist rate of flute 2104 is selected to provide a certain bone chip removal rate.

In some embodiments, head 2108 comprises tapering distal end, optionally formed with a pointed tip 2126.

In some embodiments, tooth 2106 is located a distance from tip 2126 in a proximal direction, such as a distance 2128 from tip 2124 ranging between, for example, 4-7 mm, 3-9 mm, 2-5 mm or intermediate, larger or smaller ranges. Optionally, distance 2128 is selected, one the one hand, to be close enough to distal dip 2126 such as to reduce damage to tissue configured beyond the bone, and, on the other hand, to be spaced enough from distal tip 2126 so that it does not interfere with a drilling function of the tip and/or does not affect the strength of the distal portion.

In some embodiments, a proximal end of shaft 2102 (not shown in this figure) is configured to engage a drill, for example formed with a shank.

Various embodiments of bone material removal devices may include various numbers of cutting teeth, for example 2, 3, 4, 5, 8, 10 or intermediate, larger or smaller numbers of cutting teeth. Optionally, the plurality of cutting teeth are distributed circumferentially around the shaft. Optionally, the plurality of cutting teeth are positioned at various locations along longitudinal axis 2120.

Figures 22A, 22B:
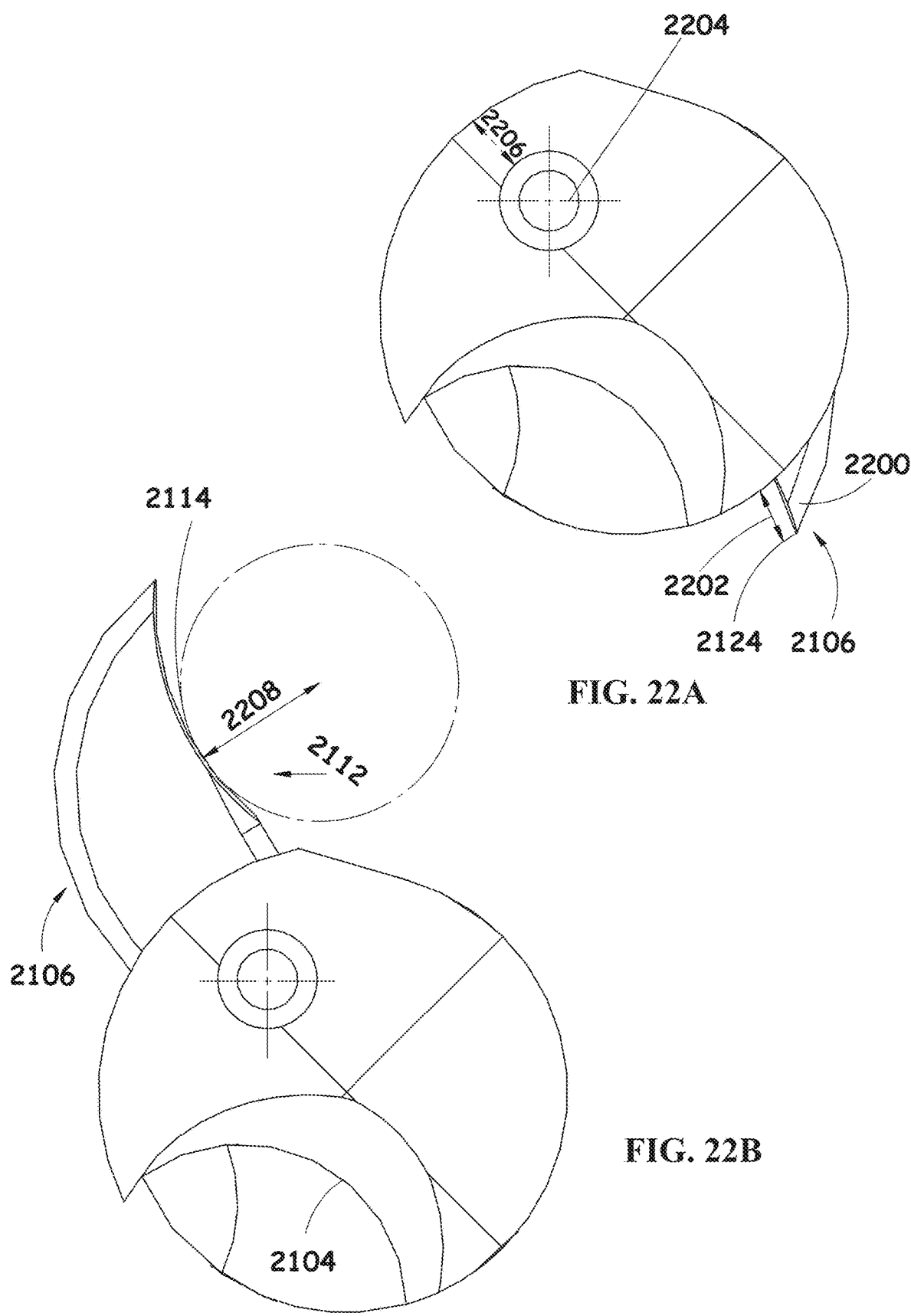
FIGS. 22A-22B are front views of a device comprising a cutting tooth for bone removal, showing a closed configuration of the cutting tooth (A) and an open configuration of the cutting tooth (B), according to some embodiments of the invention.

Reference is now made to FIG. 22A-22B, which are front views of a device comprising a cutting tooth for bone removal, showing a closed configuration of the cutting tooth (A) and an open configuration of the cutting tooth (B), according to some embodiments of the invention.

Referring to FIG. 22A, showing tooth 2106 in a closed configuration, in some embodiments, at least a portion 2200 of tooth 2106 extends beyond the shaft, for example extending to a distance 2202 from a periphery of shaft the shaft ranging between, for example, 0.1-0.4 mm, such as 0.2 mm, 0.3 mm, or intermediate, larger or smaller distances. Optionally, the protruding portion 2200 of tooth 2106 increases a diameter of a bore drilled by the device, for example increasing a diameter of the bore by 0.5%, 2%, 5%, 10% or intermediate, larger or smaller percentages in comparison to a diameter which would have been formed by the shaft without the protruding portion 2200 of the tooth. For example, if a diameter of the shaft is, for example, 4.5 mm, a diameter of a bore formed by the device with a protruding portion of a cutting tooth (when the tooth is in a closed configuration) may range between, for example, 4.6-5 mm.

In some embodiments, hinge 2204 (as this figure shows a front view of the device 2204 indicates a location of the hinge) is positioned away from a periphery of the shaft, for example positioned at a distance 2206 ranging between 0.15-0.4 mm, such as 0.2 mm, 0.3 mm, 0.35 mm or intermediate, larger or smaller distances. A potential advantage of a hinge that is located away from a periphery of the shaft may include reducing the risk of damage, such as breakage, to the hinge.

In some embodiments, radially outward edge 2124 of protruding portion 2200 extends parallel to an axis defined by hinge 2204 (extending in a proximal-distal direction). Alternatively, edge 2124 is slanted, and configured at an angle with respect to an axis defined by hinge 2204.

FIG. 22B, shows tooth 2106 in an open configuration, according to some embodiments of the invention. In some embodiments, a radius of curvature 2208 of curved portion 2114, for example formed with a concave surface, ranges between, for example, 1.5 mm-4 mm.

In some embodiments, tooth 2106 is positioned with respect to shaft 2102 in a way that the concavity of cutting face 2112 faces an opposite direction from flute 2104, for example to provide an additional removal track for the removed bone material.

Optionally, the concavity and the flute are diametrically opposed.

In some embodiments, tooth 2106 is formed of a rigid material, such as nitinol, stainless steel, platinum, other metals, polymers such as PEEK, and/or other rigid materials. Optionally, the tooth is formed of a material that is more rigid then bone tissue, so that it does not break and/or deform when engaging the bone.

In some embodiments, the device is rotated at a rate ranging between, for example, 0.01-1000 rpm, such as 5 rpm, 70 rpm, 250 rpm, 700 rpm, or intermediate, higher or lower rates. In some embodiments, the device is manually operated. Additionally or alternatively, the device is coupled, for example on a proximal end of the shaft, to a drill such as a surgical drill.

In some embodiments, a rigidity of the tooth is selected according to the rotation rate, for example the tooth is selected to be more elastic to withstand higher rotation rates and to reduce damage such as chipping to the tooth. Respectively, a more rigid tooth can be used with lower rotation rates.

In some embodiments, a rigidity of the tooth is selected according to the tissue in which the bore is drilled. In an example, for drilling in a tibia body portion, a tooth formed of titanium may be used. Optionally, rotational speed of 1000 rpm is applied. In another example, for drilling in a distal and/or proximal ends of the tibia, such as in the tibial plateau, the selected tooth may be formed of stainless steel (PH174), which is harder than titanium, and the rotational speed may be lower, for example 500 rpm.

Figure 23:
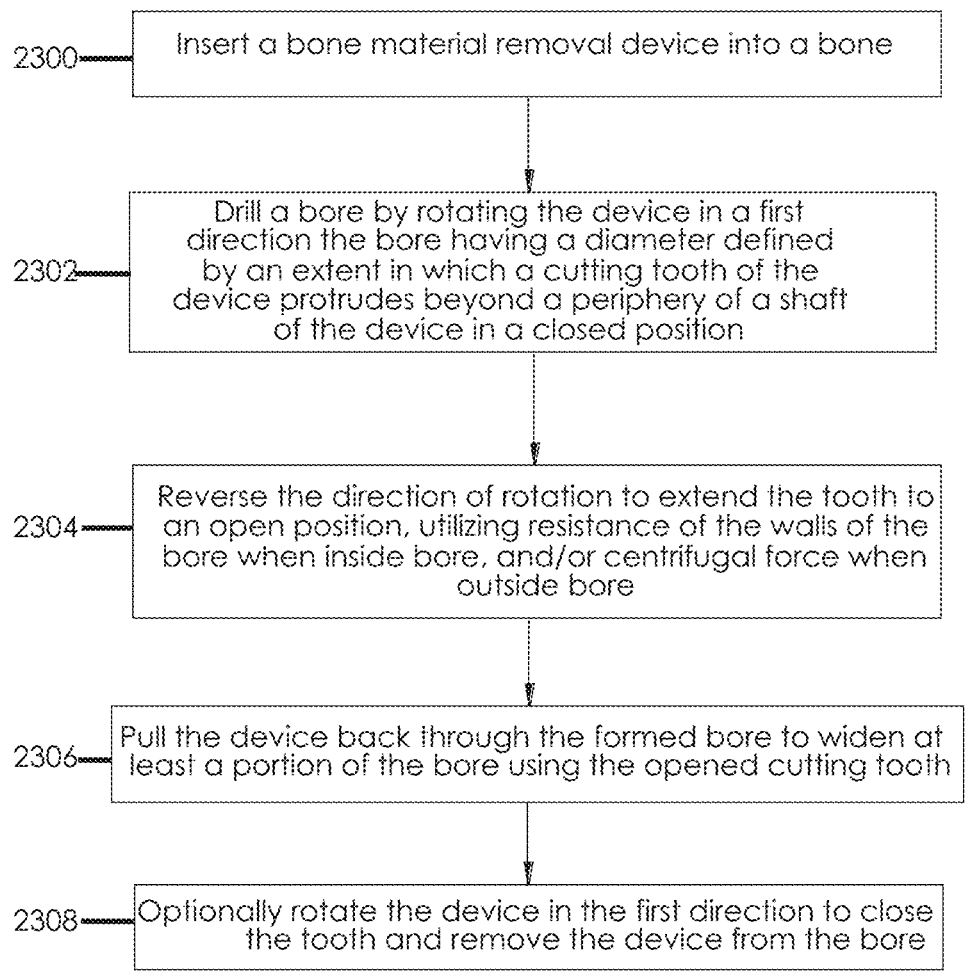
FIG. 23 is a flowchart of a method for drilling a bore, and widening at least a portion of the bore using a bone material removal device comprising a cutting tooth, according to some embodiments of the invention.

Reference is now made to FIG. 23, which is a flowchart of a method for drilling a bore, and widening at least a portion of the bore, according to some embodiments of the invention.

In some embodiments, a bone material removal device is inserted, such as by drilling, into a bone 2300. In some embodiments, inserting comprises rotating the device to form the bore 2302. In some embodiments, a cutting tooth of the device extends beyond a periphery of a shaft of the device, forming a bore with a diameter that is defined by the radial extent of the cutting tooth in a closed position.

In some embodiments, the device is inserted into the bone until exiting a face of the bone different than the entering face. Optionally, the device is advanced until at least the cutting tooth exits a distal opening of the bore. Alternatively, the device is advanced until other portions along the length of the device exit a distal opening of the bore.

Alternatively, in some embodiments, the device is advanced only a certain distance within the bone, and does not form a distal opening to the bore.

In some embodiments, for example once a required depth of the bore is obtained, the device is rotated in an opposite direction to the rotation direction used for insertion of the device 2304. In some embodiments, for example if the cutting tooth is within the bore, the protruding portion of the tooth is pushed against the walls of the bore. Optionally, as rotation continues, the resisting force applied by the walls of the bore on the protruding portion of the tooth increases, until the tooth is forced to rotate into an open configuration. Additionally or alternatively, rotation of the device in an opposite direction to the drilling direction causes opening of the tooth, for example due to centrifugal force. In some embodiments, rotation-based opening is performed when the tooth has been advanced passed the bone, and was positioned in a lumen which imposes less resistance to opening of the tooth, such as in comparison to the resistance imposed by the walls of the bore.

In some embodiments, the device comprising the opened tooth is pulled back in a proximal direction 2306, to widen at least a portion of the formed bore. Optionally, the device is rotated 2308 in a direction opposite to the initial drilling direction to keep the tooth in an open position. In some embodiments, the opened tooth cuts bone tissue surrounding the initial walls of the bore, thereby increasing a diameter of the bore.

In some embodiments, only a portion of the bore is widened. Optionally, the device is rotated once again in the first, initial drilling rotation to cause the tooth to close. Optionally, once the tooth is closed, the device is removed from the bore, such as through a proximal opening of the bore. Alternatively, the device is pulled along a complete length of the bore with the tooth in an open configuration, to widen the bore along its length.

Figure 24A:
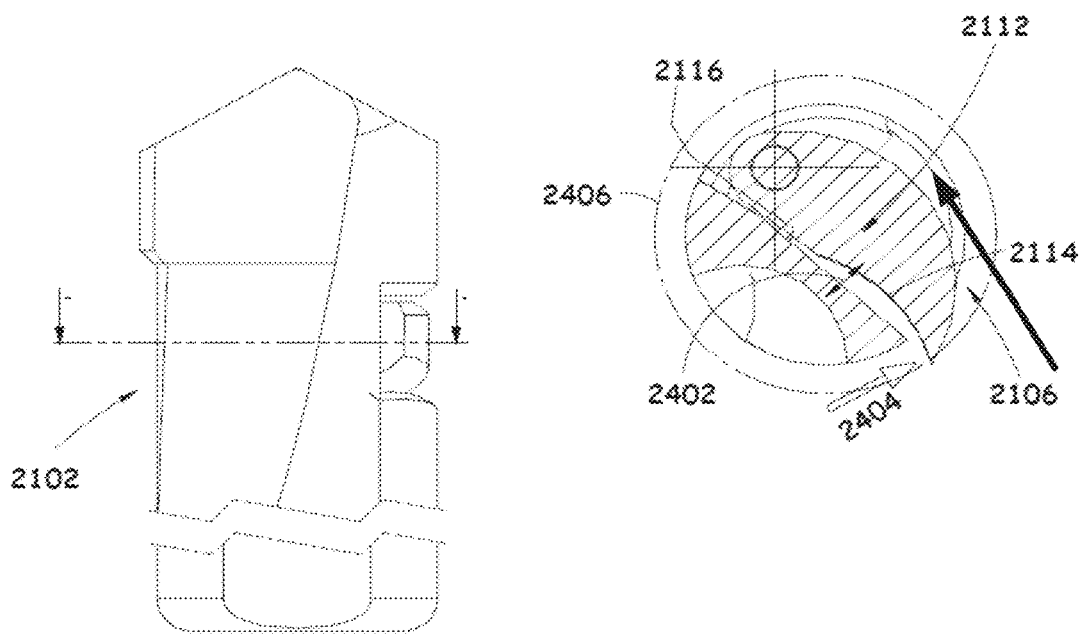
FIGS. 24A-24B are cross sections of a shaft of a bone removal device showing an extendible cutting tooth, according to some embodiments of the invention.
Figure 24B:
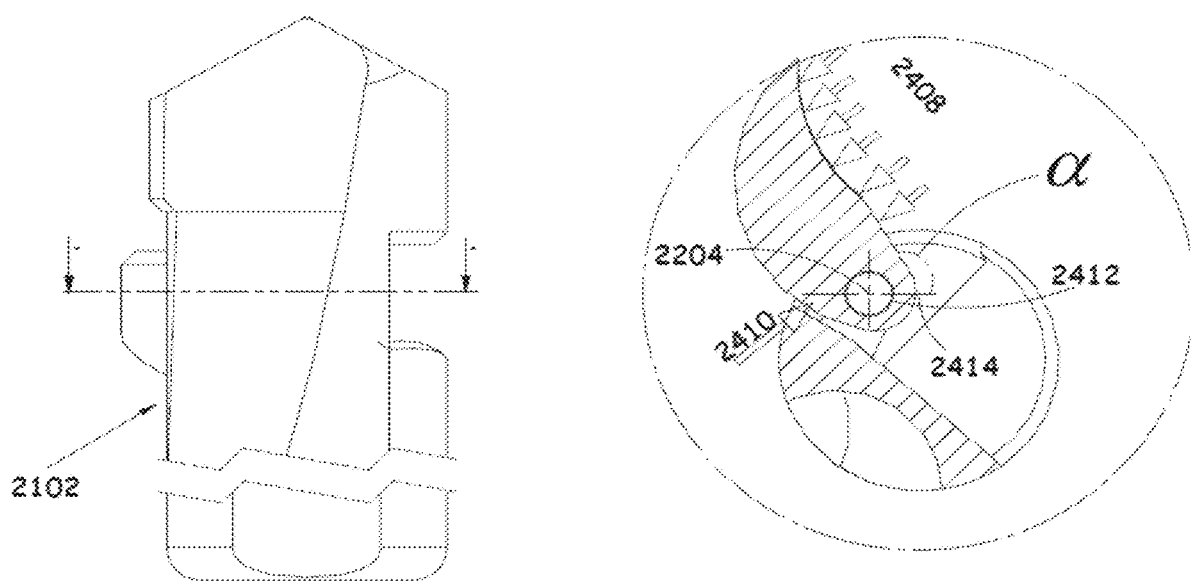

Reference is now made to FIGS. 24A-24B, which are cross sections of shaft 2102 at the cutting tooth 2106, according to some embodiments of the invention.

In some embodiments, for example as shown in FIG. 24A, cutting face 2112 leans against shaft wall 2406 when the tooth is in a closed position. Optionally, flat portion 2116 of the cutting face fully contacts shaft wall 2406, while concave portion 2114 defines a gap 2402 between the shaft wall 2406 and the cutting face. In some embodiments, gap 2402 ranges between, for example, 0.25-0.7 mm, such as 0.3 mm, 0.45 mm, 0.6 mm or intermediate, larger or smaller distances.

In some embodiments, for example when the device is rotated in an opposite direction to the drilling direction to open the tooth, force 2404, applied by walls of the formed bore 2406, acts on protruding portion 2200. Optionally, friction is created between edge 2124 of the cutting tooth 2106 and bore walls 2406. In some cases, force 2404 increases as the rotation continues, until causing tooth 2106 to spin open.

In some embodiments, for example as shown in FIG. 24B, various forces may act on open tooth 2106 during widening of the bore. In some cases, force 2408 is applied onto cutting face 2112 due to resistance of the bone tissue which the tooth cuts through. Optionally, the curvature of cutting face 2112 is configured to distribute force 2408 along cutting face 2112. Optionally, the arcuate configuration of concave portion 2114 spreads force 2408 over a larger surface area, for example as compared to a flat surface, reducing the magnitude of the force acting on each point along cutting face 2112.

In some embodiments, a force 2410 is applied by shaft wall 2406 onto back wall 2122. Optionally, force 2410 limits movement of tooth 2106, for example preventing tooth 2106 from over-opening.

In some embodiments, tooth 2106 is coupled to hinge 2204 in a way that enables tooth 2106 to rotate freely on hinge. In some embodiments, tooth 2106 comprises a recess 2412 to be threaded onto a rod of hinge 2204. Optionally, recess 2412 is shaped and/or sized to freely rotate on the rod hinge.

Alternatively, in some embodiments, hinge 2204 is configured to limit movement such as rotational movement of the tooth and/or axial movement (lengthwise movement) of the tooth, for example by comprising one or more projections which lock into respective recess in the shaft body for limiting movement of the tooth.

In some embodiments, hinge 2204 comprises an elastic element such as a spring. Optionally, the spring is used to actuate opening of the tooth.

In some embodiments, an opening angle α of tooth 2106, measured for example between flat surface 2116 of the tooth 2106 and horizontal axis 2414 extending through a center of hinge 2204 and indicating the location of the hinge, ranges between, 0-130 degrees, such as 60 degrees, 90 degrees, 120 degrees or intermediate, larger or smaller angles.

Figure 25:
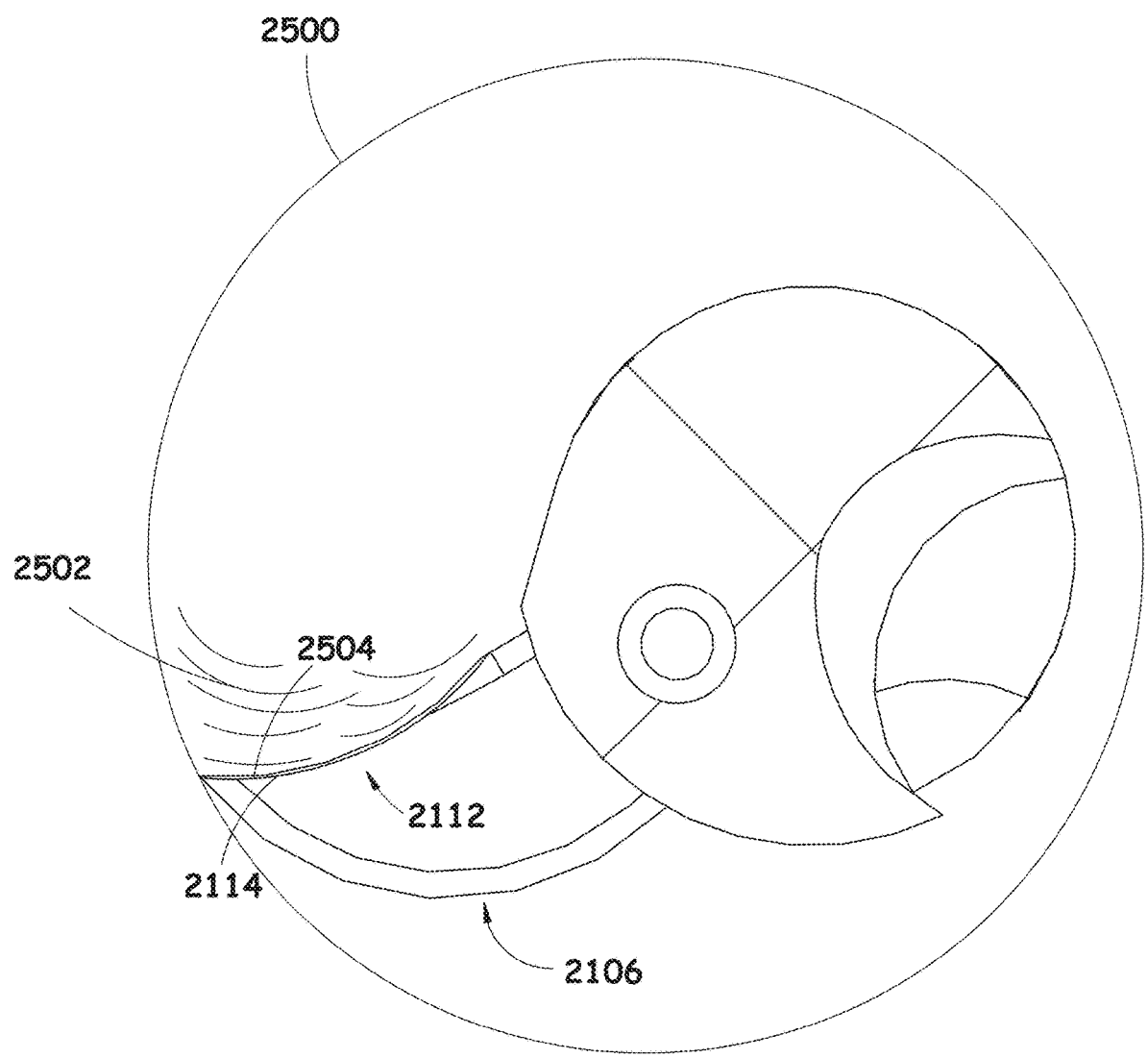
FIG. 25 is a front view of a bone removal device shown within a bore formed in the bone, according to some embodiments of the invention.

Reference is now made to FIG. 25, which is a front view of a bone removal device shown within a bore formed in the bone, according to some embodiments of the invention.

As shown in this figure, tooth 2106 is in an open configuration, effective to widen bore 2500. In some embodiments, cutting face 2112 is shaped to allow removal of the removed bone material 2502, for example including removed bone chips and/or dust. In some cases, for example when the device is used in a laparoscopic surgery, the bore is produced and/or widened in a fluid environment, and the removed bone material is not formed as solid bone chips, but rather as fluid or paste. Optionally, the removed bone material is removed through the concavity of the cutting face. A function of the concavity of the cutting face 2112 can be compared to the function of a flute on a drill.

In some embodiments, the removed bone material 2502 which is formed during widening of the bore flows in various directions, for example flowing in a proximal direction, a distal direction, and/or radially outward direction towards the walls of bore 2500. In some embodiments, the removed bone material 2502 exits through a proximal opening and/or a distal opening of the bore. In some embodiments, during operation, at least some removed bone material may accumulate at a central area 2504 of concave portion 2114. Optionally, the bone material then flows in the proximal and/or distal direction passed the top and/or bottom surfaces of the tooth, "freeing" the tooth from the material temporarily, for example until the device is further rotated and new bone material is cut by the tooth 2106.

In some embodiments, when forming a bore, a system suitable for evacuating the removed bone material may be used, to clear the bore.

Reference is now made to FIGS. 26A-26E, which show a cutting tooth 2106 from various directions, according to some embodiments of the invention.

In some embodiments, a top surface 2118 of the tooth is flat. Alternatively, top surface 2118 is formed with a curvature.

In some embodiments, back wall 2122 is arc-shaped. Optionally, back wall 2122 is shaped and/or sized to flush with the shaft of the device when the tooth is closed. In some embodiments, bottom surface 2600 of the tooth is formed with a curvature. Optionally, bottom surface 2600 is an inclined surface. Alternatively, bottom surface 2600 is flat.

In some embodiments, a height 2602 of tooth 2106, for example measured between the top and bottom surfaces along flat portion 2116, ranges between, for example, 2-3 mm, 1-4 mm, 2-6 mm, or intermediate, larger or smaller heights. Optionally, height 2602 varies along the radial axis of the tooth, for example it may decrease towards radially outwards edge 2124 which is farthest away from the shaft when the tooth is an open configuration. A potential advantage of a varying height of a tooth, which decreases in the direction of the outer walls of the bore, may include gradual application of force on the bone tissue that is being cut, which may facilitate removal of bone material.

In some embodiments, a width 2604 of tooth 2106, for example measured between back wall 2122 and cutting face 2112 at flat portion 2116, ranges between, for example, 1.5-3 mm, such as 1.7 mm, 2 mm, 2.5 mm or intermediate, larger or smaller widths.

In some embodiments, tooth 2106 comprises one or more slots or channels such as channel 2606 through which bone material can be removed. Optionally, the channel extends along cutting face 2112, for example extending in a radially outward direction to define a path towards the walls of the bore, and/or in a different direction, such as along the height of tooth 2106, to define a path for removing material in the proximal and/or distal directions of the bore.

In some embodiments, tooth 2106 is detachable from the bone removal device.

In some embodiments, a kit comprising a bone removal device and a plurality of different shapes and/or sizes of teeth is provided, and a tooth is selected according to the type and/or size and/or shape of the bone, and/or a shape and/or size of the bore to be formed in the bone. In some embodiments, a unit comprising a cutting tooth is provided, for example constructed as a shaft segment which can be assembled and/or detached from the rest of the shaft of the device. Optionally, the unit includes a distal head of the device in addition to the tooth.

Figure 27:
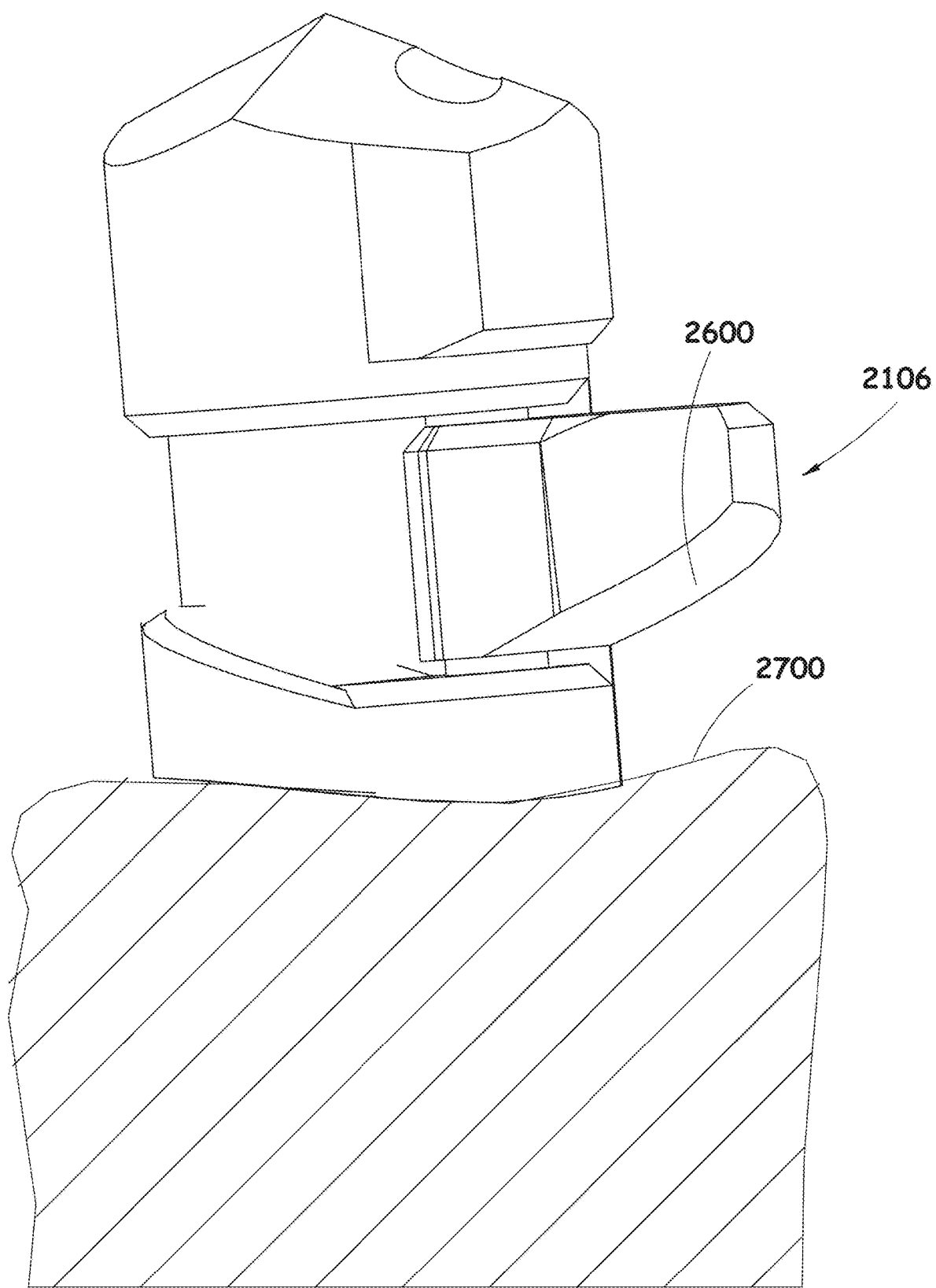
FIG. 27 illustrates a cutting tooth of a bone material removal device positioned against a bone surface, for example before widening a formed bore in the bone, according to some embodiments of the invention.

Reference is now made to FIG. 27, which illustrates a cutting tooth 2106 of a bone material removal device positioned against a bone surface 2700, for example before back-drilling to widen a formed bore in the bone, according to some embodiments of the invention. As described herein, bottom surface 2600 is formed with a curvature and/or inclination, suitable to engage a non-planar geometry of the bone surface 2700.

Figure 28:
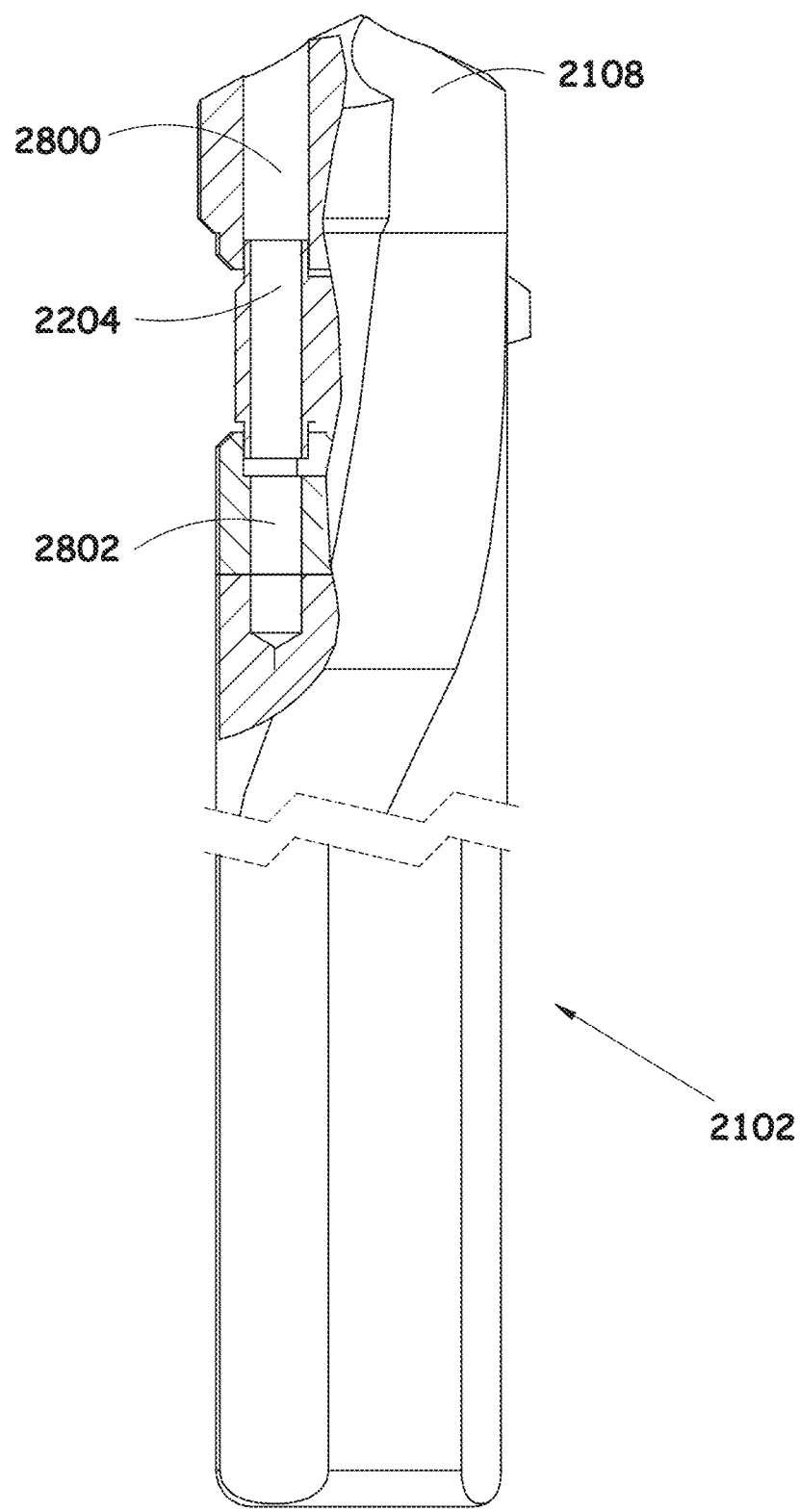
FIG. 28 is an illustration of shaft of a bone material removal device comprising a hinge, according to some embodiments of the invention.

Reference is now made to FIG. 28, which is an illustration of shaft 2102 of a bone material removal device comprising a hinge 2204, according to some embodiments of the invention.

In some embodiments, for example as shown in an exposed portion of the shaft, hinge 2204 comprises a rod formed with a distal extension 2800 and/or a proximal extension 2802. In some embodiments, distal extension 2800 is received within a recess in head 2108. In some embodiments, proximal extension 2802 is received within a recess in the inner body of shaft 2102. Optionally, extensions 2800 and 2802 secure the hinge in place, reducing a risk of disengagement of the hinge and thereby of the cutting tooth. Optionally, a length of an extension such as 2802 is, for example, at least 3 mm, at least 5 mm, at least 6 mm or intermediate larger or smaller lengths. Optionally, length of distal extension 2800 ranges between, for example, 4-7 mm, 3-9 mm, 2-5 mm or intermediate, larger or smaller ranges. In some embodiments, distal extension 2800 extends to a distal end of head 2108, but does not surpass the distal end of the head.

Figure 29A:
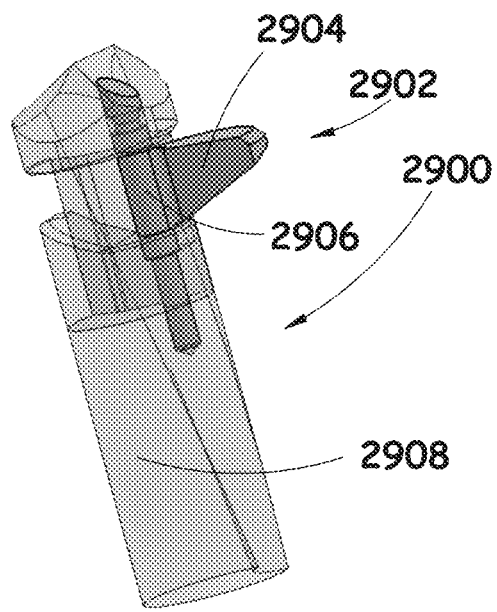
FIGS. 29A-29C show an exemplary bone material removal device comprising a cutting tooth formed with a flat cutting face, according to some embodiments of the invention.
Figure 29B:
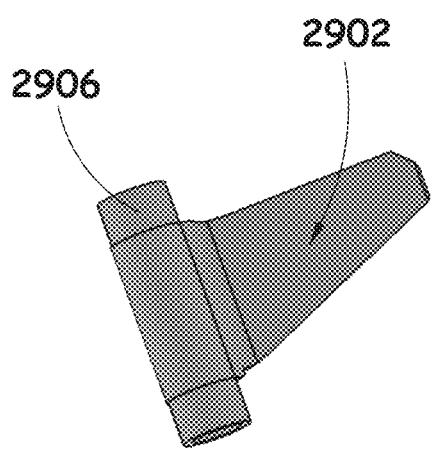
Figure 29C:
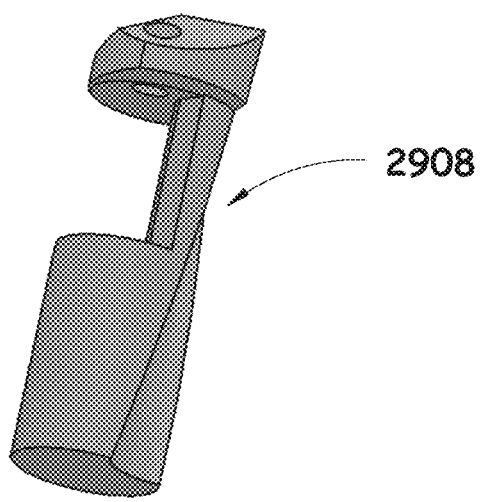

Reference is now made to FIGS. 29A-29C, which show an exemplary bone material removal device 2900 comprising a cutting tooth 2902 formed with a flat cutting face 2904, according to some embodiments of the invention. FIG. 29B shows the cutting tooth 2902 coupled to a rod hinge 2906, and FIG. 29C shows a shaft 2908 of device 2900 separated from the cutting tooth and hinge. A flat cutting face 2904 may apply equally distributed force, along its radial axis, on the bone material.

Figure 30A:
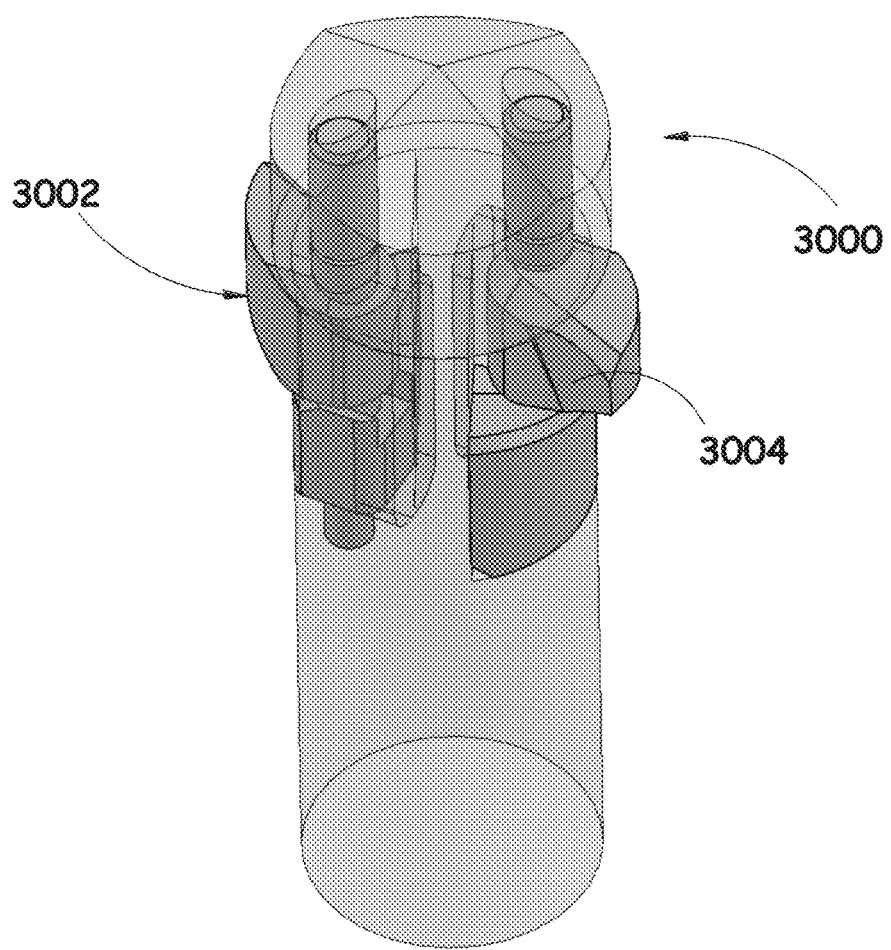
FIGS. 30A-30C illustrate a bone material removal device comprising a plurality of cutting teeth, according to some embodiments of the invention.
Figure 30B:
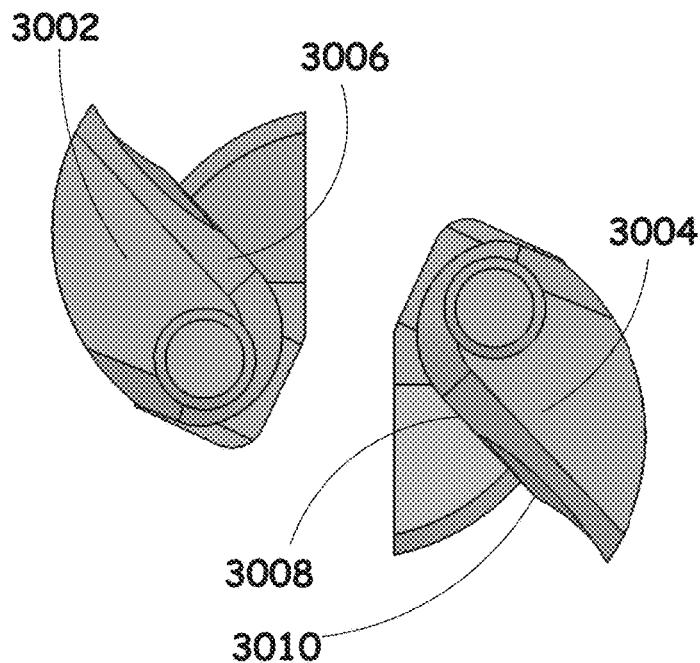
Figure 30C:
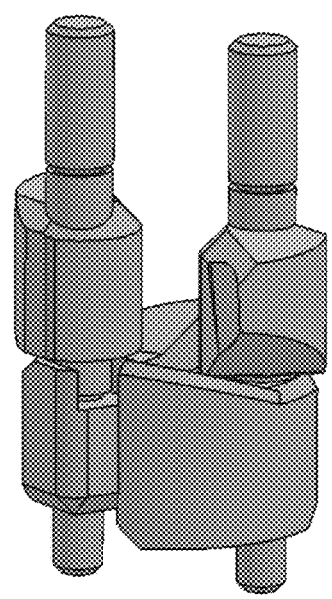

Reference is now made to FIGS. 30A-30C, which illustrate a bone material removal device 3000 comprising a plurality of cutting teeth, such as two cutting teeth, according to some embodiments of the invention. FIGS. 30B and 30C are a cross section and a side view, respectively, showing the two cutting teeth and their respective hinges separately from a shaft of device 3000, to provide a clearer view.

In some embodiments, teeth 3002 and 3004 are positioned diametrically opposing each other. Optionally, the teeth are oriented in a configuration in which their cutting faces 3006 and 3008 respectively face opposite directions. A potential advantage of widening a bore using a plurality of cutting teeth may include increasing a rate of bone material removal.

In some embodiments, for example as shown in FIG. 30B, a concavity 3010 of a cutting face is non-symmetrical, for example along a height of the tooth.

In addition to all the above described, the present invention in some embodiments thereof, relates to a kit of tools including a guiding system and bone material removal tools, for example, tools in which an effective diameter of the tool is selectable.

Figure 31:
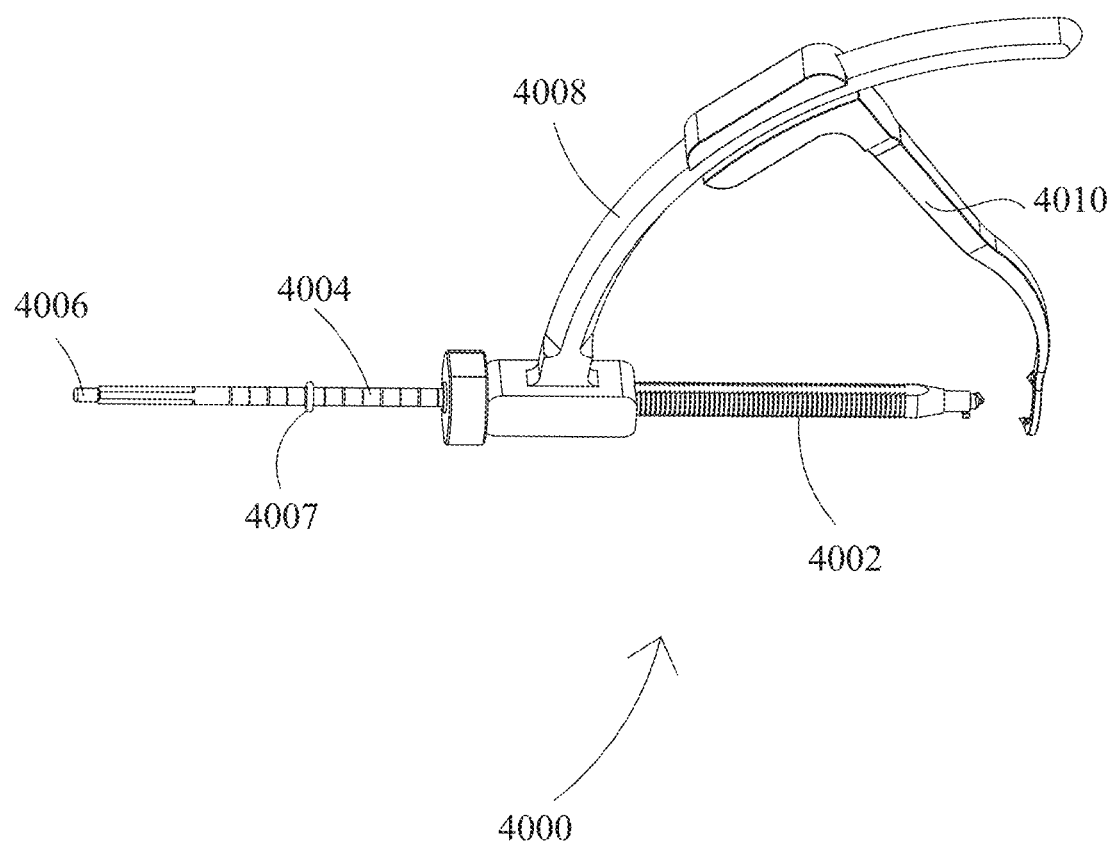
FIG. 31 is a simplified pictorial illustration of a kit including a guiding system and a bone material removal device, constructed and operative according to some embodiments of the invention.
Figure 32:
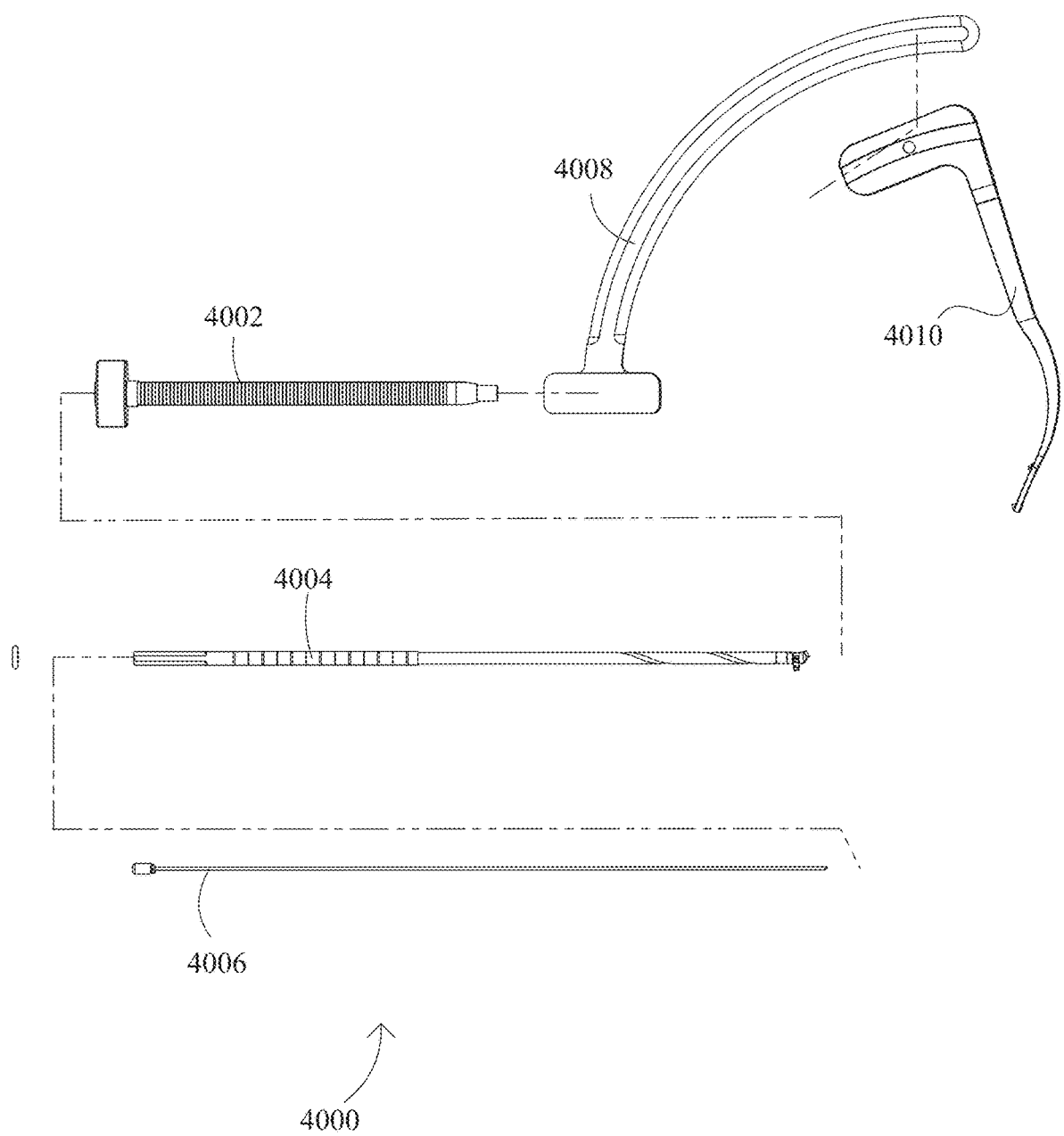
FIG. 32 is a simplified exploded view illustration of the kit including a guiding system and a bone material removal device shown in FIG. 31, according to some embodiments of the invention.

Reference is now made to FIG. 31, which is a simplified pictorial illustration of a kit 4000 including a guiding system and a bone material removal device 4004, constructed and operative in accordance with an embodiment of the present invention; and to FIG. 32, which is a simplified exploded view illustration of the kit 4000 including a guiding system and a bone material removal device 4004 shown in FIG. 31.

Figure 33A:
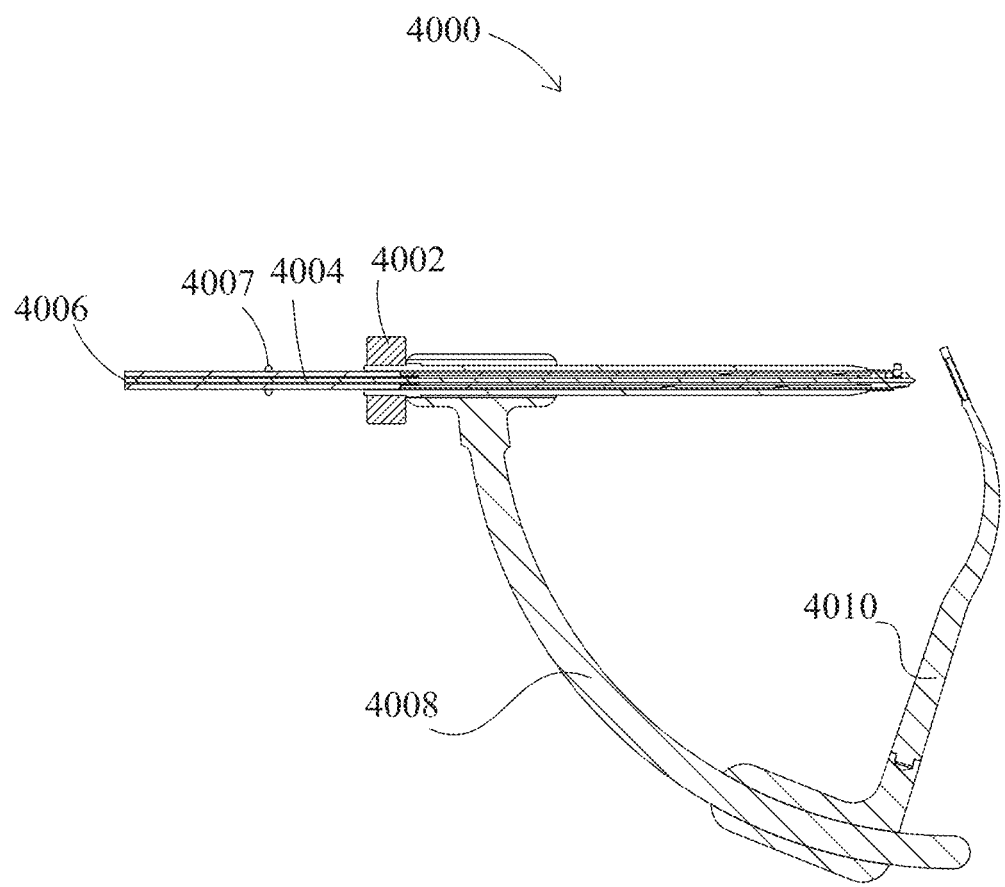
FIGS. 33A-33B are simplified side view and sectional illustrations of the kit including a guiding system and a bone material removal device shown in FIG. 31, section is being taken along lines A-A in FIG. 33A, according to some embodiments of the invention.
Figure 33B:
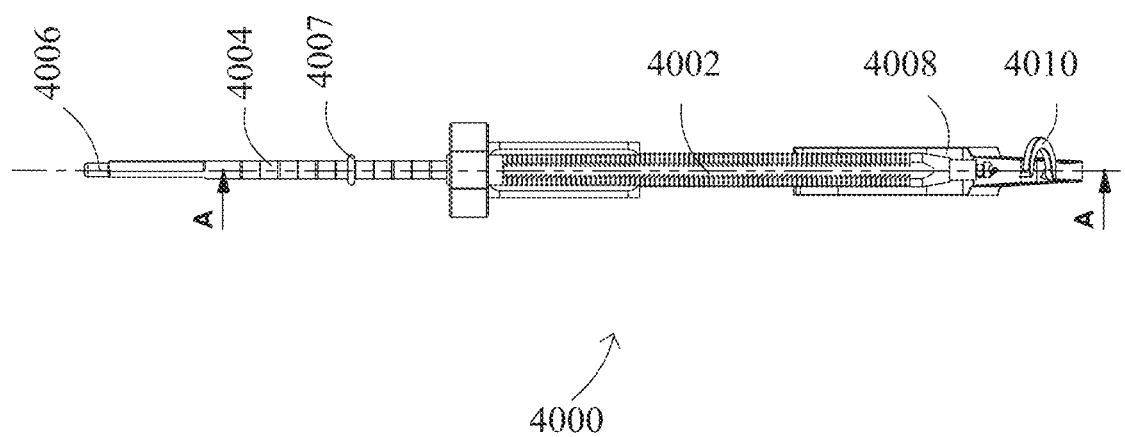

Reference is additionally made to FIGS. 33A-33B, which are simplified side view and sectional illustrations of the kit including a guiding system and a bone material removal device shown in FIG. 31, section is being taken along lines A-A in FIG. 33A.

A kit 4000 including a guiding system and a bone material removal device 4004 is seen in FIGS. 31-33B. The kit 4000 preferably includes a cannula 4002, the lumen of which is configured to partially accommodate a bone material removal device 4004.

It is a particular feature of some embodiments of the present invention that the bone material removal device 4004 is itself also cannulated and adapted for accommodating a longitudinal instrument; for example a K-wire 4006.

In some embodiments, a positioning "O-ring" 4007 or other stopper/marker device is adapted to be seated on the bone material removal device 4004 at a position where it can be brought to limit longitudinal motion of the bone material removal device 4004 relative to the guiding system. Herein the "O" in O-ring should be understood to refer to an optional shape of this marker, rather than denoting an element having a particular function in a mechanical seal. Optionally, the O-ring 4007 is repositionable. For example, the O-ring comprises an elastic band, and sized to friction-fit onto the shaft of the bone material removal device. Optionally, the O-ring is further secured by seating into one of a plurality of circumferential grooves along the shaft of the device.

In some embodiments, an arc 4008 is configured to be slidably coupled to the cannula 4002, and a guide is configured to be slidably attached to the arc 4008. The guide may be selected from a group of various guides, such as left femoral guide 4010, right femoral guide 4012, left tibial guide and right tibial guide 4016. It is appreciated that any other guide may be used in conjunction with kit 4000 constructed and operative in accordance with an embodiment of the present invention. For illustrative purpose only, left femoral guide 4010 is shown in FIGS. 31-33B.

Figure 34:
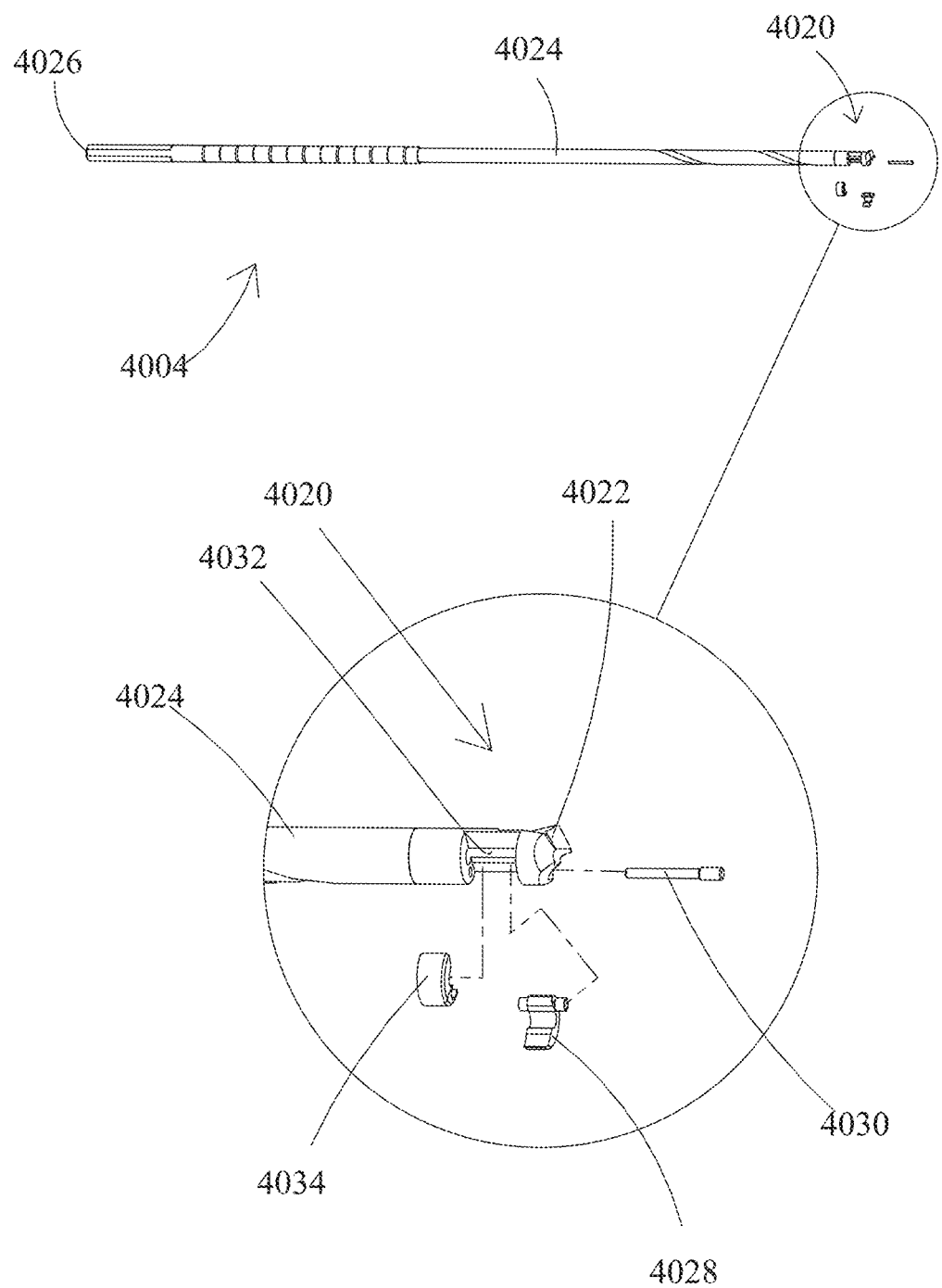
FIG. 34 is a simplified exploded view illustration of the bone removal device comprising an expandable distal tip and a partial enlargement thereof, according to some embodiments of the invention.
Figure 35B:
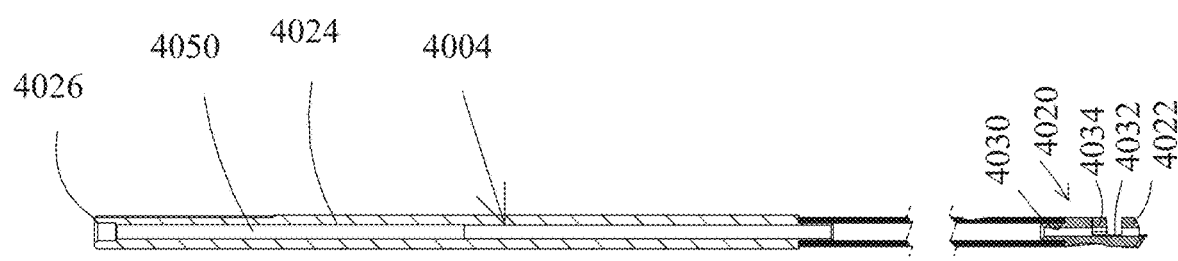
FIGS. 35A-35B are simplified side view and sectional illustrations of the bone material removal device shown in FIG. 34, section is being taken along lines B-B in FIG. 35A, according to some embodiments of the invention.
Figure 35A:
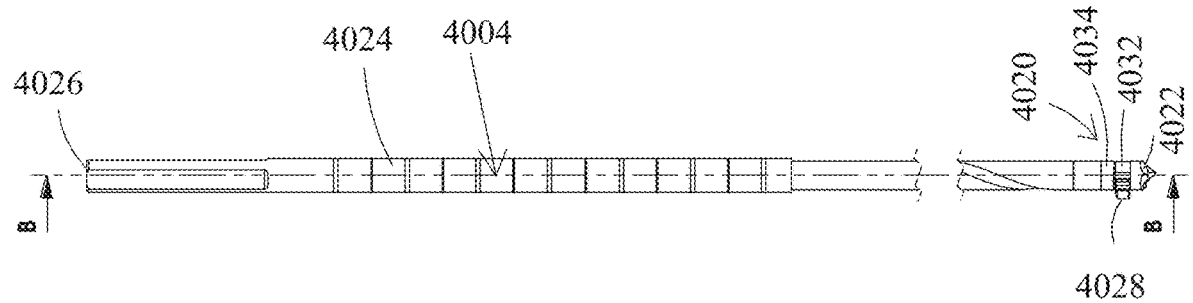

Reference is now made to FIG. 34, which is a simplified exploded view illustration of the bone removal device 4004 comprising an expandable distal tip and a partial enlargement thereof, according to an embodiment of the present invention; and to FIGS. 35A-35B, which are simplified side view and sectional illustrations of the bone material removal device 4004 shown in FIG. 34, section is being taken along lines B-B in FIG. 35A.

Figure 36B:
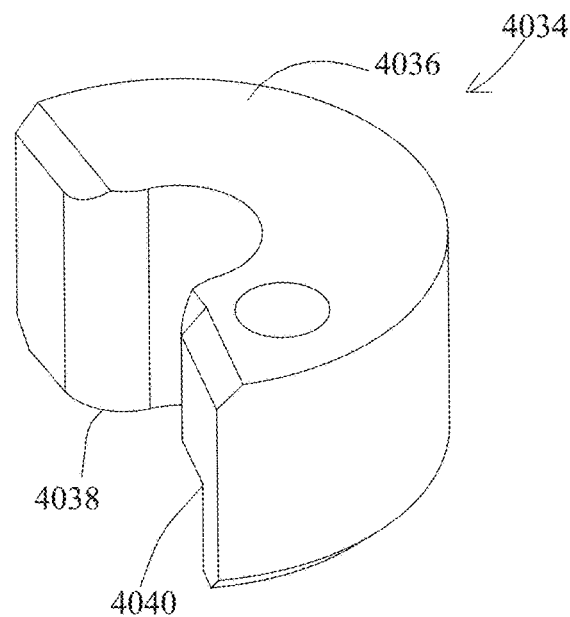
FIGS. 36A-36B are two different simplified pictorial view illustrations showing a cover of the bone removal device shown in FIG. 34 from two opposite ends, according to some embodiments of the invention.
Figure 36A:
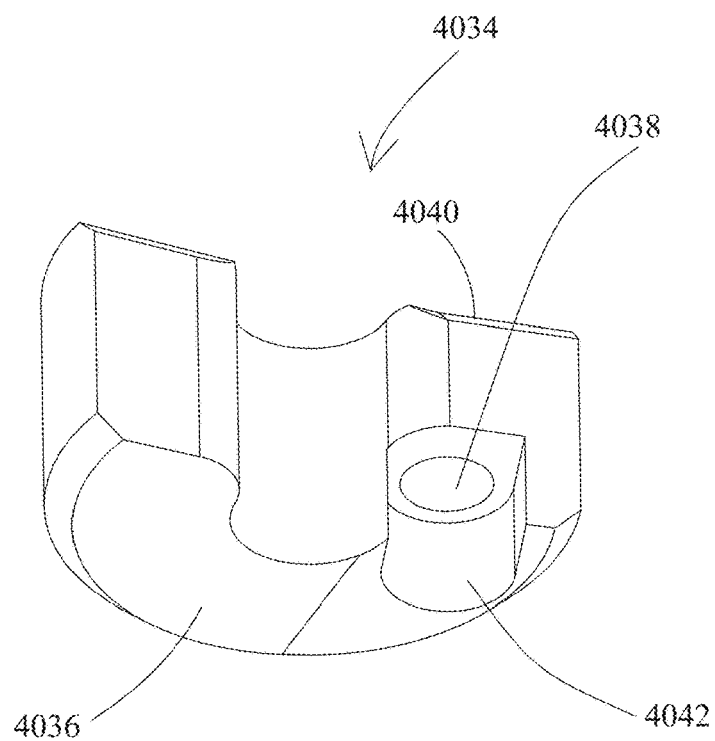
Figure 37B:
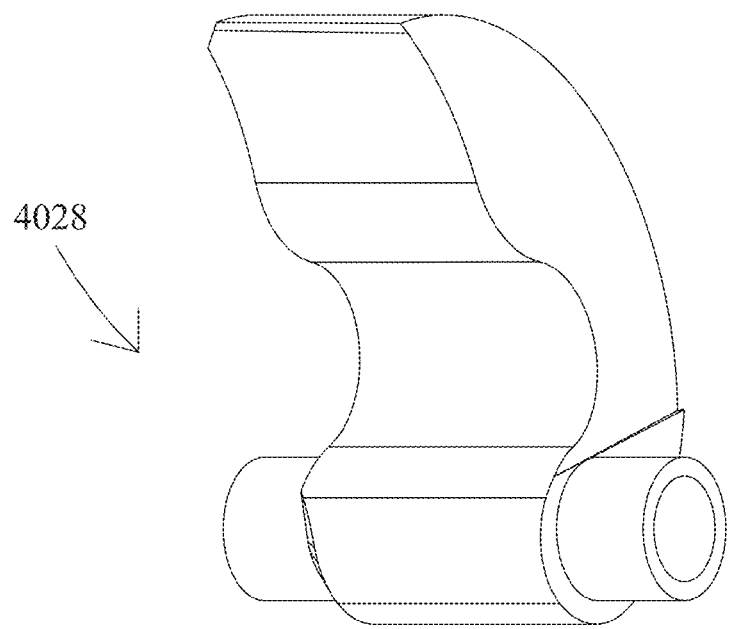
FIGS. 37A-37B are two different simplified pictorial view illustrations showing a cutting tooth of the bone removal device shown in FIG. 34 from two opposite ends, according to some embodiments of the invention.
Figure 37A:
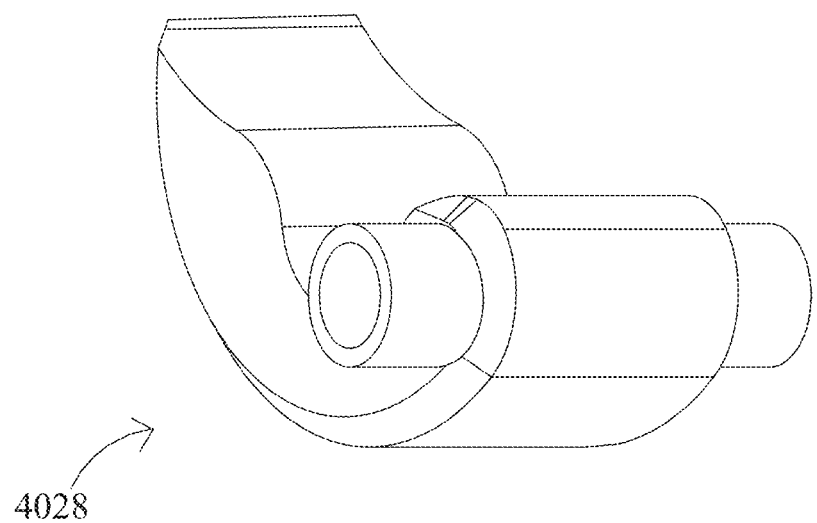
Figure 38:
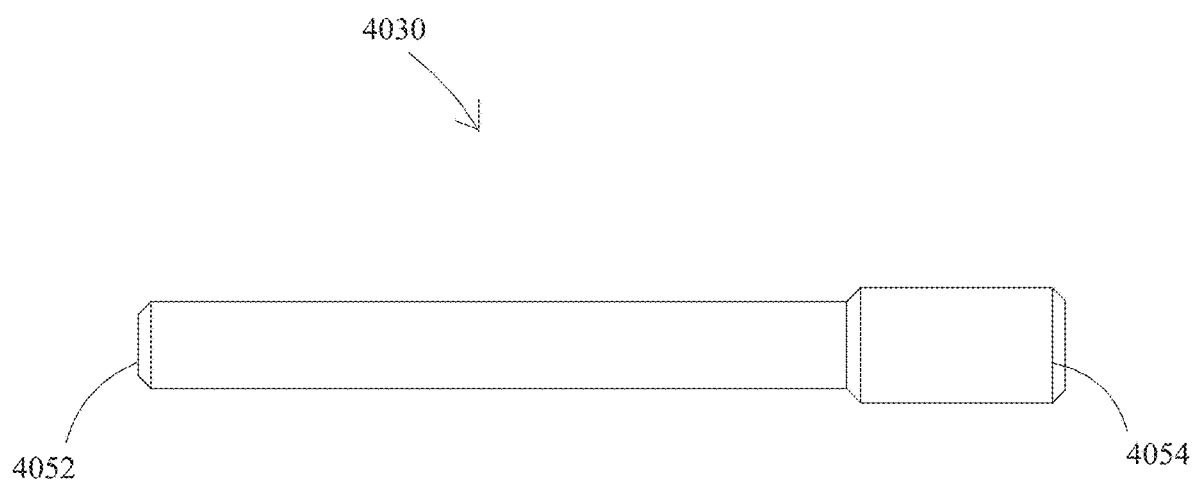
FIG. 38 is a simplified pictorial illustration of a hinge of the bone removal device shown in FIG. 34, according to some embodiments of the invention.

Reference is additionally made to FIGS. 36A-36B, which are two different to simplified pictorial view illustrations showing a cover of the bone removal device shown in FIG. 34 from two opposite ends and to FIGS. 37A-37B, which are two different simplified pictorial view illustrations showing a cutting tooth of the bone removal device shown in FIG. 34 from two opposite ends; and to FIG. 38, which is a simplified pictorial illustration of a hinge of the bone removal device shown in FIG. 34.

It is appreciated that the bone material removal device 4004 is similar to the described in Applicant's co-pending application PCT/IL2014/050381, which is hereby incorporated by reference in its entirety, and will be briefly described hereinbelow for clarity.

Bone material removal device 4004 is seen in FIGS. 34-38. The bone material removal device 4004 includes an expandable distal portion 4020, according to some embodiments of the invention.

The bone material removal device 4004 preferably includes a distal tip 4022, a shaft 4024, and a proximal end 4026.

The distal portion 4020 of the bone material removal device 4004 preferably includes a single cutting tooth 4028. It is appreciated that the distal portion 4020 optionally includes a plurality of cutting teeth 4028.

It is a particular feature of some embodiments of the present invention that the cutting tooth 4028 extends from the outer circumference of the shaft 4024 both in closed configuration and in open configuration.

In an exemplary embodiment of the present invention, centrifugal force and/or friction force between the cutting tooth 4028 and a portion of the bone cause the expandable portion 4020 to open and thus the cutting tooth 4028 is extended further from the longitudinal shaft 4024.

In some embodiments, the bone material removal device is adapted for two operational configurations. In the first configuration, the cutting tooth 4028 remains in a closed position in which the tooth 4028 only slightly extends from the circumference of shaft 4024. In the second configuration, the cutting tooth 4028 is in an open position and extends to a greater radial extent from the circumference of shaft 4024, this second configuration is configured for drilling in a retrograde direction.

In some embodiments, the first operational configuration is used for drilling a bore in a bone. Optionally, drilling is performed by attaching proximal end 4026 of the bone material removal device 4004 to a drill motor (not shown). In some embodiments, the first configuration is used for passing the device through an existing bore, optionally without rotation.

In some embodiments, the second operational configuration is used for widening at least a portion of a bore in a bone. In some embodiments, the cutting tooth 4028 extends externally from the shaft 4024, for example extending perpendicularly to a main axis of the shaft. In some embodiments, when cutting tooth 4028 is extended to an open configuration, it enables increasing a diameter of at least one section of the distal portion 4020.

In some embodiments, a user may selectively choose the operational configuration, for example by choosing the direction of rotation of the device. In some embodiments, when rotating in one direction, for example in a clockwise direction, the cutting tooth 4028 remains adjacent to the shaft 4024 in a closed configuration (that is, frictional force does not assist in deploying the cutting tooth). Additionally and/or alternatively, when rotating in the opposite direction, such as a counterclockwise direction, centrifugal force along with friction force of the bone causes the cutting tooth 4028 to further extend beyond the circumference of shaft 4024.

In some embodiments, the cutting tooth 4028 is connected to the shaft 4024, for example connected using a hinge 4030.

In some embodiments, shaft 4024 includes a recess 4032 within the distal portion 4020 of shaft 4024 for insertion of the cutting tooth 4028 and a cover 4034 therein.

The cover 4034 is shaped such that its outer dimensions preferably correspond to the circumference of the shaft 4024 of the bone material removal device 4004. The cover 4034 has a proximal end 4036 and a distal end 4038. A recess 4040 is formed in the distal end 4038 of the cover 4034 for insertion of the hinge 4030 therein. A longitudinally extending bore 4042 is formed within recess 4040.

In accordance with an embodiment of the present invention, the bone material removal device 4004 is cannulated, thus defining a through-bore 4050 configured for insertion of a longitudinal medical instrument; for example a K-wire 4006.

In some embodiments, the device 4004 comprises a plurality of depth-indicating markings denoted on the circumference thereof.

The bone material removal device 4004 is utilized in such a way that a bore is formed in the bone of a patient while the cutting tooth 4028 is positioned in the closed position by means of advancing the bone material removal device 4004 in a forward direction. Further, the direction of rotation of the bone material removal device 4004 is reversed to an opposite direction, the friction force of the bone and the centrifugal force created acts on cutting tooth 4028 so that it extends outwardly from the shaft 4024, such as by pivoting on hinge 4030. In some embodiments, at this point, the device is pulled backwards in a retrograde manner, such as back into the drilled bore.

It is particularly seen in FIGS. 35A-35B that the cover 4034 is inserted into the recess 4032 of the bone material removal device 4004 and the hinge 4030 has a proximal end 4052 inserted into bore 4042 of the cover 4034 and a distal end 4054 inserted into the bore 4050 formed within the bone material removal device 4004.

It is appreciated that the length of hinge 4030 is such that both the proximal end 4052 and the distal end 4054 of the hinge 4030 extend substantially into the bone material removal device 4004 and are firmly held therewithin.

It is a particular feature of some embodiments of the present invention that the aforementioned assembly of bone material removal device 4004 and cutting tooth 4028 using a hinge pin 4030 enables secure pivotable connection between the bone material removal device 4004 and the cutting tooth 4028. Due to insertion of the hinge 4030 into the recess 4040 formed in the cover 4034 and the fact that the hinge 4030 is firmly held at both of its ends within the bone material removal device 4004, the cutting tooth 4028 is securely held in the recess 4032 of the bone material removal device 4004 and cannot be removed therefrom.

It is appreciated that increasing the length of the hinge 4030 potentially increases the force that may be exerted on the bone material removal device 4004 without resulting in breaking of the hinge 4030.

Figure 39A:
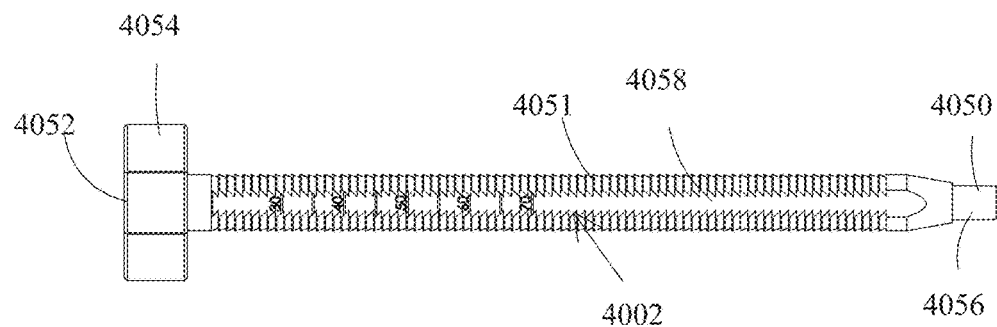
FIGS. 39A-39C are respective simplified two elevation views and a sectional view of a cannula which is forming part of the kit including a guiding system and a bone material removal device shown in FIG. 31, section being taken along lines C-C in FIG. 39B, according to some embodiments of the invention.
Figure 39B:
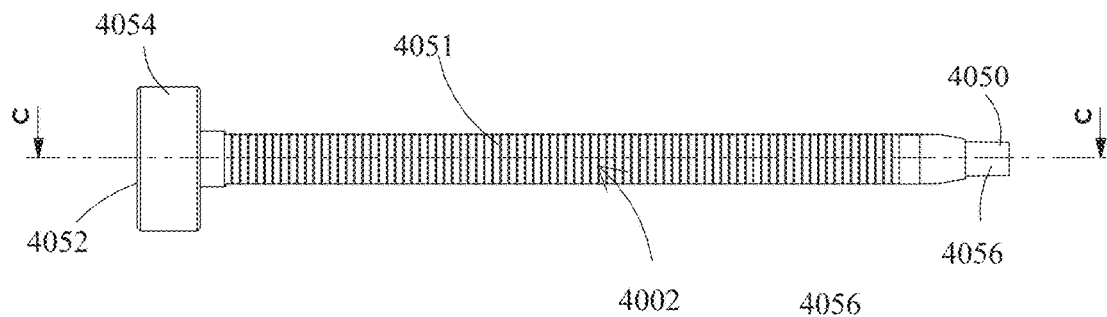
Figure 39C:
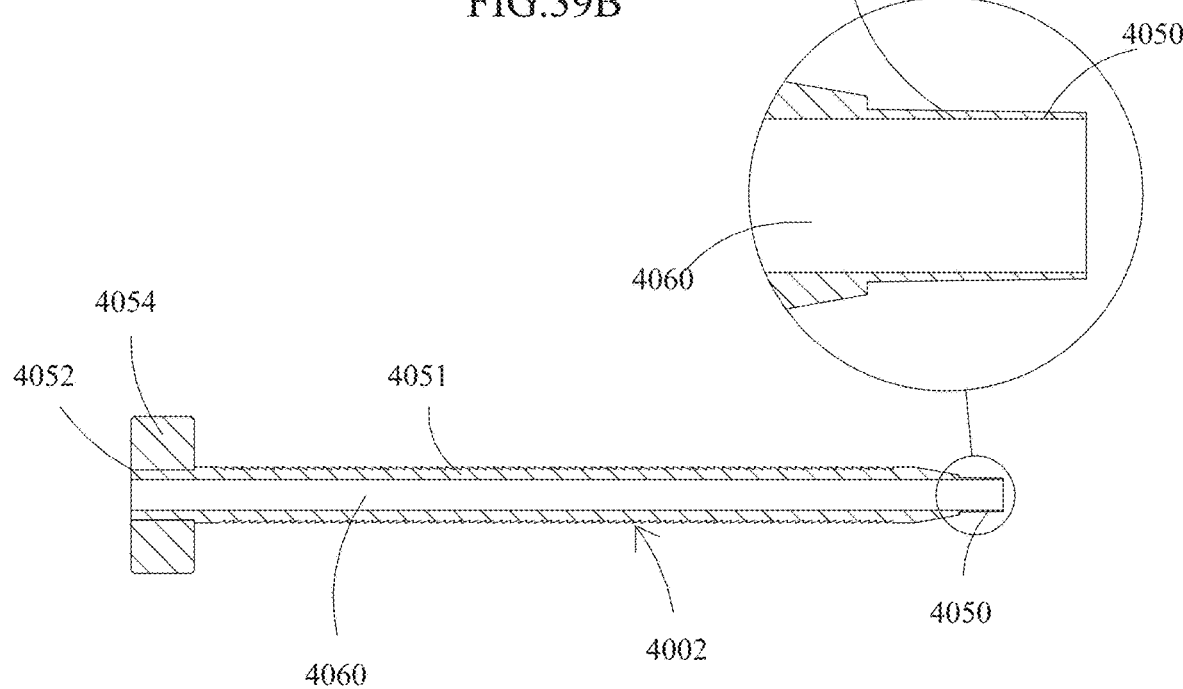

Reference is now made to FIGS. 39A-39C, which, respectively, are simplified two elevation views and a sectional view of cannula 4002 which forms part of the kit 4000 including a guiding system and a bone material removal device 4004 shown in FIG. 31, section being taken along lines C-C in FIG. 39B.

It is seen in FIGS. 39A-39C that cannula 4002 is formed as an integrally made generally hollow cylindrical element having a distal end 4050, an intermediate portion 4051, and a proximal end 4052. A radially extending annular flange 4054 is formed at the proximal end 4052 of cannula 4002 and is used as a stopper for relative slideable movement between the cannula 4002 and the arc 4008.

The distal end 4050 of cannula 4002 has a relatively narrow cylindrical portion 4056 configured for fixation relative the bone of a patient. In some embodiments, fixation is to a depth, for example, of about 7 mm, optionally limited by a widening which terminates the proximal side of the narrow cylindrical portion 4056.

The intermediate portion 4051 preferably has an outer ratcheted surface, oriented to advance in the distal direction by pressure, but locked by the ratchet mechanism against retreat, for so long as the ratchet is engaged. Optionally, marking scales are denoted on the outer surface as well. Optionally, there are two generally flat surfaces 4058 on the intermediate portion 4051. Optionally this allows disengagement of the cannula 4002 from ratcheted engagement with the arc 4008 by means of rotation and thereafter axial displacement of the cannula 4002 relative to the arc 4008.

In some embodiments, a through bore 4060 is formed within the cannula 4002.

Figure 40C:
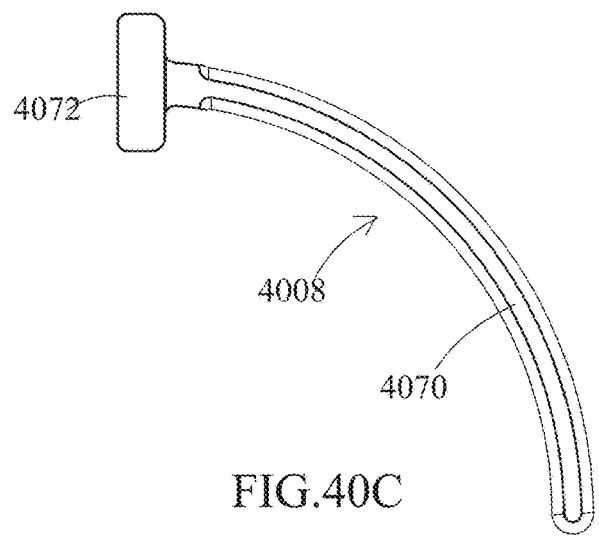
FIGS. 40A-40C are respective simplified three elevation views of an arc which is forming part of the kit including a guiding system and a bone material removal device shown in FIG. 31, according to some embodiments of the invention.
Figure 40B:
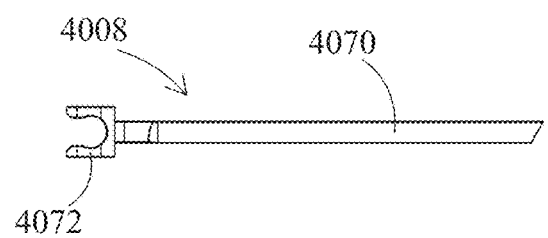
Figure 40A:
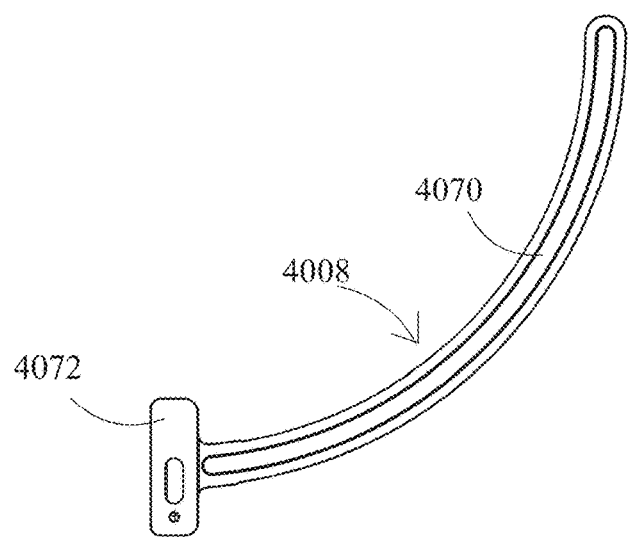

Reference is now made to FIGS. 40A-40C, which, respectively, are three simplified elevation views of arc 4008, which is forming part of the kit 4000 including a guiding system and a bone material removal device 4004 shown in FIG. 31.

It is seen in FIGS. 40A-40C that the arc 4008 is an integrally made element having an arcuate portion 4070 and a holding portion 4072, preferably integrally made therewith. Alternatively, the holding portion 4072 is attached to the arcuate portion 4070. The holding portion 4072 is configured for slideable engagement with the intermediate portion 4051 of cannula 4002, optionally convertible to and from ratcheted engagement, for example, upon a partial rotation of the cannula.

Figure 41C:
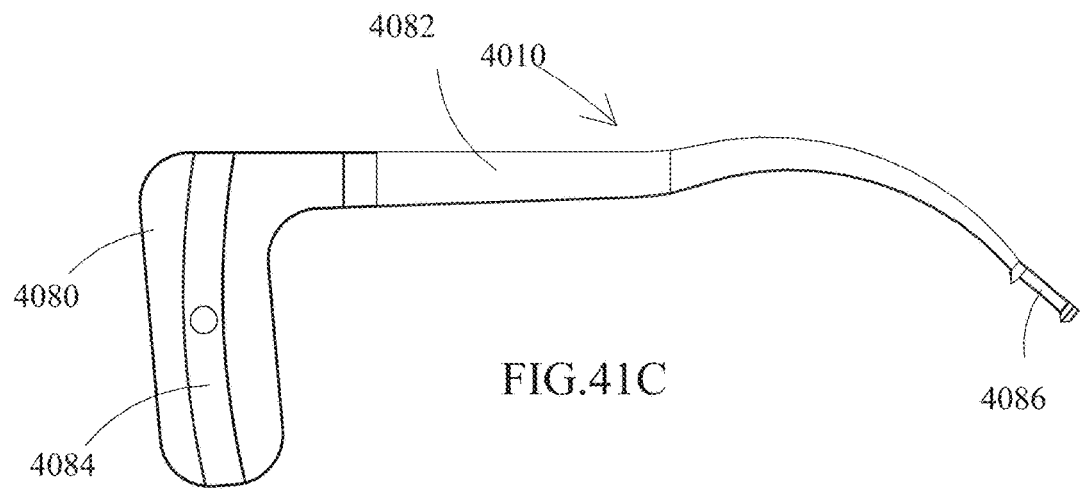
FIGS. 41A-41C are respective simplified three elevation views of a left femoral guide, which is optionally forming part of the kit including a guiding system and a bone material removal device shown in FIG. 31, according to some embodiments of the invention.
Figure 41B:
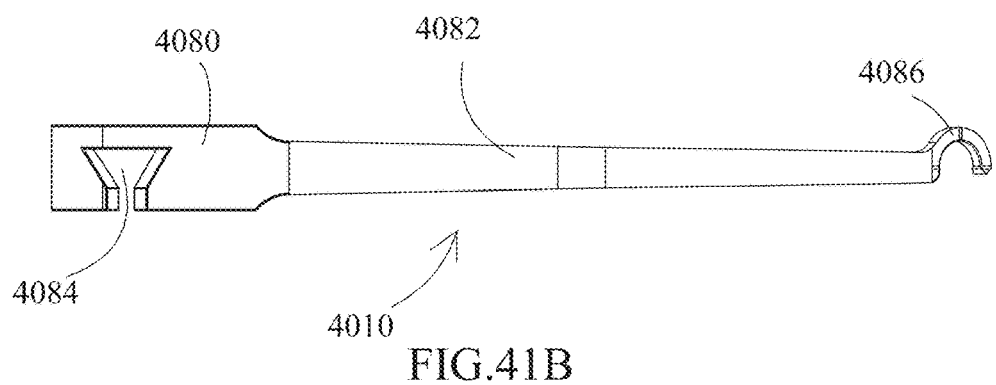
Figure 41A:
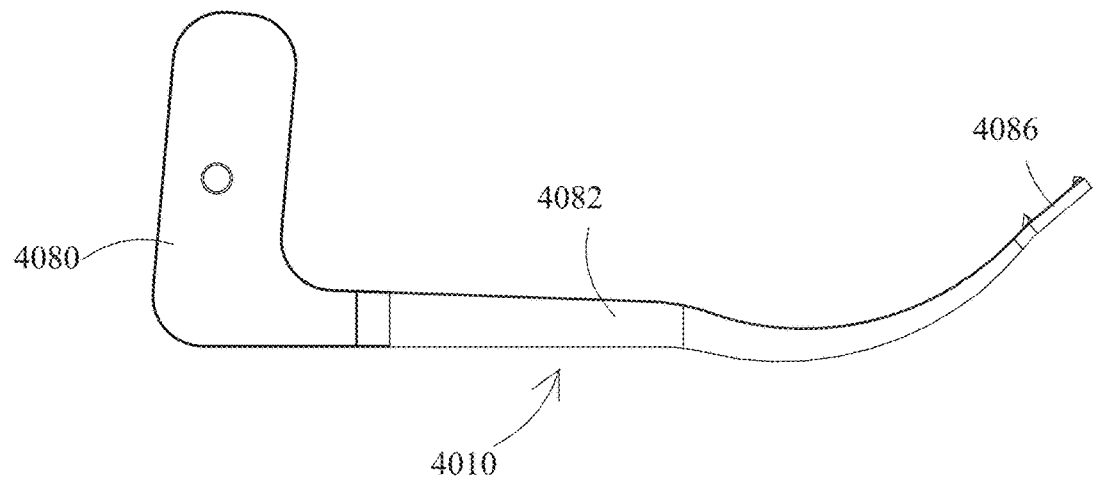

Reference is now made to FIGS. 41A-41C, which are respective simplified three elevation views of left femoral guide 4010, which is optionally forming part of the kit 4000 including a guiding system and a bone material removal device 4004 shown in FIG. 31.

As seen in FIGS. 41A-41C, left femoral guide 4010 is an integrally formed element having a holding portion 4080 and a guiding portion 4082 integrally formed therewith. The holding portion 4080 has a longitudinally extending groove 4084 for enabling slideable engagement of the holding portion 4080 with the arcuate portion 4070 of arc 4008. The guiding portion 4082 preferably has a left-oriented hook element 4086.

Alternatively, the holding portion 4080 can be attached to the guiding portion 4082.

Figure 42C:
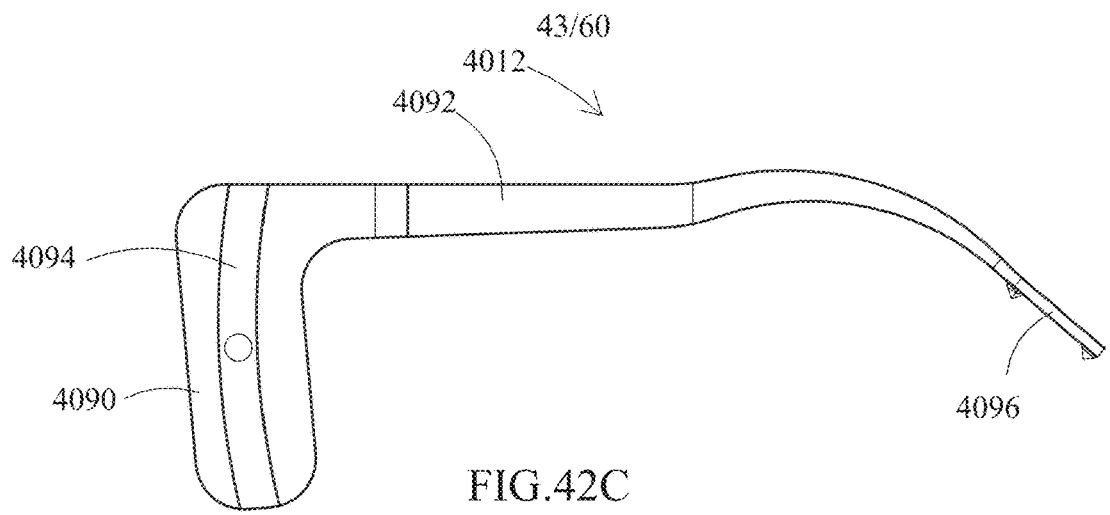
FIGS. 42A-42C are respective simplified three elevation views of a right femoral guide, which is optionally forming part of the kit including a guiding system and a bone material removal device shown in FIG. 31, according to some embodiments of the invention.
Figure 42B:
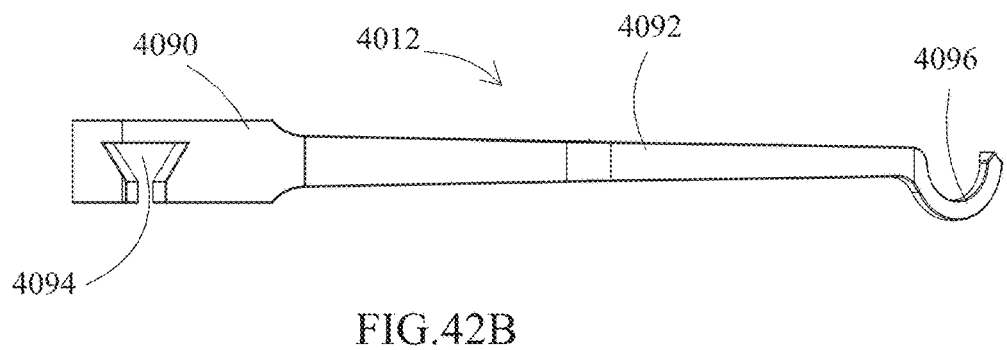
Figure 42A:
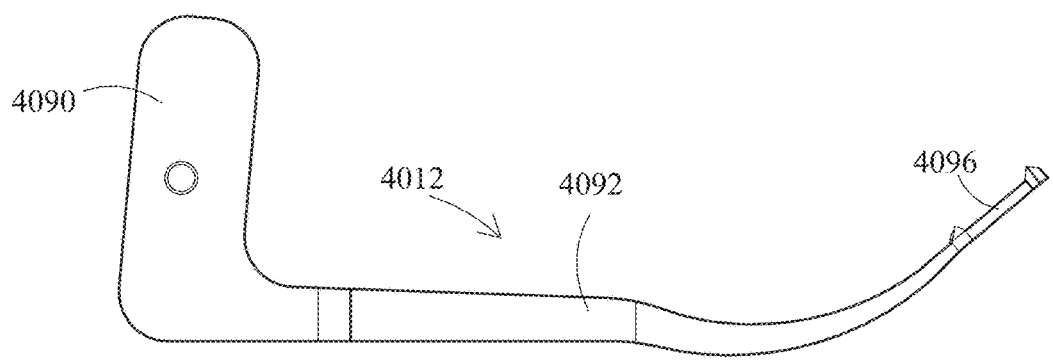

Reference is now made to FIGS. 42A-42C, which are respective simplified three elevation views of right femoral guide 4012, which is optionally forming part of the kit 4000 including a guiding system and a bone material removal device 4004 shown in FIG. 31.

As seen in FIGS. 42A-42C, right femoral guide 4012 is an integrally formed element having a holding portion 4090 and a guiding portion 4092 integrally formed therewith. The holding portion 4090 has a longitudinally extending groove 4094 for enabling slideable engagement of the holding portion 4090 with the arcuate portion 4070 of arc 4008. The guiding portion 4092 preferably has a right-oriented hook element 4096. Optionally, the hook element forms a hollow which is sized to accommodate the diameter of the distal end of the bone material removal device.

Alternatively, the holding portion 4090 can be attached to the guiding portion 4092.

Figure 43C:
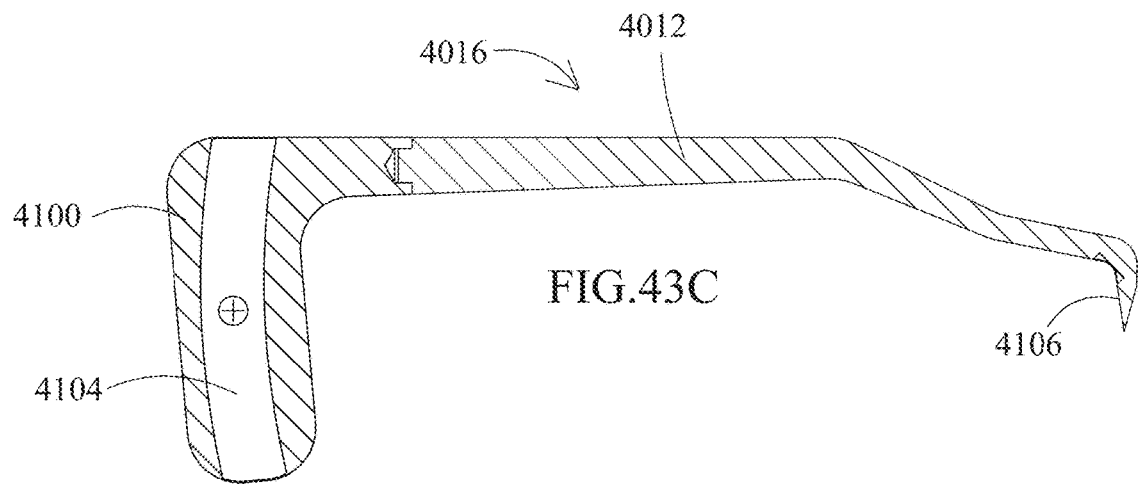
FIGS. 43A-43C are respective simplified three elevation views of a right tibial guide, which is optionally forming part of the kit including a guiding system and a bone material removal device shown in FIG. 31, according to some embodiments of the invention.
Figure 43B:
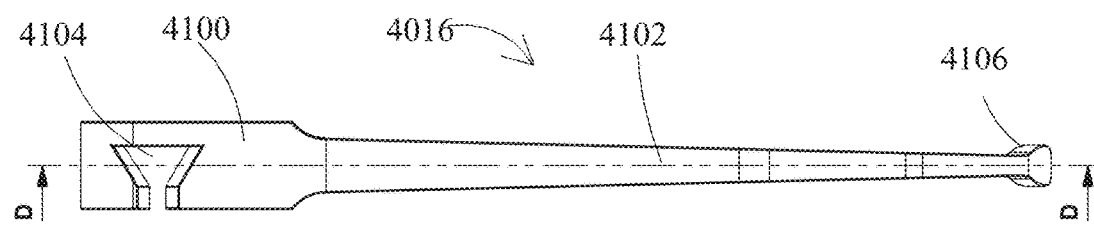
Figure 43A:
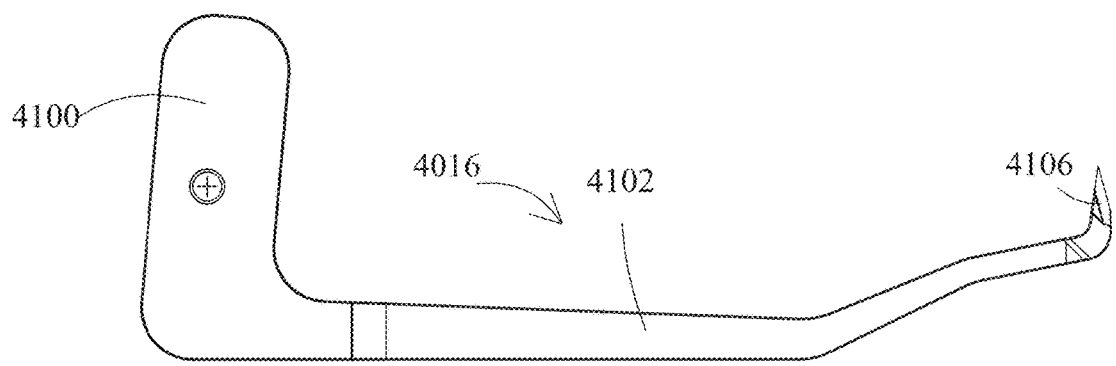

Reference is now made to FIGS. 43A-43C, which are, respectively, three simplified elevation views of right tibial guide 4016, which is optionally forming part of the kit 4000 including a guiding system and a bone material removal device 4004 in FIG. 31.

As seen in FIGS. 43A-43C, right tibial guide 4016 is an integrally formed element having a holding portion 4100 and a guiding portion 4102 integrally formed therewith. The holding portion 4100 has a longitudinally extending groove 4104 for enabling slideable engagement of the holding portion 4100 with the arcuate portion 4070 of arc 4008. The guiding portion 4102 preferably has a right-oriented needle-like element 4106.

Alternatively, the holding portion 4100 can be attached to the guiding portion 4102.

It is appreciated that the left tibial guide is similar in all respects to the right tibial guide 4016, other than the needle-like element 4106 that is left-oriented.

Figure 44A:
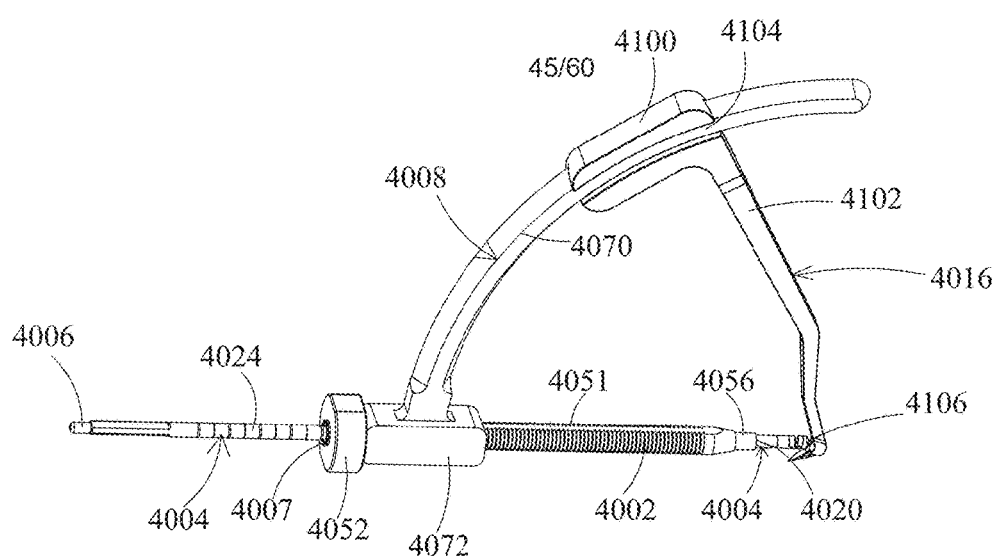
FIG. 44A is a simplified pictorial illustration of an assembled kit including a right tibial guide and a bone material removal device, according to some embodiments of the invention.
Figure 44B:
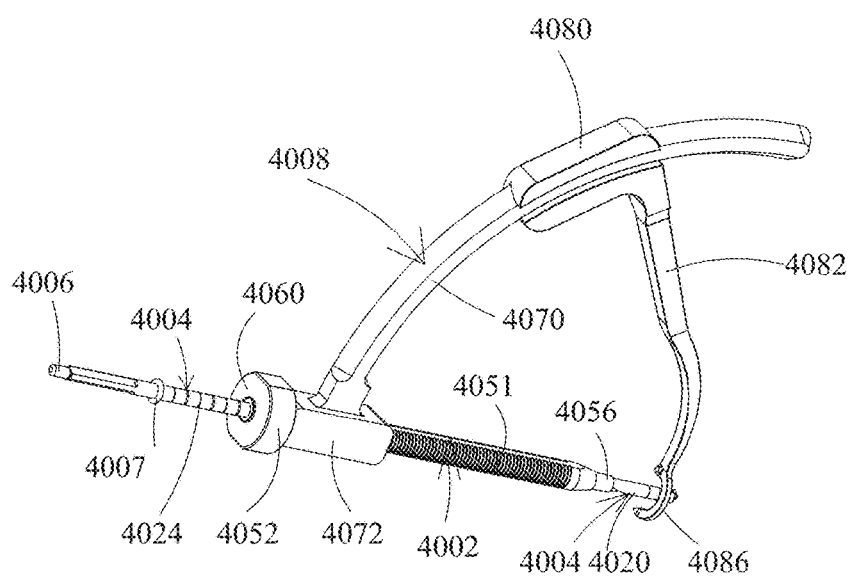
FIG. 44B is a simplified pictorial illustration of an assembled kit including a left femoral guide and a bone material removal device, according to some embodiments of the invention.
Figure 44C:
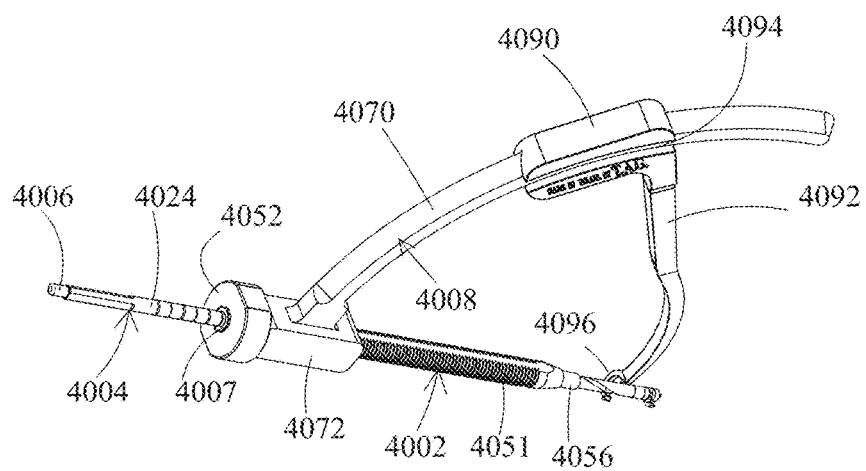
FIG. 44C is a simplified pictorial illustration of an assembled kit including a right femoral guide and a bone material removal device, according to some embodiments of the invention.

Reference is now made to FIG. 44A, which is a simplified pictorial illustration of an assembled kit including a right tibial guide 4016 and a bone material removal device 4004; to FIG. 44B, which is a simplified pictorial illustration of an assembled kit including a left femoral guide 4010 and a bone material removal device 4004; and to FIG. 44C, which is a simplified pictorial illustration of an assembled kit including a right femoral guide 4012 and a bone material removal device 4004.

FIGS. 44A-44C illustrate three different examples of kits including a guide system and a bone material removal device 4004, with right tibial guide 4016, left femoral guide 4010 and right femoral guide 4012 respectively.

In some embodiments, the following spatial relationships exist:

Cannulated bone material removal device 4004 is inserted into the through bore 4060 of cannula 4002, such that the distal end portion 4020 of the bone material removal device 4004 extends distally from the distal end 4056 of cannula 4002. It is appreciated that the cutting tooth 4028 resides in a closed position within the bore 4060 of cannula 4002 and it is allowed to expand once the direction of rotation of the drill is reversed and the distal end portion 4020 of the bone material removal device 4004 extends distally from the distal end 4056 of cannula 4002.

It is a particular feature of an embodiment of the present invention that K-wire 4006 is insertable into bore 4050 of the cannulated bone material removal device 4004. It is additionally seen in FIGS. 44A-44C that the holding portion 4072 of the arc 4008 is slidably attached to the intermediate portion 4051 of the cannula 4002. The flange 4052 of the cannula 4002 serves as a stopper for movement of the holding portion 4072 of the arc 4008 over the intermediate portion 4051 of the cannula 4002.

It is specifically seen in FIG. 44A that the holding portion 4100 of right tibial guide 4016 is slidably attached to the arc 4008, by means of insertion of arcuate portion 4070 of the arc 4008 into groove 4104 of the right tibial guide 4016. The needle-like element 4106 of the right tibial guide 4016 is configured to be aligned with the distal tip 4022 of the bone material removal device 4004.

It is specifically seen in FIG. 44B that the holding portion 4080 of left femoral guide 4010 is slidably attached to the arc 4008, by means of insertion of arcuate portion 4070 of the arc 4008 into groove 4084 of the left femoral guide 4010. The left-oriented hook element 4086 of the left femoral guide 4086 is configured to be aligned with the distal tip 4022 of the bone material removal device 4004.

It is specifically seen in FIG. 44C that the holding portion 4090 of right femoral guide 4012 is slidably attached to the arc 4008, by means of insertion of arcuate portion 4070 of the arc 4008 into groove 4094 of the right femoral guide 4012. The right-oriented hook element 4096 of the right femoral guide 4096 is configured to be aligned with the distal tip 4022 of the bone material removal device 4004.

Figure 57:
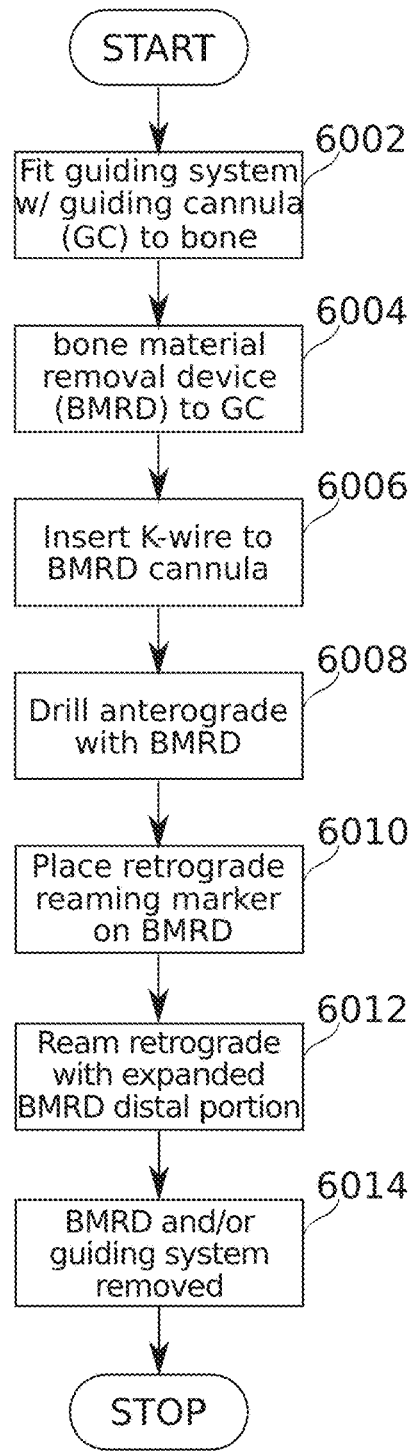
FIG. 57 shows a schematic flowchart of the use of the kit including a guiding system and a bone material removal device shown in FIG. 31, according to some embodiments of the invention.

Reference is now made to FIG. 57, which shows a schematic flowchart of the use of the kit 4000 including a guiding system and a bone material removal device 4004 shown in FIG. 31, according to some embodiments. Some operations of this flowchart correspond, for example, to operations also outlined in FIGS. 45-51.

In some embodiments, a repositionable O-ring 4007 is used to monitor retrograde drilling depth, optionally with respect to a scale marked on the bone material removal device 4004.

At block 6002, in some embodiments, is fitted to a bone 4120, such that a portion of the bone is positioned between the distal end 4056 of the cannula and a terminal arm structure, such as a hook and/or needle element (for example, element 4106, 4086, or 4096) of the guide arm 4010. Optionally, the guiding system comprises arcuate member 4008, cannula 4002, and guide arm 4010. In some embodiments, the cannula 4002 alone is used (however, in this case, operations relating to relative positions of the three parts are skipped and/or substituted with alternative operations).

In some embodiments, the distal end 4056 of the cannula 4002 is positioned against the bone on one side, and the tip/hook of the guide 4010 is near and/or against the bone on the other side. Optionally, the positioning comprises ratchet-sliding the cannula 4002 relative to the holder 4072, locking it into position against the bone. Optionally, the cannula 4002 is driven partially into the bone, for example, by hammering and/or twisting. In some embodiments, this fixes the guiding system relative to the bone in preparation for bone material removal.

At block 6004, in some embodiments, a cannulated bone material removal device 4004 with an expandable distal cutting end is inserted into the bore 4060 of cannula 4002. Optionally, the O-ring 4007 is pre-positioned to serve as a stop on the anterograde movement of the bone material removal device, for example, by reference to scales on the cannula and/or on the bone material removal device.

Optionally, at block 6006, a K-wire 4006 is inserted into the cannula bore 4050 of the bone material removal device 4004. Potentially, this blocks debris from entering the cannula bore 4050 during bone material removal.

At block 6008, in some embodiments, anterograde bone material removal (e.g. drilling in a proximal direction) is performed using the bone material removal device 4004. The advance is optionally stopped by the O-ring 4007 and/or by the terminal structure of guide arm 4010, for example, at some point after the hole completely passes through the bone, and/or when the expandable distal portion of the bone material removal device is advanced sufficiently to cut away material from the end of the tunnel when it deploys.

Optionally, at block 6010, the guide assembly kit 4000 is marked for measurement of a length of retrograde bone material removal from the distal end of the hole just made. In some embodiments (if it has not been so-placed already), an O-ring 4007 is pressed over the bone material removal device to mark a reference position in relation to the distal end of the bone hole. In particular, the reference position comprises a known position of cutting tooth 4028 relative to the distal hole end, which may be determined with reference to the device scales, and/or by having encountered a physical stop. For example, optionally, the position is in part determined by and/or from the position of the tip/hook of guide 4010 relative to the distal tip of the bone material removal device 4004. It should be noted that the O-ring optionally has at least two distinct measurement functions. During anterograde drilling, the O-ring marks a limit of distal movement. During retrograde reaming, the position of the O-ring relative to the cannula proximal end as it is withdrawn gives a distance of retrograde movement which has occurred.

At block 6012, in some embodiments, retrograde (proximally directed) bone material removal is performed. The cutting tooth or teeth 6028 are deployed to their expanded position (for example, by centrifugal force and/or tooth engagement with the existing bore wall while rotating in a direction permitting tooth deployment), and the bone material removal device 4004 is gradually withdrawn while rotating. Movement of the O-ring 4007 is monitored (optionally, by reference to depth-indicating markings denoted on the circumference of the bone material removal device 4004) to determine and/or control the distance of retrograde (bore-widening) drilling which is performed. Optionally, the arc 4008 and/or guide 4010 portions of the guiding system are released (before or after retrograde drilling) by unlocking rotation of the holder 4072 relative to the cannula 4002. In some embodiments, the embedded depth of the distal tip of the cannula 4002 determines a minimal bone bridge thickness, by preventing further withdrawal of the expanded reaming head.

At block 6014, in some embodiments, the K-wire 4006 is optionally replaced with surgical wire 4130. The bone material removal device is removed. Remaining surgical steps of the grafting are optionally performed with one, both, or neither of the cannulated devices 4002, 4004 remaining in place.

Figure 45:
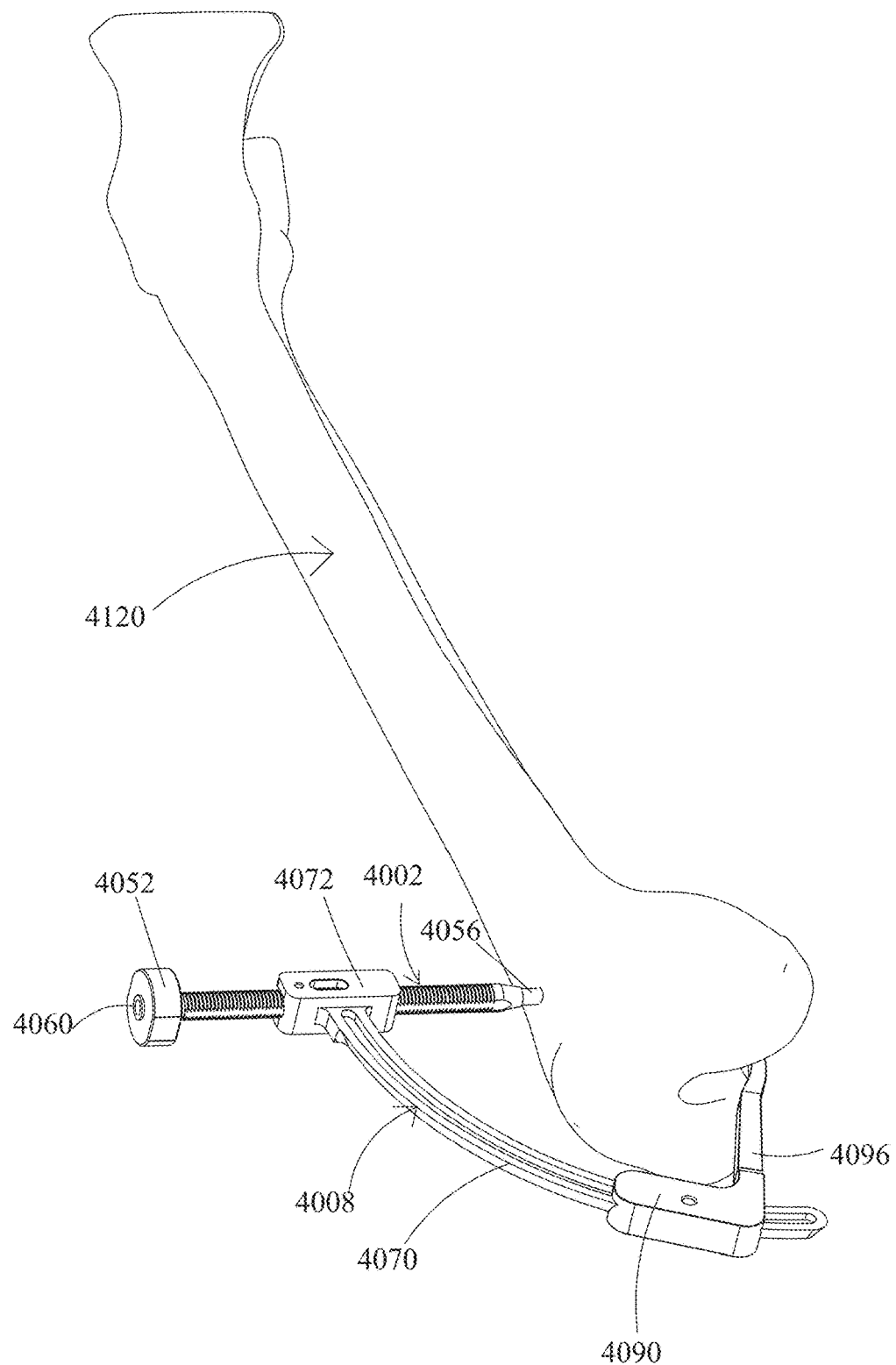
FIG. 45 is a simplified pictorial illustration of the kit including a guiding system and a bone material removal device of FIG. 31 shown in a first operative orientation, where the kit including a guiding system is initially positioned on a bone of a patient, according to some embodiments of the invention.

Reference is now made to FIG. 45, which is a simplified pictorial illustration of the kit 4000 including a guiding system and a bone material removal device 4004 of FIG. 31 shown in a first operative orientation, where the kit including a guiding system is initially positioned on a bone of a patient.

It is seen in FIG. 45 that in the first operative orientation the guiding system including the cannula 4002 attached to the arc 4008, which is in turn attached to the left femoral guide 4010, for example, is positioned over a first surface of bone 4120 of the patient.

In this first operative orientation the bone material removal device 4004 is not yet inserted into the bore 4060 of cannula 4002. In this orientation the cannula 4002 is fixedly positioned in the bone 4120 of the patient, by means of hammering on the flange 4052 of the cannula 4002 in order to partially insert the distal end 4056 of the cannula 4002 into the bone 4120.

It is additionally seen in FIG. 45 that the hook element 4096 is disposed over an opposite surface of the bone 4120, such that the central axis of the hook element 4096 and the longitudinal axis of the cannula 4002 are aligned.

Figure 46:
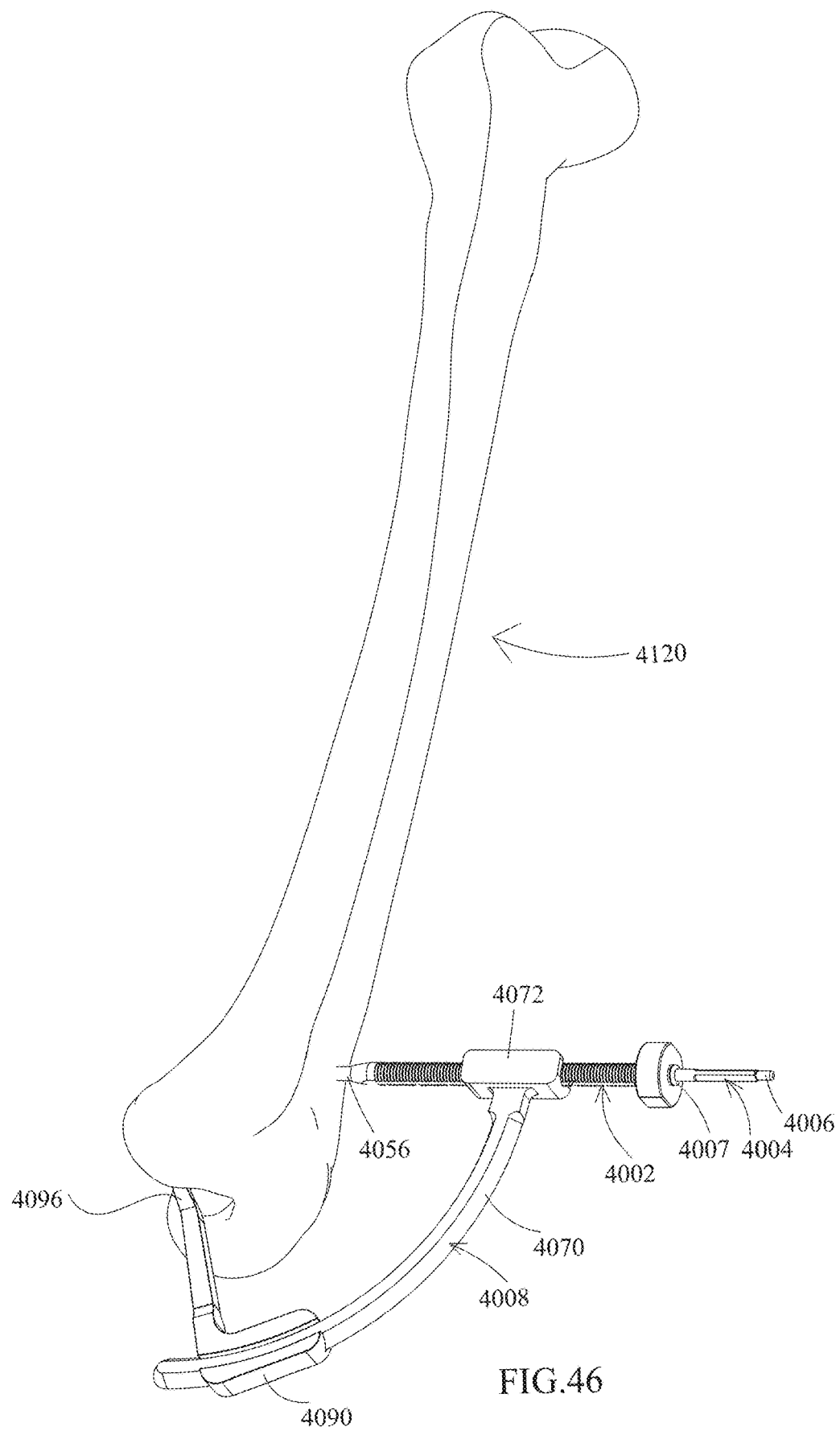
FIG. 46 is a simplified pictorial illustration of the kit including a guiding system and a bone material removal device inserted into the kit of FIG. 31 shown in a second operative orientation, where the kit including a guiding system and a bone material removal device remains positioned on the bone of a patient and the bone material removal device is advanced to drill the bone in a forward direction, according to some embodiments of the invention.

Reference is now made to FIG. 46, which is a simplified pictorial illustration of the kit 4000 including a guiding system and a bone material removal device 4004 of FIG. 31 shown in a second operative orientation, where the kit 4000 including a guiding system and a bone material removal device 4004 remains positioned over the bone 4120 of a patient and the bone material removal device 4004 is advanced to drill the bone 4120 in a forward direction.

It is seen in FIG. 46 that in the second operative orientation the guiding system including the cannula 4002 attached to the arc 4008, which is in turn attached to the left femoral guide 4010, for example, remains positioned over a first surface of bone 4120 of the patient.

In this second operative orientation the bone material removal device 4004 is inserted into the bore 4060 of cannula 4002 and K-wire 4006 is inserted into bore 4050 of the bone material removal device 4004 in order to prevent insertion of debris into the bore 4050 during the drilling process. In this orientation the cannula 4002 is fixedly positioned in the bone 4120 of the patient.

The distal tip 4022 of the bone material removal device 4004 is aligned with the central axis of the hook element 4096.

Figure 47:
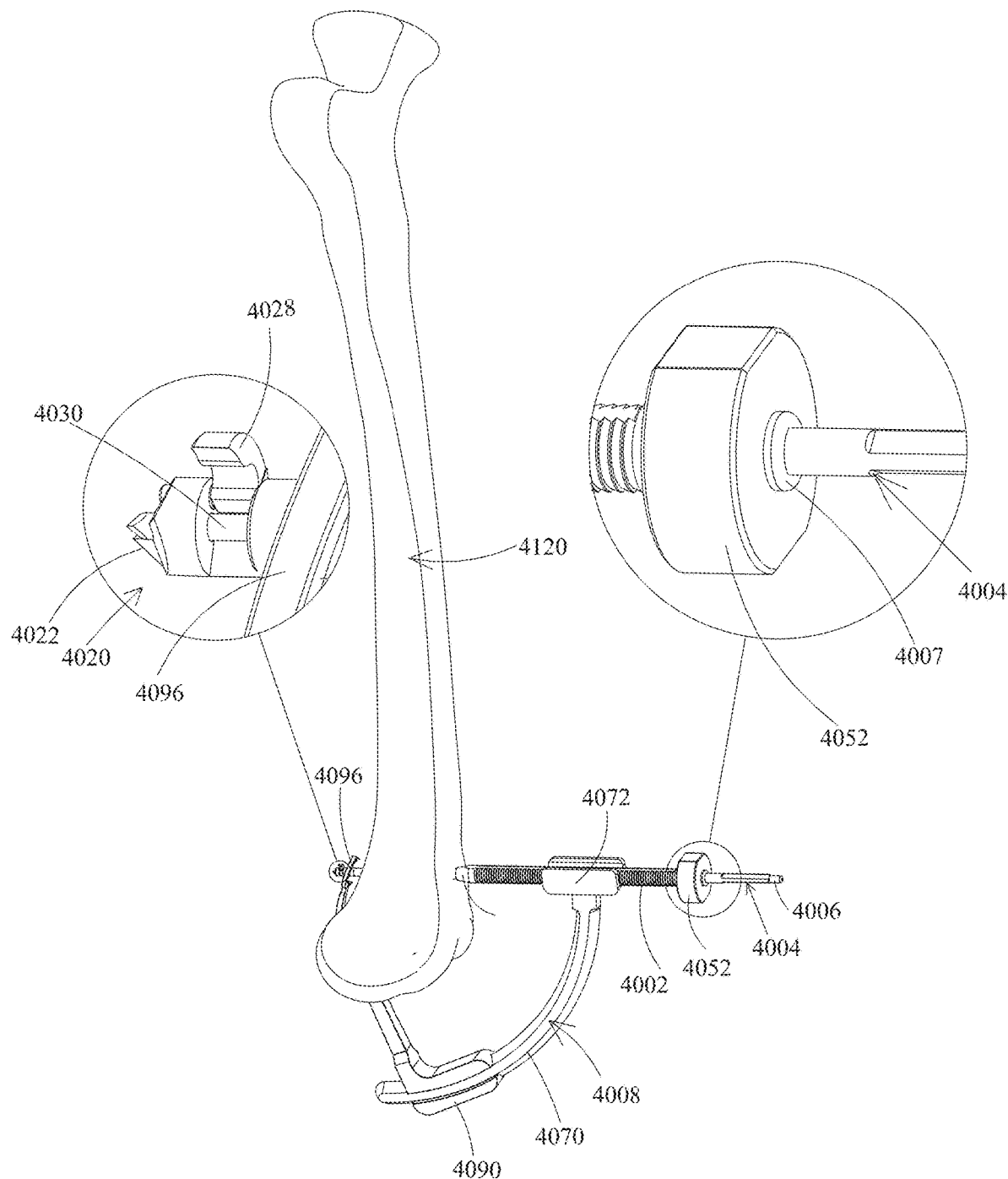
FIG. 47 is a simplified pictorial illustration of the kit including a guiding system and a bone material removal device of FIG. 31 shown in a third operative orientation, where the cutting tooth of the bone material removal device is expanded before retrograde displacement thereof in order to create a larger diameter socket within the bone of a patient, according to some embodiments of the invention.

Reference is now made to FIG. 47, which is a simplified pictorial illustration of the kit including a guiding system and a bone material removal device 4004 of FIG. 31 shown in a third operative orientation, where the cutting tooth 4028 of the bone material removal device 4004 is expanded before retrograde displacement thereof in order to create a larger diameter socket within the bone 4120 of a patient.

It is seen in FIG. 47 that in the third operative orientation the guiding system including the cannula 4002 attached to the arc 4008, which is in turn attached to the left femoral guide 4010, for example, remains positioned over a first surface of bone 4120 of the patient.

In this third operative orientation the bone material removal device 4004 remains within bore 4060 of cannula 4002 and K-wire 4006 is inserted into bore 4050 of the bone material removal device 4004 in order to prevent insertion of debris into the bore 4050 during the drilling process. In this orientation the cannula 4002 remains fixedly positioned in the bone 4120 of the patient.

The bone material removal device 4004 is advanced forwardly to drill a bore of a first diameter through bone 4120 of a patient. At the end of the forward drilling process, the distal tip 4022 of the bone material removal device 4004 extends forwardly through the hook element 4096.

The O-ring 4007 is positioned over the bone material removal device 4004 adjacent the proximal end of flange 4052 in order to enable measurement of the length of socket formed during the following retrograde drilling process.

It is seen in FIG. 47 that the direction of rotation of the bone material removal device 4004 is reversed and the cutting tooth 4028 is expanded and ready for drilling in a retrograde direction to form a bore in the bone 4120, which has a greater diameter than the first bore formed in the bone 4120.

Figure 48:
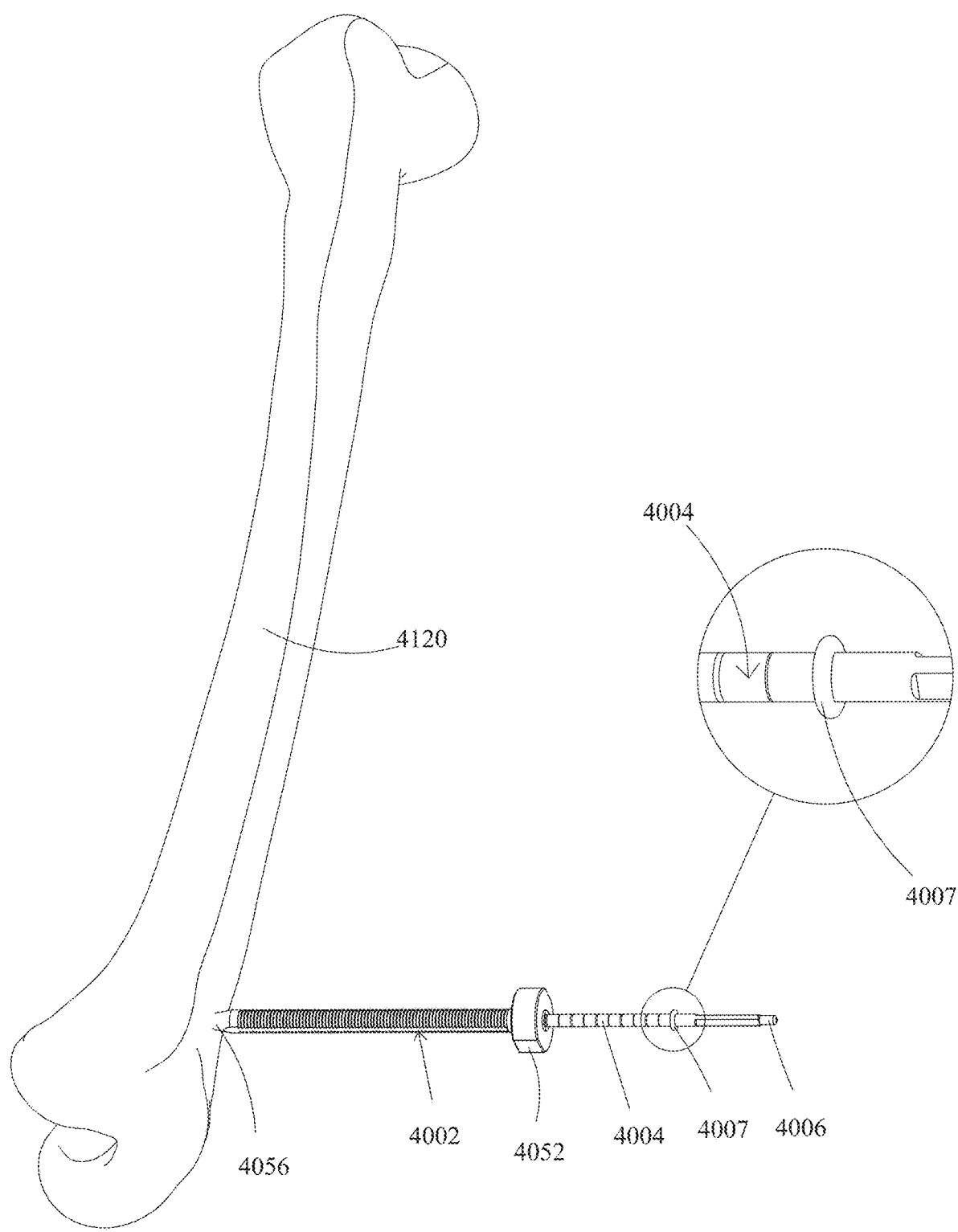
FIG. 48 is a simplified pictorial illustration of the kit including a guiding system and a bone material removal device of FIG. 31 shown in a fourth operative orientation, where the guide and arc are removed and the cannula accommodating the bone material removal device is further positioned on the bone of a patient, according to some embodiments of the invention.

Reference is now made to FIG. 48, which is a simplified pictorial illustration of the kit 4000 including a guiding system and a bone material removal device 4004 of FIG. 31 shown in a fourth operative orientation, where the guide 4010 and arc 4008 are removed and the cannula 4002 accommodating the bone material removal device 4004 is further positioned on the bone 4120 of a patient.

It is seen in FIG. 48 that in the fourth operative orientation, the arc 4002 and the left femoral guide 4010 are removed. The holding portion 4072 of the arc 4008 is disengaged from the cannula 4002 due to rotation of the arc 4008 relative the cannula 4002 such that the flat surfaces 4058 of the cannula 4002 permit releasing the holding portion 4072 of the arc 4008.

In this fourth operative orientation the bone material removal device 4004 remains within bore 4060 of cannula 4002 and K-wire 4006 remains inserted into bore 4050 of the bone material removal device 4004 in order to prevent insertion of debris into the bore 4050 during the drilling process. In this orientation the cannula 4002 remains fixedly positioned in the bone 4120 of the patient.

The bone material removal device 4004 has completed the drilling in a retrograde direction. At the end of the retrograde drilling process, the distal tip 4022 of the bone material removal device 4004 is disposed within the bone 4120 of a patient.

The O-ring 4007 is positioned over the bone material removal device 4004 at the same location relative the bone material removal device 4004, however it is now rearward-spaced from the flange 4052 in comparison with FIG. 47. The distance between the flange 4052 of cannula 4002 and the O-ring 4007 represents the length of the socket formed during the drilling in a retrograde direction.

Figure 49:
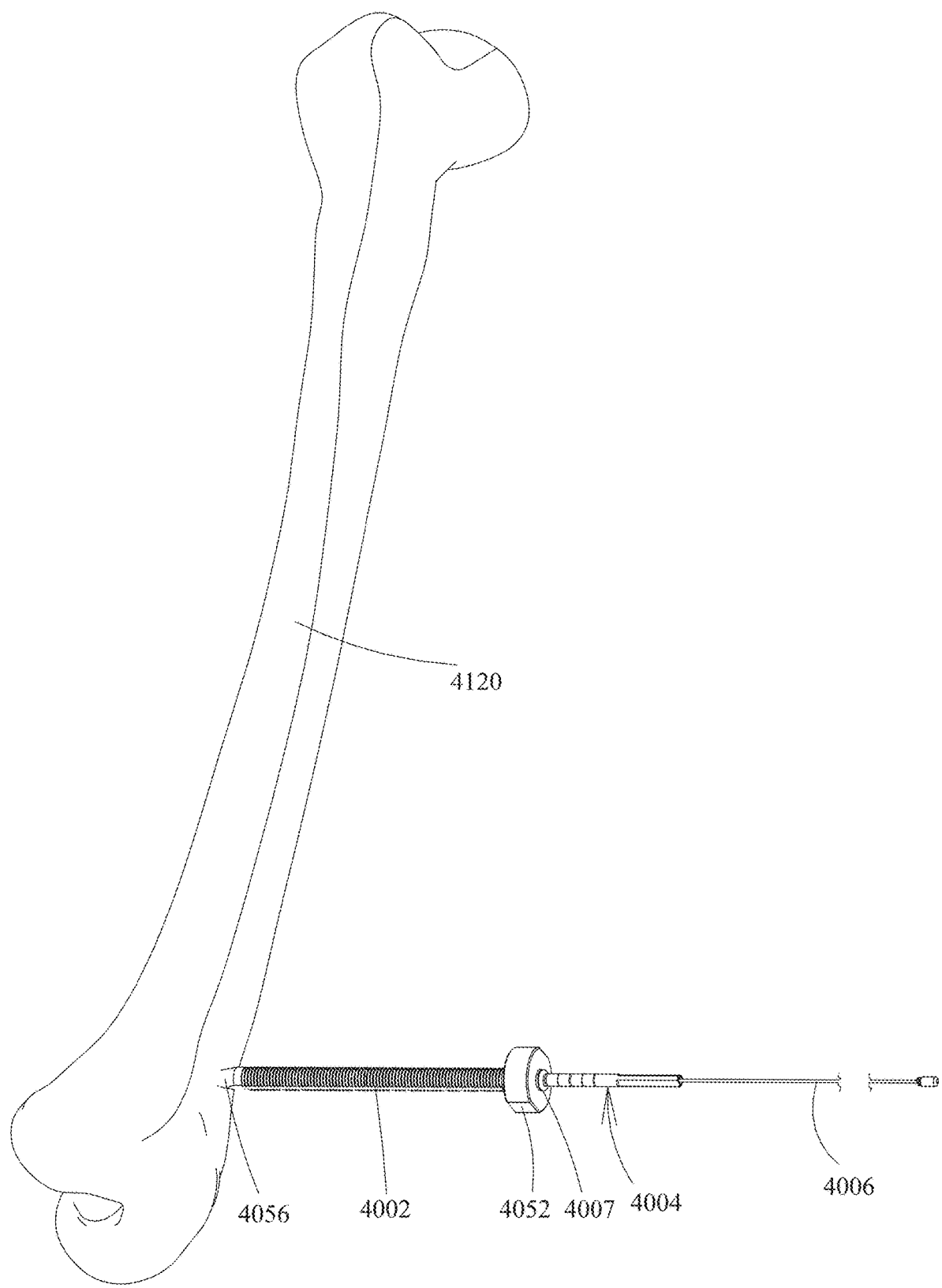
FIG. 49 is a simplified pictorial illustration of the kit including a guiding system and a bone material removal device of FIG. 31 shown in a fifth operative orientation, where the guide and arc are removed and the cannula accommodating the bone material removal device is further positioned on the bone of a patient, and the K-wire is being removed from the bone material removal device, according to some embodiments of the invention.

Reference is now made to FIG. 49, which is a simplified pictorial illustration of the kit 4000 including a guiding system and a bone material removal device 4004 of FIG. 31 shown in a fifth operative orientation, where the guide 4010 and arc 4008 are removed and the cannula 4002 accommodating the bone material removal device 4004 is further positioned on the bone 4120 of a patient, and the K-wire 4006 is removed from the bone material removal device 4004.

It is seen in FIG. 49 that in the fifth operative orientation, the arc 4002 and the left femoral guide 4010 are removed.

In this fifth operative orientation the bone material removal device 4004 remains within bore 4060 of cannula 4002 and K-wire 4006 is being removed out of bore 4050 of the bone material removal device 4004 in order to allow insertion of surgical wire through bore 4050 of the bone material removal device 4004. In this orientation the cannula 4002 remains fixedly positioned in the bone 4120 of the patient.

The bone material removal device 4004 is advanced forwardly such that the O-ring 4007 is positioned again adjacent the flange 4052. This positioning assures that the distal tip 4022 of the bone material removal device 4004 is positioned at the end of the socket having the greater diameter and the surgical wire can be leaded through bore 4050 of the bone material removal device 4004 to the exact location of the drilled bore in the bone 4120 of a patient.

It is appreciated that there is an advantage in leading the surgical wire through the bore 4050 of the bone material removal device 4004 rather than through the bore 4060 of the cannula 4002, since the bone material removal device 4004 leads the surgical wire to the exact location of the drilled bore in the bone 4120 of a patient.

Figure 50:
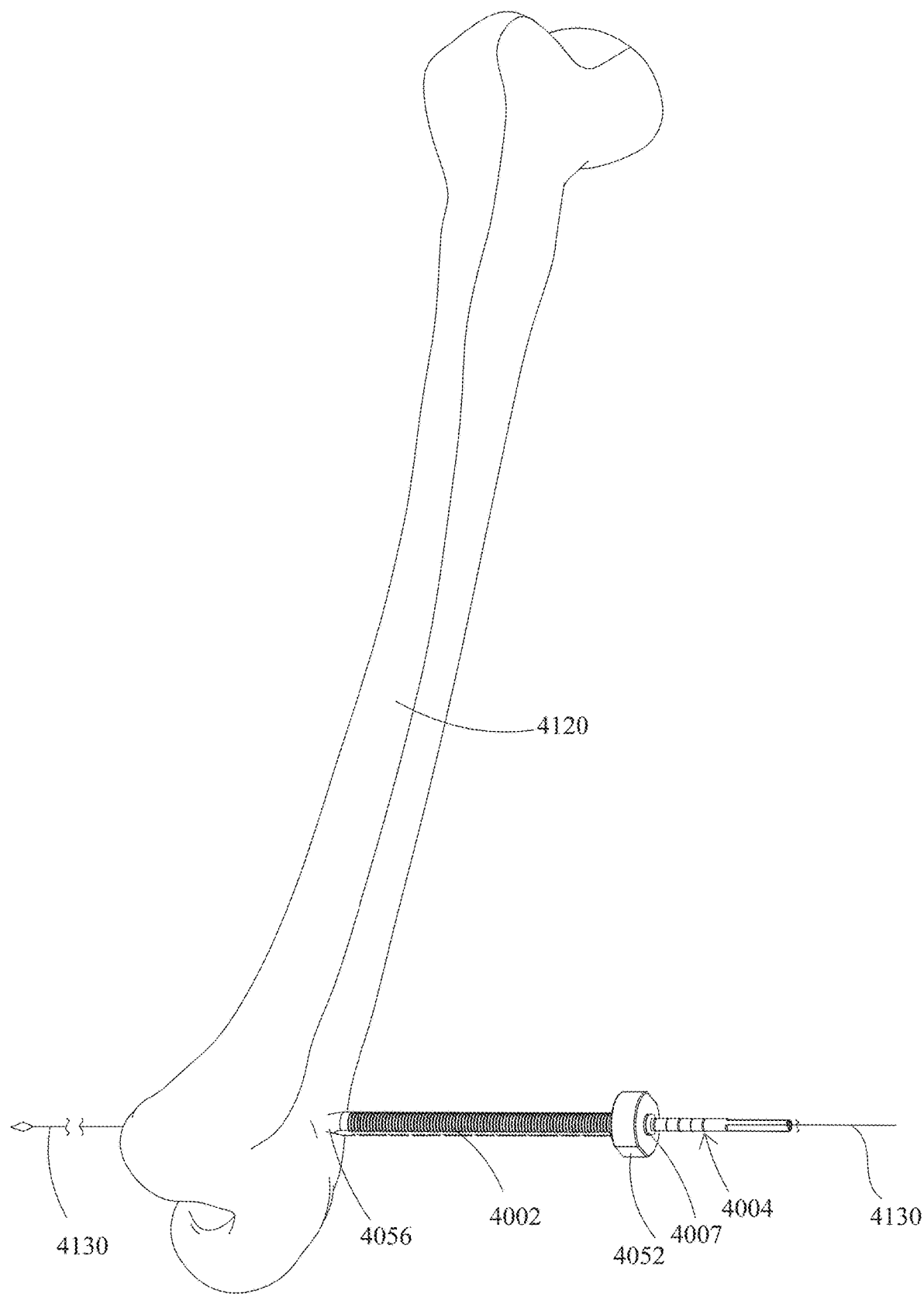
FIG. 50 is a simplified pictorial illustration of the kit including a guiding system and a bone material removal device of FIG. 31 shown in a sixth operative orientation, where a nitinol wire is inserted through the bone material removal device, which is positioned in the bone of a patient, according to some embodiments of the invention.

Reference is now made to FIG. 50, which is a simplified pictorial illustration of the kit 4000 including a guiding system and a bone material removal device 4004 of FIG. 31 shown in a sixth operative orientation, where a nitinol wire 4130 is inserted through the bone material removal device 4004, which is positioned in the bone 4120 of a patient.

It is seen in FIG. 50 that in the sixth operative orientation the bone material removal device 4004 remains within bore 4060 of cannula 4002 and a nitinol wire 4130 is inserted through bore 4050 of the bone material removal device 4004 and extends forwardly from the second surface of bone 4120. In this orientation the cannula 4002 remains fixedly positioned in the bone 4120 of the patient.

It is appreciated that the graft can be passed through the bone material removal device 4004 and the ACL reconstruction can be performed without removing the bone material removal device 4004 from the bone 4120 due to the fact that it is cannulated.

Figure 51:
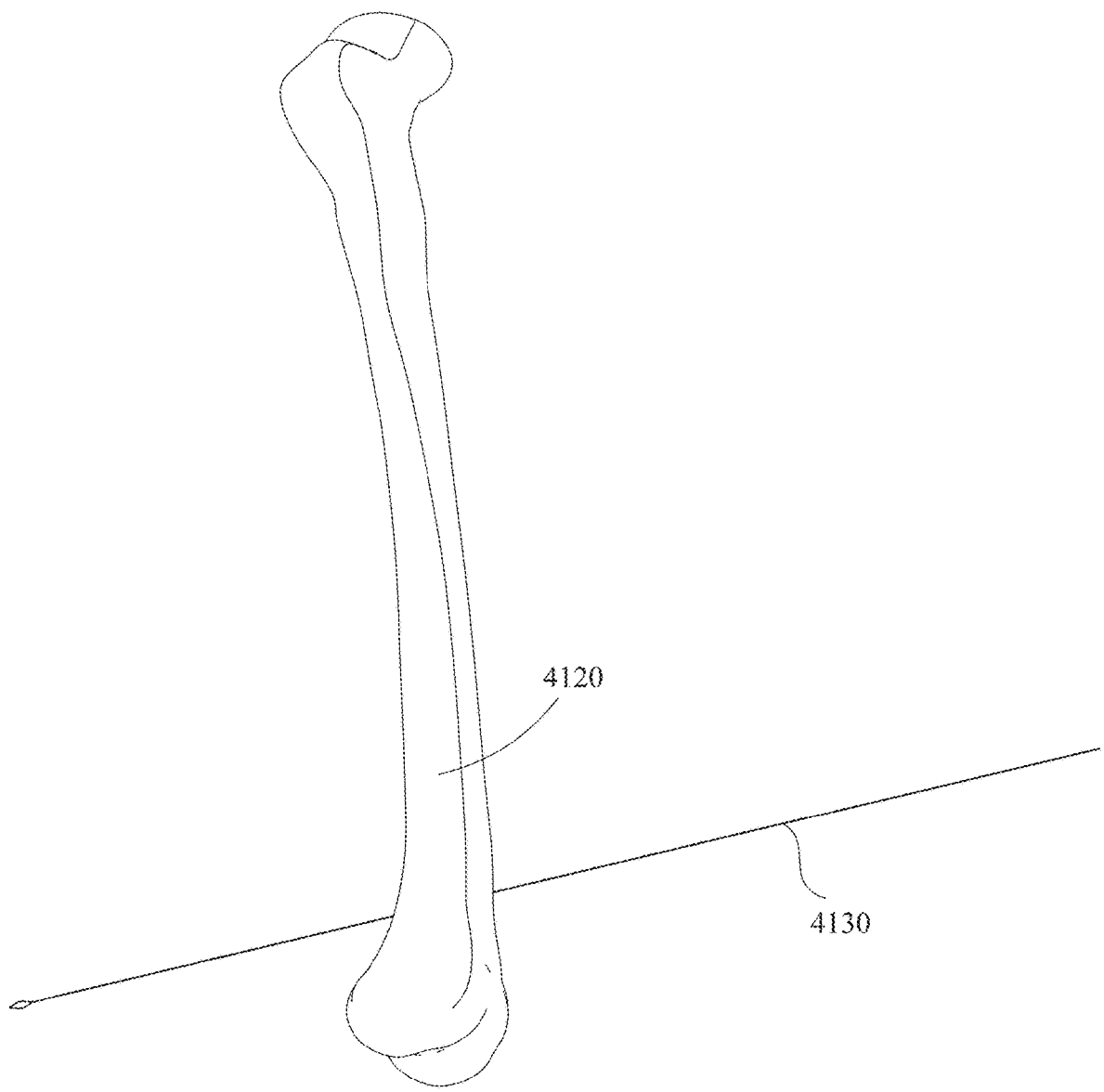
FIG. 51 is a simplified pictorial illustration of the kit including a guiding system and a bone material removal device of FIG. 31 shown in a seventh operative orientation, where a nitinol wire extends through the bone and the kit including a guiding system and a bone material removal device is removed from the bone of the patient, according to some embodiments of the invention.

Reference is now made to FIG. 51, which is a simplified pictorial illustration of is the kit 4000 including a guiding system and a bone material removal device 4004 of FIG. 31 shown in a seventh operative orientation, where the nitinol wire 4130 extends through the bone 4120 and the kit 4000 including a guiding system and a bone material removal device 4004 is removed from the bone 4120 of the patient.

It is seen in FIG. 51 that in a final seventh operative orientation, the nitinol wire, preferably with a graft threaded thereon, is inserted into the desired position within the bone 4120 of a patient and the bone material removal device 4004 is removed.

Figure 52:
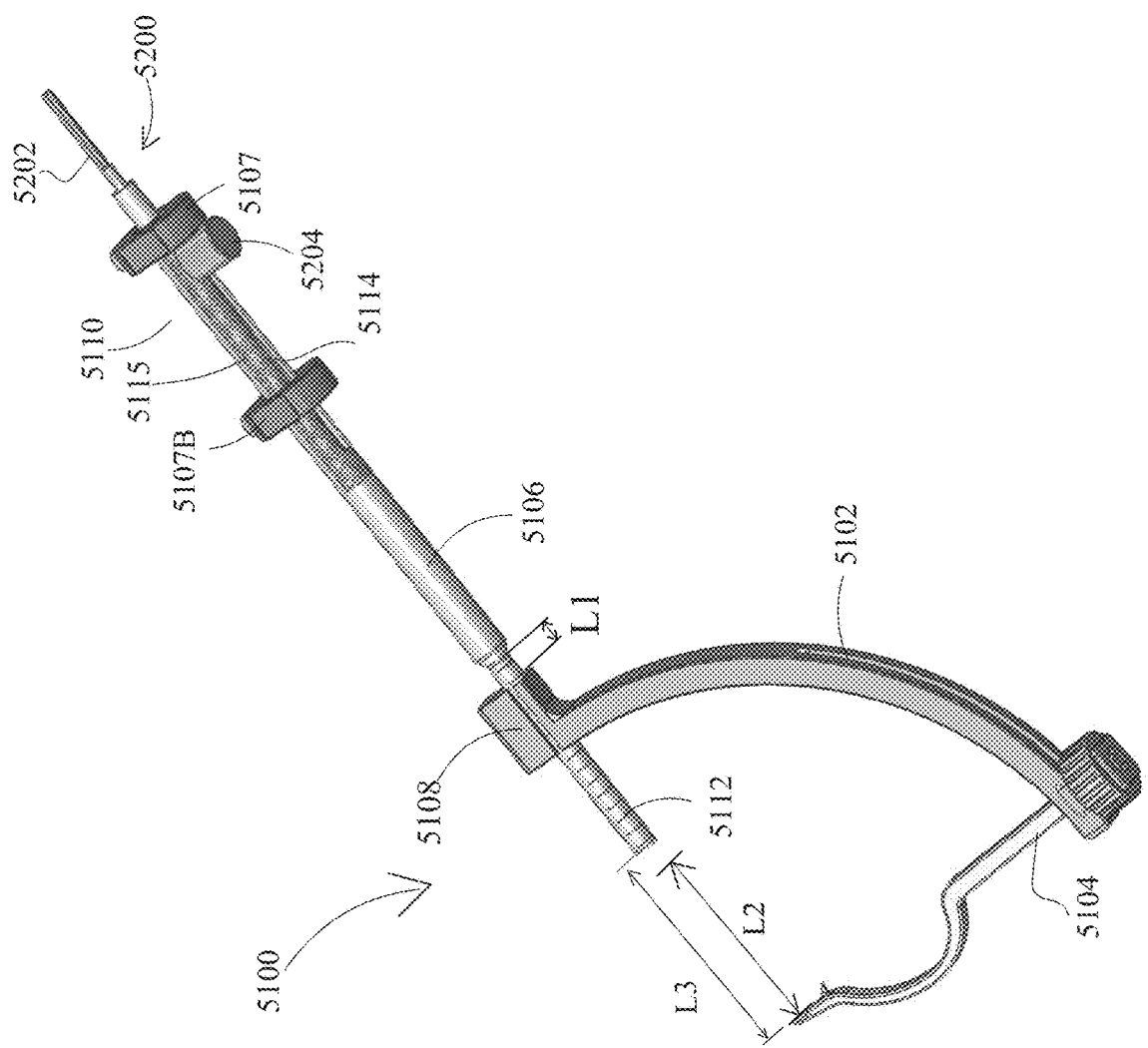
FIG. 52 is a simplified pictorial view illustration of a kit including a guiding system and a bone material removal device constructed and operative in accordance with some embodiments of the invention.

Reference is now made to FIG. 52, which is a simplified pictorial view illustration of a kit 5100 including a guiding system and a bone material removal device constructed and operative in accordance with another embodiment of the present invention.

It is noted that the bone material removal device 5200 may be any kind of drill or reamer available on the market, optionally modified as necessary, for example, to provide a bearing-borne pin or other bearing-borne marker. Preferably the bone material removal device 5200 is of a kind that is described above; for example, bone material removal device 4004, which enables drilling a bore having various diameters.

The kit 5100, including a guiding system and a bone material removal device 5200, preferably includes an arcuate element 5102, an engagement arm 5104 and a hollow cannula 5106; and one or two stoppers 5107, 5107B coupled to the cannula 5106. It is to be appreciated that the arcuate element 5102 and the engagement arm 5104 may be either securely attached one to another or integrally formed (in the latter case, a sliding degree of freedom is optionally given up). The engagement arm 5104 is preferably formed to fit the anatomical shape of a femur bone at the knee joint; or, alternatively, of a tibia bone at the knee joint. The arcuate element 5102 defines a tunnel 5108 for slideable insertion of the cannula 5106 therethrough.

The cannula 5106 is a generally longitudinal hollow element, which defines a proximal end portion 5110 proximally spaced from the tunnel 5108 of the arcuate element 5102 and a distal end portion 5112, which is insertable into the tunnel 5108.

It is a particular feature of an embodiment of the present invention that scale indications are provided on the distal end portion 5112 of the cannula 5106 for facilitating determination of actual bore length that is drilled through the femur bone of the knee joint. Optionally, scale indications are also provided on the proximal end of the cannula 5106 in order to determine bone-bridge length, which in turn defines the length of a bore with a lesser diameter of the various diameters of the bores drilled.

It is seen in FIG. 52 that a longitudinal groove 5114 is formed at the proximal end portion 5110 of the cannula 5106 and extends partially along the length of cannula 5106.

The stopper 5107 is a generally annular element, which optionally defines a longitudinally extending groove. The stopper 5107 is slideable and rotatably seated onto the cannula 5106 in a substantially tight fit manner.

It is seen in FIG. 52 that bone material removal device 5200 has a longitudinal shaft 5202 extending along a mutual longitudinal axis with cannula 5106. Bone material removal device 5200 additionally has a laterally extending pin 5204. The longitudinal shaft 5202 is insertable into the cannula 5106 of the kit including a guiding system and a bone material removal device 5100 and the laterally extending pin 5204 is slidably disposed in longitudinal groove 5114 of the cannula 5106. The pin 5204 is arranged transversely to a longitudinal axis of the cannula 5106.

In some embodiments, the stopper 5107 can be rotated to a position where the groove of the stopper 5107 is aligned with the longitudinal extent of pin 5204, such that the pin 5204 can be axially displaced through the groove of the stopper 5107. Additionally or alternatively, in some embodiments, the pin 5204 is attached to the bone material removal device 5200 after shaft 5202 is inserted to the cannula 5106. Additionally or alternatively, in some embodiments, stopper 5107 is placed on the cannula after the shaft 5202 is inserted to the cannula 5106.

It is noted that the longitudinal shaft 5202 of the bone removal device 5200 has a distal end with an expandable drill head 5208, as described in detail in previously filed patent application of the applicant of some embodiments of the present invention, such as in patent application PCT/IL2014/050381.

It is further appreciated that when the entire proximal end portion 5112 of the cannula 5106 is inserted into the tunnel 5108 of arcuate element 5102, distance L1 equals zero, as indicated by the scale indications provided on the proximal end portion 5112 of cannula 5106 and as the cannula is retracted proximally, L1 increases as indicated by the scale indications. Distance L2 is provided as a minimal distance between the distal end of cannula 5106 and the arm 5104, when the cannula is pushed fully distally in its holder. In some embodiments, the position of minimal distance is defined by a structure along the cannula (for example, a widening between a narrower and a wider outer diameter of the cannula) which interferes with the distal movement of the cannula beyond the position defining L2.

It is a particular feature of an embodiment of the present invention that sum of distances L1 and L2 (distance L3) defines the length of the bore that is drilled through the femur bone of the knee joint. Optionally, this distance is read directly from a scale marked on the cannula (the fully-pushed-distally position being marked with the distance value of L2, and greater distances being marked increasingly, accordingly). Alternatively, the distance L1 is read, and the full distance understood by adding in L2.

Figure 53:
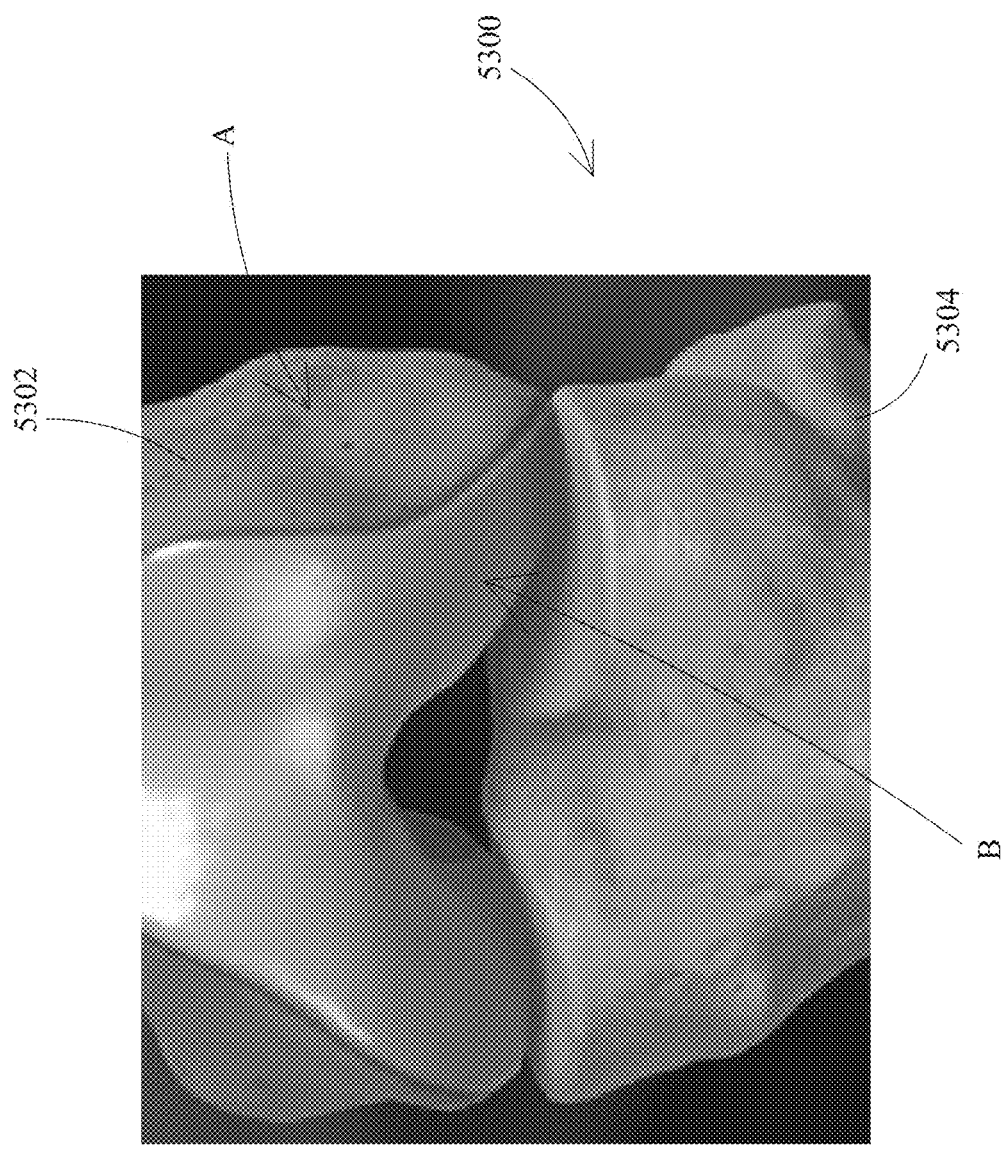
FIG. 53 is a simplified pictorial view illustration of a knee joint of a patient, according to some embodiments of the invention.

Reference is now made to FIG. 53, which is a simplified pictorial view illustration of a knee joint 5300 of a patient.

The knee joint 5300 is seen in FIG. 53 and includes a femur bone 5302 and a tibia bone 5304. Arrow A indicates the engagement area of the cannula 5106 of kit including a guiding system and a bone material removal device 5100 for initiation of drilling procedure and arrow B indicates the engagement area of the arm 5104, which shows the exit point of the drill head 5208 of the bone removal device 5200.

Figure 54B:
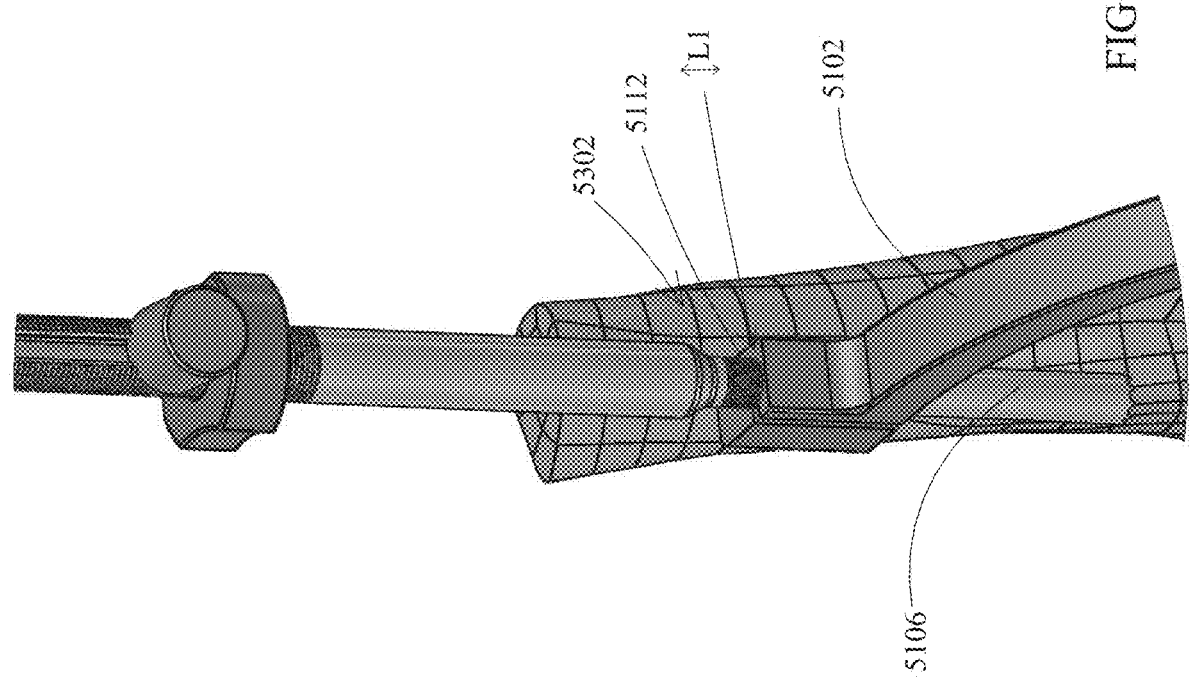
FIGS. 54A-54B are simplified pictorial view illustration of the kit including a guiding system and a bone material removal device secured to the knee joint, showing the bone material removal device while advanced distally into the joint and a respective enlargement view, according to some embodiments of the invention.
Figure 54A:
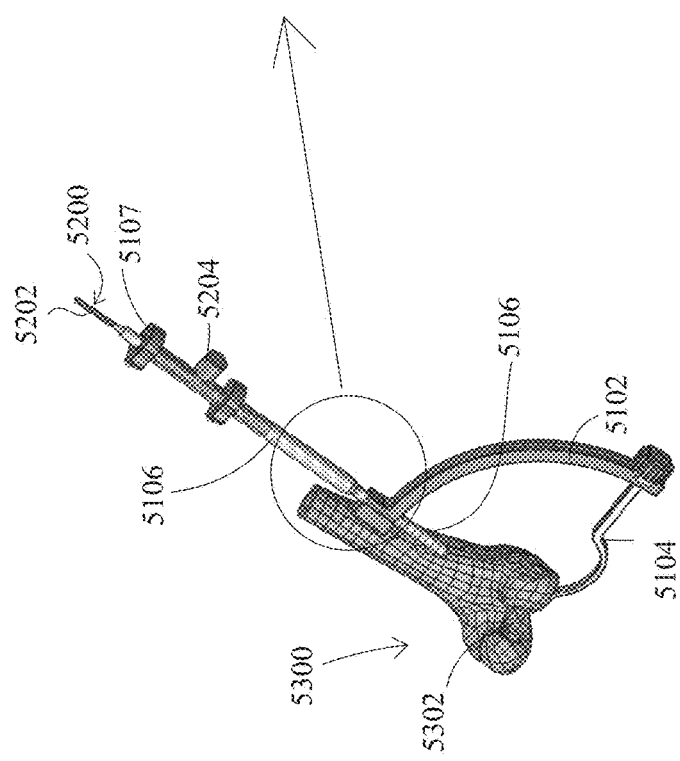

Reference is now made to FIGS. 54A-54B, which are a simplified pictorial view illustration of the kit including a guiding system and a bone material removal device 5100 secured to the knee joint 5300, showing the bone material removal device 5200 while advanced distally into the joint 5300 and a respective enlargement view.

In the operative position shown in FIGS. 54A-54B the cannula 5106 engages the entry point to femur bone 5302 and the arm 5104 engages the exit point on the femur bone 5302. The cannula 5106 is secured against the femur bone and the scale indications on the distal end portion 5112 of the cannula 5106 enable the user to determine the length of the bore to be drilled. Once the cannula 5106 is secured against the femur bone 5302, the bone material removal device 5200 is advanced distally and rotated in one direction, preferably clockwise, to drill a bore within the femur bone until the drill head 5208 of the bone material removal device 5200 reaches arm 5104. At this point a bore of a first diameter is drilled through the femur bone 5302 in accordance with the trajectory defined by the kit including a guiding system and a bone material removal device 5100 between the distal end 5112 of the cannula 5106 and the arm 5104.

Figure 55B:
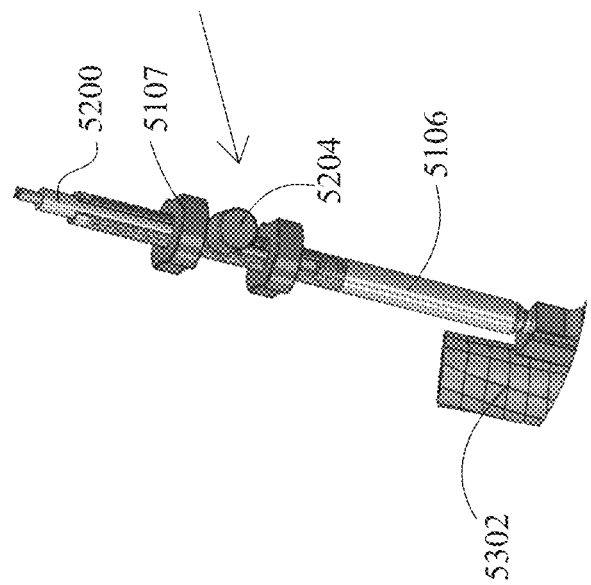
FIGS. 55A-55B are simplified pictorial view illustration of the kit including a guiding system and a bone material removal device secured to the knee joint, showing adjustment of the kit including a guiding system and a bone material removal device and a respective enlargement view, according to some embodiments of the invention.
Figure 55A:
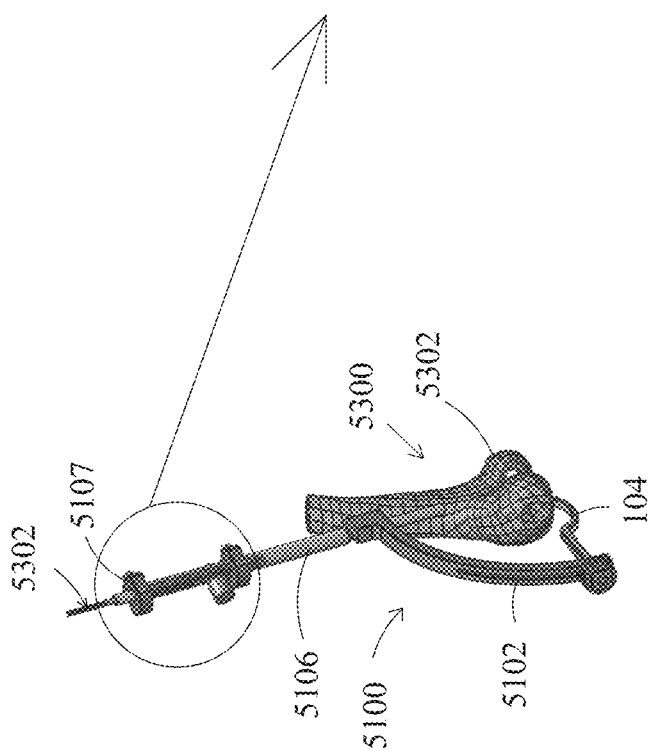

Reference is now made to FIGS. 55A-55B, which are a simplified pictorial view illustration of the kit including a guiding system and a bone material removal device 5100 secured to the knee joint 5300, showing adjustment of the kit including a guiding system and a bone material removal device 5100 and a respective enlargement view.

It is a particular feature of an embodiment of the present invention that the kit including a guiding system and a bone material removal device 5100 can be adjusted in order to provide an accurate bone-bridge length. Bone-bridge is defined as part of the length of the first diameter bore, which is drilled further in order to create a region of a second diameter, which is greater than the first diameter. Bone-bridge length is adjusted by axially displacing the stopper 5107 over cannula 5106, while the stopper 5107 engages pin 5204 of the bone material removal device 5200. Stopper 5107B, on the other hand, is optionally set to limit proximal travel of the bone material removal device; for example, to limit travel to the same point as set by the terminal structure of arm 5104, or to serve as an alternative method of limiting distal travel.

In some embodiments, pin 5204 is attached to the bone material removal device 5200 such that it translated with the shaft 5202 of the device in a longitudinal direction, but rotates freely on a bearing so that it can remain rotationally fixed relative to the cannula while the shaft spins. The length of the bone-bridge is indicated by the scale indications provided on the proximal end portion 5110 of the cannula 5106.

It is to be understood that the particular pin-and-stopper mechanism shown is exemplary of a more general concept, by which a rotationally free but longitudinally fixed element of the bone material removal device serves to limit movement by interactions with one or more longitudinally fixed elements of guiding system. For example, a bearing ring of the shaft is optionally provided with a longitudinal groove which is held rotationally in place by a track extending longitudinally along a part of the cannula. A potential advantage of such systems is that travel-limiting forces are focused to structures specialized for that role, potentially avoiding, for example, unbalanced torques on the hinges of the cutting teeth. Sudden, high-momentum change collisions of parts at high rotational speeds are also potentially avoided.

Alternatively, a circumferential groove or rim of the bearing could interlock with and/or bear against a portion of a stop attached to the guiding cannula. While the bearing would optionally be rotating most of the time with the shaft, the relatively low momentum of the bearing would potentially result in lessened mechanical shock upon stopping contact, compared to limiting by contact with a portion of the shaft which is rigidly coupled to the rest of the bone material removal device.

Figure 56A:
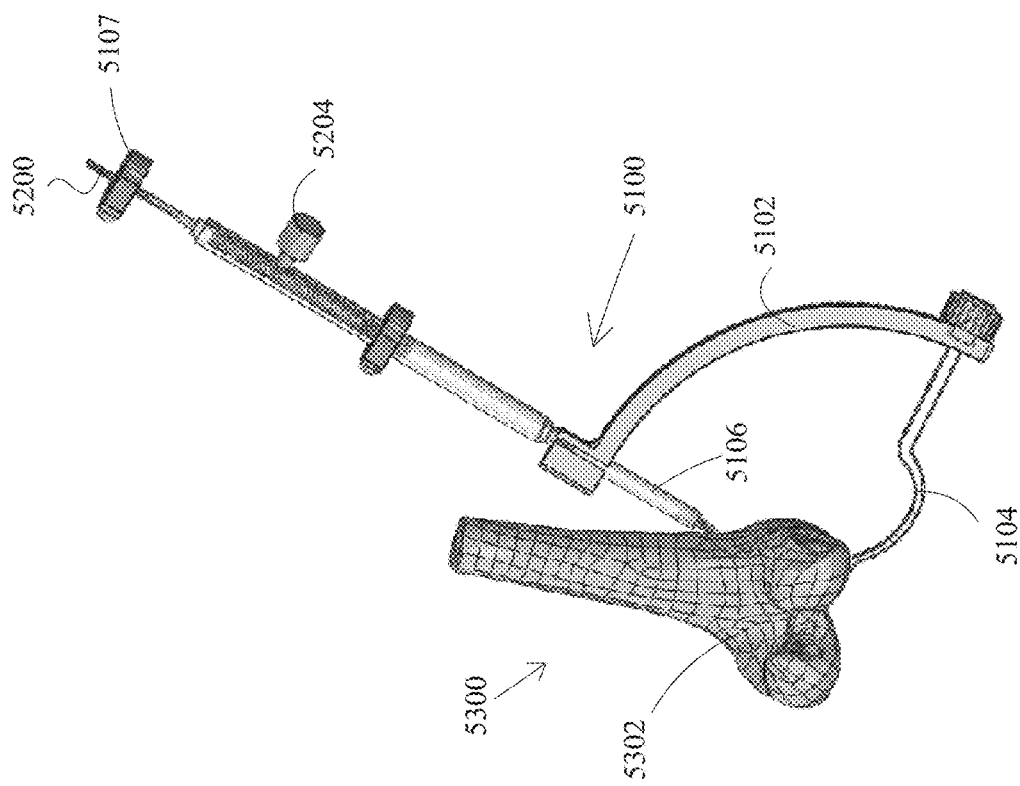
FIGS. 56A-56B are simplified pictorial view illustration of the kit including a guiding system and a bone material removal device secured to the knee joint, showing the bone material removal device while advanced proximally out of the joint and a respective enlargement view, according to some embodiments of the invention.
Figure 56B:
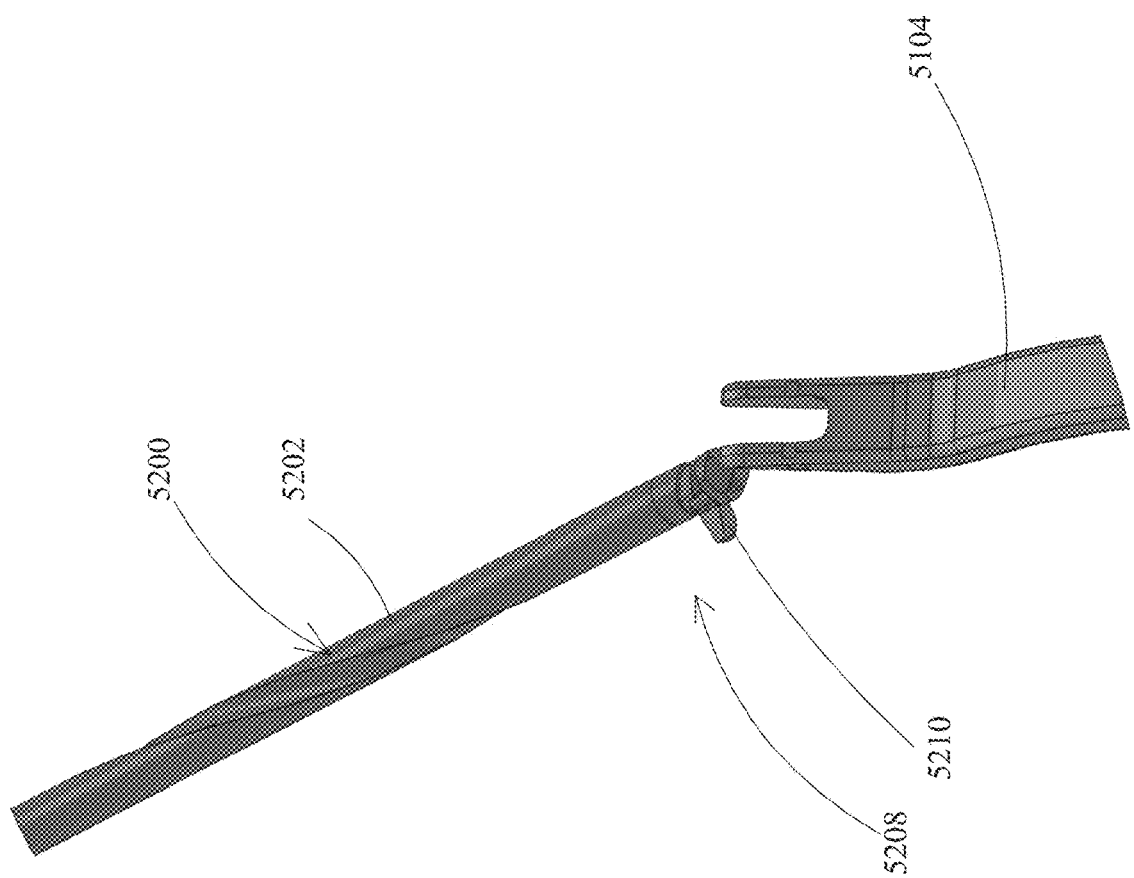

Reference is now made to FIGS. 56A-56B, which are a simplified pictorial view illustration of the kit including a guiding system and a bone material removal device 5100 secured to the knee joint 5300, showing the bone material removal device 5200 while advanced proximally out of the joint 5300 and a respective enlargement view.

At this operative stage, following adjustment to set a targeted bone-bridge length, the bone material removal device 5200 is proximally retracted out of the femur bone 5302 while the rotation direction of the drill head 5208 is reversed, and the drill head 5208 rotates in a preferably counter-clockwise direction, allowing expansion for reaming. The drill head 5208 has at least one laterally extending tooth 5210. When the drill head 5208 is rotated in the reversed direction, the tooth 5210 extends laterally from the outer circumference of the longitudinal shaft 5202 of the bone material removal device 5200 and thus a bore of a second diameter, which is greater than the first diameter is drilled through a part of the length of the first diameter bore, in accordance to the bone-bridge length that was adjusted as described with reference to FIGS. 55A-55B.

It is noted that following the drilling of the bore of second diameter, the bone material removal device 5200 is removed from the cannula 5106. Collapse of the head is performed, for example, by slow rotation in the clockwise direction while allowing the expanded tooth to "bounce" off the tunnel wall and back into its collapsed position. Finally, the cannula 5106 and the arm 5104 are disengaged from the femur bone 5302. Optionally, the arm is separately disengaged earlier (for example, before proximal withdrawal of the reamer).

Figure 58:
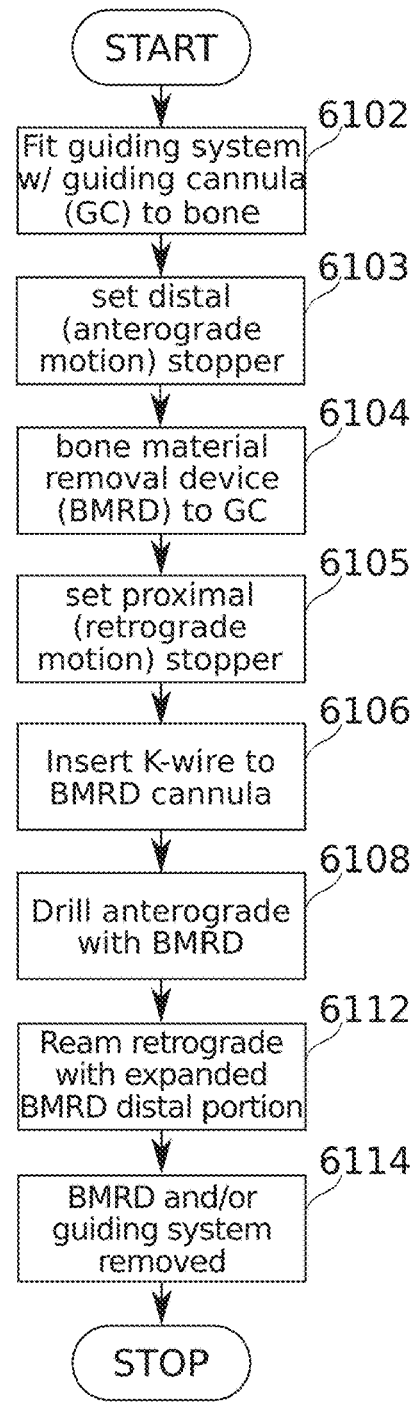
FIG. 58 shows a schematic flowchart of the use of the kit including a guiding system and a bone material removal device shown in FIG. 31, according to some embodiments of the invention.

Reference is now made to FIG. 58, which shows a schematic flowchart of the use of the kit 5100 including a guiding system and a bone material removal device 5200 shown in FIG. 31, according to some embodiments. In some embodiments, bone material removal depth is determined relative to scale markings on a cannula 5106 of the kit 5100.

At block 6102, in some embodiments, the guiding system comprising arc 4008, cannula 5106, and arm guide 5104 is placed against a bone (for example, a femur 5302), such that a portion of the bone is positioned between the distal end 5112 of the cannula and the hook and/or needle element of the guide 5104. The distal end 5112 of the cannula 5106 is positioned against the bone on one side, and the tip/hook of the guide 5104 is near and/or against the bone on the other side. Optionally, the positioning comprises sliding the cannula 5106 relative to the holder tunnel 5108, followed by a rotation of the cannula to engage its threads with the holder tunnel 5108. Optionally, the cannula 5106 is fixed to the bone by hammering. In some embodiments, this fixes the guiding system relative to the bone in preparation for bone material removal.

In some embodiments, cannula 5106 is provided with scale markings (for example, scale markings near distal end portion 5112), which allow the distance L3 between a distal tip 5112 of the cannula and the tip/hook of the guide 5104 to be readily determined by readout from the cannula markings. The distance may be read, for example, by adding a distance of withdrawal L1 to a known minimal distance L2. Alternatively, the scale markings directly correspond to the thickness of calipered bone which determines the tunnel length. Optionally, this also corresponds to the anterograde drilling depth. Alternatively, the anterograde drilling depth is offset slightly from the tunnel length to take into account particulars of the drill geometry (for example, a tapering tip and/or clearance for the expandable cutting portion of the bone material removal device). Optionally, this offset is taken into account (added) directly on the bone calipering scale; alternatively, it is added to it separately.

Optionally, the arc 4008 and/or arm guide 5104 are not used, or even not provided. In such cases, operations relating to the cannula 5106 and/or the stoppers 5107B, 5107 are performed, but other operations relating to the spatial relationships among guide system parts are omitted, or substituted with alternative implementations (for example, estimating distance by imaging).

Optionally, at block 6103, in some embodiments, a stopper 5107B is pushed into position on the cannula to provide a distal stop preventing further advance of the drill. Optionally, this position is set according to a reading on the guide cannula scale. Additionally or alternatively, distal advance is stopped during drilling by an encounter of the advancing bone material removal device with the terminal structure of the guide arm 5104, and/or simply by monitoring a scale on the advancing bone material removal device's shaft itself.

At block 6104, in some embodiments, a cannulated bone material removal device 5200 is inserted into the bore 4060 of cannula 5106. In some embodiments, a longitudinal slot along a proximal length of the cannula 5106 accommodates longitudinal movement of a pin 5204 which is bearing-coupled to the shaft of the bone material removal device 5200, while also preventing rotation (that is, the shaft rotates while the pin remains rotationally fixed by the longitudinal slot). In some embodiments, another arrangement for mechanical interference by the guiding cannula and/or a member mounted thereto with longitudinal movement of the bone material removal device is provided; for example, the stopper interlocks with a groove or interferes with a step on the shaft of the bone material removal device.

Optionally, at block 6105, a proximal stopper 5107 is placed where it will limit retrograde (proximal) movement of the expanded distal cutter, ensuring that a targeted thickness of bone bridge is left uncut. In some embodiments, one or both stoppers operate according to a ratchet mechanism: freely pushed in one direction, but locked in the other unless freed (for example, by a partial rotation to disengaged the ratchet, and/or by loosening of a set screw). Additionally or alternatively, the proximal stopper is placed/adjusted upon the completion of anterograde bone material removal.

Optionally, at block 6106, a K-wire 4006 is inserted into the cannula bore 4050 of the bone material removal device 5200. Potentially, this blocks debris from entering the cannula bore 4050 during bone material removal.

At block 6108, in some embodiments, anterograde bone material removal (e.g. drilling) is performed using the bone material removal device. The advance is stopped, for example, when the hole completely passes through the bone, by encounter with a stopper 5107B, with a terminal structure of arm 5104, and/or voluntarily by the operating surgeon.

At block 6112, in some embodiments, retrograde bone material removal is performed. The cutting tooth or teeth 4028 are deployed to their expanded position (for example, by centrifugal force and/or tooth engagement with the existing bore wall in the direction of tooth deployment), and the bone material removal device 5200 is gradually withdrawn while rotating. Encounter with stopper 5107 indicates that retrograde drilling is complete. Optionally, the arc 4008 and/or guide 5104 portions of the guiding system are released (before or after retrograde drilling) by unlocking rotation of the holder tunnel 5108 relative to the cannula 5106.

Optionally, at block 6114, the K-wire 4006 is replaced with surgical wire 4130. Remaining surgical steps of the grafting are optionally performed with one, both, or neither of the cannulated devices 5106, 5200 remaining in place.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments. The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A kit including a guiding system and a bone material removal device, comprising:
    a guiding cannula; and
    a bone material removal device axially displaceable within said cannula, said bone material removal device comprising a longitudinal shaft having distal and proximal ends, and
    a cutting portion comprising a radially extendable cutting tooth selectively positionable in an open and closed orientations, said tooth having a longitudinally-oriented cutting edge and is pivotably attached to a hinge member longitudinally oriented along said longitudinal shaft, said radial extension causes an increase of a cross-sectional diameter of said cutting portion of the said bone material removal device.

2. The kit according to claim 1, further comprising:
    a connecting member comprising a tunnel, wherein said guiding cannula is axially moveable within said tunnel; and
    a guide arm having a base end and a terminal structure end, and attachable to said connecting member at said base end wherein said terminal structure is located at or at least partially surrounding a region along said longitudinal direction when said guide arm and said connecting member are attached.

3. The kit according to claim 2, wherein the connecting member is arcuate in shape.

4. The kit of claim 1, wherein an inner diameter of the guiding cannula is sized to fittingly receive a portion of the longitudinal shaft which is axially displaceable within said cannula.

5. The kit according to claim 1, wherein said bone material removal device is cannulated.

6. The kit according to claim 1, wherein the radially extendable cutting tooth in a closed position extends radially beyond any adjacent circumference of the longitudinal shaft, and the inner diameter of the guiding cannula is sized to fittingly receive the extendable cutting tooth in the closed position.

7. The kit according to claim 1, further comprising at least one stopper, slidably displaceable over said cannula along the direction of said axial displacement.

8. The kit according to claim 7, wherein said bone material removal device further comprises a pin extending substantially transversely to said longitudinal shaft, and positioned to contact said at least one stopper and limit longitudinal travel of the bone material removal device.

9. The kit according to claim 8, wherein said pin is attached to the longitudinal shaft by a rotating bearing, such that the shaft is free to rotate while the pin remains rotationally stationary.

10. The kit according to claim 8, wherein the longitudinal position of the pin is fixed relative to the longitudinal shaft.

11. The kit according to claim 8, wherein said stopper comprises a groove formed therein, sized and positioned to allow displacement of said pin through said stopper while said stopper is attached to said cannula.

12. The kit according to claim 2, wherein the terminal structure at least partially surrounds the region along the longitudinal direction, outside a circumference having the diameter of the longitudinal shaft of the bone material removal device.

13. The kit according to claim 2, wherein said guiding cannula comprises a distance scale indicating overall bone tunnel length, and said scale is marked such that a distalmost slideable position of said cannula provides a reference position defining a smallest distance between a distal tip of said guiding cannula and said terminal structure.

14. The kit according to claim 13, wherein said cannula comprises a widening which interferes with said connecting member to limit distal movement of said cannula to a position defining said smallest distance.

15. The kit according to claim 13, wherein distances of said scale are marked as the actual length of a bone tunnel defined by the relative positions of said cannula and said terminal structure of said guide arm.

16. The kit according to claim 13, wherein a second scale is marked on said bone material removal device, that indicates retrograde cutting distance as said bone material device is withdrawn proximally.

17. The kit according to claim 16, wherein said cannula scale and said bone removal device scale are coordinated, such that a current distance reading on said scale marked on said cannula gives a position on said bone material removal device scale to which longitudinal travel should be limited during formation of a bone tunnel.

18. A method of drilling a bone tunnel in a bone comprising:
    positioning a guiding cannula on the bone;
    inserting a bone material removal device into said cannula;
    forming a bone tunnel in the anterograde direction through the bone while advancing said bone material removal device;
    extending an extendable cutting tooth of said bone material removal device to assume an open position; and
    expanding the bone tunnel in the retrograde direction while withdrawing said bone material removal device;
    wherein said bone material removal device rotates in a first direction when advancing and rotates in an opposite direction when withdrawing said bone material removal device.

19. The method according to claim 18, wherein said cutting tooth pivotably attached to a hinge member longitudinally oriented along a longitudinal shaft of said bone material removal device.

* * * * *